(12) United States Patent
Knudson et al.

(10) Patent No.: US 12,268,876 B2
(45) Date of Patent: Apr. 8, 2025

(54) NEURAL BLOCKING THERAPY

(71) Applicant: Flathead Partners, LLC, Minneapolis, MN (US)

(72) Inventors: Mark B. Knudson, Shoreview, MN (US); Adrianus P. Donders, Andover, MN (US); Timothy R. Conrad, Eden Prairie, MN (US)

(73) Assignee: Flathead Partners, LLC, Minneapolis, MN (US)

( * ) Notice: Subject to any disclaimer, the term of this patent is extended or adjusted under 35 U.S.C. 154(b) by 0 days.

(21) Appl. No.: 16/286,389

(22) Filed: Feb. 26, 2019

(65) Prior Publication Data

US 2019/0184170 A1 Jun. 20, 2019

Related U.S. Application Data

(63) Continuation of application No. 14/922,009, filed on Oct. 23, 2015, now abandoned, which is a (Continued)

(51) Int. Cl.
*A61N 1/36* (2006.01)
*A61N 1/05* (2006.01)

(52) U.S. Cl.
CPC ....... *A61N 1/36071* (2013.01); *A61N 1/0551* (2013.01); *A61N 1/36064* (2013.01); (Continued)

(58) Field of Classification Search
CPC ............ A61N 1/36071; A61N 1/36067; A61N 1/0551; A61N 1/36064; A61N 1/0531; A61N 1/0534
See application file for complete search history.

(56) References Cited

U.S. PATENT DOCUMENTS 1,597,061 A 8/1926 Cultra et al.
2,622,601 A 12/1952 Nemec
(Continued)

FOREIGN PATENT DOCUMENTS

DE 10318071 A1 11/2004
EP 1181947 A2 2/2002
(Continued)

OTHER PUBLICATIONS

U.S. Appl. No. 14/534,769, filed Nov. 6, 2014, Park.
(Continued)

*Primary Examiner* — Catherine M Voorhees
(74) *Attorney, Agent, or Firm* — Perkins Coie LLP

(57) ABSTRACT

A method and apparatus are disclosed for treating a variety of conditions include treating a disorder associated with neural activity near a region of a brain. In such condition, the method includes placing an electrode to create a field near said region, creating said field with parameters selected to at least partially block neural activity within said field. For treating a tissue sensation, the method includes identifying a target area of tissue to be treated and placing an electrode to create a field near the target area, and creating the field with parameters selected to at least partially block neural activity within the target area. For treating a condition associated with neural activity of a spinal cord, the method includes placing an electrode to create a field near a nerve associated with the spinal cord, and creating the field with parameters selected to at least partially block neural activity within the nerve.

6 Claims, 6 Drawing Sheets

Related U.S. Application Data continuation of application No. 14/059,246, filed on Oct. 21, 2013, now abandoned, which is a continuation of application No. 11/235,947, filed on Sep. 26, 2005, now abandoned.

(52) U.S. Cl.
CPC ........ *A61N 1/36067* (2013.01); *A61N 1/0531* (2013.01); *A61N 1/0534* (2013.01)

(56) References Cited

U.S. PATENT DOCUMENTS

| | | |
|---|---|---|
| 3,195,540 A | 7/1965 | Waller |
| 3,646,940 A | 3/1972 | Timm et al. |
| 3,724,467 A * | 4/1973 | Avery .................. A61N 1/0551 607/117 |
| 3,727,616 A | 4/1973 | Lenzkes |
| 3,817,254 A | 6/1974 | Maurer |
| 3,822,708 A | 7/1974 | Zilber |
| 3,893,463 A | 7/1975 | Williams |
| 4,014,347 A | 3/1977 | Halleck et al. |
| 4,023,574 A | 5/1977 | Nemec |
| 4,055,190 A | 10/1977 | Tany et al. |
| 4,148,321 A | 4/1979 | Wyss et al. |
| 4,315,503 A | 2/1982 | Ryaby et al. |
| 4,379,462 A | 4/1983 | Borkan et al. |
| 4,414,986 A | 11/1983 | Dickhudt et al. |
| 4,459,989 A | 7/1984 | Borkan |
| 4,535,777 A | 8/1985 | Castel |
| 4,541,432 A | 9/1985 | Molina-Negro et al. |
| 4,608,985 A | 9/1986 | Crish et al. |
| 4,612,934 A | 9/1986 | Borkan et al. |
| 4,649,935 A | 3/1987 | Charmillot et al. |
| 4,702,254 A | 10/1987 | Zabara |
| 4,735,204 A | 4/1988 | Sussman et al. |
| 4,764,132 A | 8/1988 | Stutz, Jr. |
| 4,793,353 A | 12/1988 | Borkan et al. |
| 4,841,973 A | 6/1989 | Stecker |
| RE33,420 E | 11/1990 | Sussman et al. |
| 5,002,053 A | 3/1991 | Garcia-Rill |
| 5,058,584 A | 10/1991 | Bourgeois |
| 5,121,754 A | 6/1992 | Mullett |
| 5,167,229 A | 12/1992 | Peckham et al. |
| 5,188,104 A | 2/1993 | Wernicke et al. |
| 5,299,569 A | 4/1994 | Wernicke et al. |
| 5,335,657 A | 8/1994 | Terry, Jr. et al. |
| 5,354,320 A | 10/1994 | Schaldach et al. |
| 5,417,719 A | 5/1995 | Hull et al. |
| 5,501,703 A | 3/1996 | Holsheimer et al. |
| 5,514,175 A | 5/1996 | Kim et al. |
| 5,540,730 A | 7/1996 | Terry, Jr. et al. |
| 5,540,734 A | 7/1996 | Zabara |
| 5,562,717 A | 10/1996 | Tippey et al. |
| 5,643,330 A | 7/1997 | Holsheimer et al. |
| 5,707,396 A | 1/1998 | Benabid |
| 5,716,377 A | 2/1998 | Rise et al. |
| 5,733,322 A | 3/1998 | Starkebaum |
| 5,755,758 A * | 5/1998 | Woloszko ................ A61N 1/05 607/116 |
| 5,776,170 A | 7/1998 | MacDonald et al. |
| 5,792,187 A | 8/1998 | Adams |
| 5,830,151 A | 11/1998 | Hadzic et al. |
| 5,833,709 A | 11/1998 | Rise |
| 5,853,373 A | 12/1998 | Griffith et al. |
| 5,893,883 A | 4/1999 | Torgerson |
| 5,895,416 A | 4/1999 | Barreras, Sr. et al. |
| 5,925,070 A | 7/1999 | King et al. |
| 5,938,690 A | 8/1999 | Law |
| 5,948,007 A | 9/1999 | Starkebaum et al. |
| 5,983,141 A | 11/1999 | Sluijter et al. |
| 5,995,872 A | 11/1999 | Bourgeois |
| 6,002,964 A * | 12/1999 | Feler .................. A61N 1/0551 607/46 |
| 6,014,588 A | 1/2000 | Fitz |
| 6,027,456 A | 2/2000 | Feler et al. |
| 6,049,701 A | 4/2000 | Sparksman |
| 6,104,957 A | 8/2000 | Alo et al. |
| 6,161,044 A | 12/2000 | Silverstone |
| 6,161,048 A | 12/2000 | Sluijter et al. |
| 6,167,305 A | 12/2000 | Cammilli et al. |
| 6,167,311 A | 12/2000 | Rezai |
| 6,176,242 B1 | 1/2001 | Rise |
| 6,233,488 B1 | 5/2001 | Hess |
| 6,236,892 B1 | 5/2001 | Feler et al. |
| 6,238,423 B1 | 5/2001 | Bardy |
| 6,246,912 B1 | 6/2001 | Sluijter et al. |
| 6,249,707 B1 | 6/2001 | Kohnen et al. |
| 6,309,401 B1 | 10/2001 | Redko et al. |
| 6,319,241 B1 | 11/2001 | King et al. |
| 6,341,236 B1 | 1/2002 | Osorio et al. |
| 6,356,786 B1 | 3/2002 | Rezai et al. |
| 6,366,814 B1 | 4/2002 | Boveja |
| 6,381,496 B1 | 4/2002 | Meadows et al. |
| 6,393,325 B1 | 5/2002 | Mann et al. |
| 6,397,108 B1 | 5/2002 | Camps et al. |
| 6,405,079 B1 | 6/2002 | Ansarinia |
| 6,421,566 B1 | 7/2002 | Holsheimer |
| 6,438,423 B1 | 8/2002 | Rezai et al. |
| 6,440,090 B1 | 8/2002 | Schallhorn |
| 6,473,644 B1 | 10/2002 | Terry, Jr. et al. |
| 6,505,078 B1 | 1/2003 | King et al. |
| 6,510,347 B2 | 1/2003 | Borkan |
| 6,516,227 B1 | 2/2003 | Meadows et al. |
| 6,526,318 B1 | 2/2003 | Ansarinia |
| 6,553,264 B2 | 4/2003 | Redko et al. |
| 6,571,127 B1 | 5/2003 | Ben-Haim et al. |
| 6,584,358 B2 | 6/2003 | Carter et al. |
| 6,587,727 B2 | 7/2003 | Osorio et al. |
| 6,600,954 B2 | 7/2003 | Cohen et al. |
| 6,609,030 B1 | 8/2003 | Rezai et al. |
| 6,609,031 B1 | 8/2003 | Law et al. |
| 6,610,713 B2 | 8/2003 | Tracey |
| 6,622,047 B2 | 9/2003 | Barrett et al. |
| 6,622,048 B1 | 9/2003 | Mann |
| 6,659,968 B1 | 12/2003 | McClure |
| 6,662,051 B1 | 12/2003 | Eraker et al. |
| 6,671,556 B2 | 12/2003 | Osorio et al. |
| 6,675,046 B2 | 1/2004 | Holsheimer |
| 6,684,105 B2 | 1/2004 | Cohen et al. |
| 6,714,822 B2 | 3/2004 | King et al. |
| 6,721,603 B2 | 4/2004 | Zabara et al. |
| 6,754,539 B1 | 6/2004 | Erickson et al. |
| 6,761,715 B2 | 7/2004 | Carroll |
| 6,795,737 B2 | 9/2004 | Gielen et al. |
| 6,856,315 B2 | 2/2005 | Eberlein |
| 6,862,479 B1 | 3/2005 | Whitehurst |
| 6,871,090 B1 | 3/2005 | He et al. |
| 6,871,099 B1 | 3/2005 | Whitehurst et al. |
| 6,885,888 B2 | 4/2005 | Rezai |
| 6,892,097 B2 | 5/2005 | Holsheimer et al. |
| 6,895,280 B2 | 5/2005 | Meadows et al. |
| 6,907,295 B2 | 6/2005 | Gross et al. |
| 6,920,357 B2 | 7/2005 | Osorio et al. |
| 6,923,784 B2 | 8/2005 | Stein |
| 6,928,230 B2 | 8/2005 | Squibbs |
| 6,928,280 B2 | 8/2005 | Xanthos et al. |
| 6,928,320 B2 | 8/2005 | King |
| 6,944,501 B1 | 9/2005 | Pless |
| 6,950,707 B2 | 9/2005 | Whitehurst |
| 6,959,215 B2 | 10/2005 | Gliner |
| 6,961,618 B2 | 11/2005 | Osorio et al. |
| 6,968,237 B2 | 11/2005 | Doan et al. |
| 6,990,376 B2 | 1/2006 | Tanagho et al. |
| 7,024,246 B2 | 4/2006 | Acosta et al. |
| 7,047,079 B2 | 5/2006 | Erickson |
| 7,054,686 B2 | 5/2006 | MacDonald |
| 7,082,333 B1 | 7/2006 | Bauhahn et al. |
| 7,117,034 B2 | 10/2006 | Kronberg |
| 7,146,222 B2 | 12/2006 | Boling |
| 7,146,223 B1 | 12/2006 | King |
| 7,146,224 B2 | 12/2006 | King |
| 7,149,574 B2 | 12/2006 | Yun et al. |
| 7,162,303 B2 | 1/2007 | Levin et al. |

(56) References Cited

U.S. PATENT DOCUMENTS

| | | |
|---|---|---|
| 7,162,304 B1 | 1/2007 | Bradley |
| 7,167,750 B2 | 1/2007 | Knudson et al. |
| 7,174,215 B2 | 2/2007 | Bradley |
| 7,177,690 B2 | 2/2007 | Woods et al. |
| 7,177,691 B2 | 2/2007 | Meadows et al. |
| 7,177,702 B2 | 2/2007 | Wallace et al. |
| 7,180,760 B2 | 2/2007 | Varrichio et al. |
| 7,206,640 B1 | 4/2007 | Overstreet |
| 7,212,865 B2 | 5/2007 | Cory |
| 7,225,035 B2 | 5/2007 | Brabec et al. |
| 7,231,254 B2 | 6/2007 | DiLorenzo |
| 7,236,822 B2 | 6/2007 | Dobak, III |
| 7,239,912 B2 | 7/2007 | Dobak, III |
| 7,242,984 B2 | 7/2007 | DiLorenzo |
| 7,252,090 B2 | 8/2007 | Goetz |
| 7,260,436 B2 | 8/2007 | Kilgore et al. |
| 7,263,402 B2 | 8/2007 | Thacker et al. |
| 7,266,412 B2 | 9/2007 | Stypulkowski |
| 7,276,057 B2 | 10/2007 | Gerber |
| 7,288,062 B2 | 10/2007 | Spiegel |
| 7,313,440 B2 | 12/2007 | Miesel |
| 7,324,852 B2 | 1/2008 | Barolat et al. |
| 7,326,181 B2 | 2/2008 | Katims |
| 7,333,857 B2 | 2/2008 | Campbell |
| 7,337,005 B2 | 2/2008 | Kim et al. |
| 7,337,006 B2 | 2/2008 | Kim et al. |
| 7,346,398 B2 | 3/2008 | Gross et al. |
| 7,349,743 B2 | 3/2008 | Tadlock |
| RE40,279 E | 4/2008 | Sluijter et al. |
| 7,359,751 B1 | 4/2008 | Erickson et al. |
| 7,363,076 B2 | 4/2008 | Yun et al. |
| 7,389,145 B2 | 6/2008 | Kilgore et al. |
| 7,393,351 B2 | 7/2008 | Woloszko et al. |
| 7,433,734 B2 | 10/2008 | King |
| 7,444,183 B2 | 10/2008 | Knudson et al. |
| 7,447,546 B2 | 11/2008 | Kim et al. |
| 7,450,993 B2 | 11/2008 | Kim et al. |
| 7,463,927 B1 | 12/2008 | Chaouat |
| 7,483,747 B2 | 1/2009 | Gliner et al. |
| 7,489,969 B2 | 2/2009 | Knudson et al. |
| 7,493,172 B2 | 2/2009 | Whitehurst et al. |
| 7,496,404 B2 | 2/2009 | Meadows et al. |
| 7,502,651 B2 | 3/2009 | Kim et al. |
| 7,502,652 B2 | 3/2009 | Gaunt et al. |
| 7,571,007 B2 | 8/2009 | Erickson et al. |
| 7,580,753 B2 | 8/2009 | Kim et al. |
| 7,599,737 B2 | 10/2009 | Yomtov et al. |
| 7,634,317 B2 | 12/2009 | Ben-David et al. |
| 7,676,269 B2 | 3/2010 | Yun et al. |
| 7,689,276 B2 | 3/2010 | Dobak |
| 7,689,289 B2 | 3/2010 | King |
| 7,711,432 B2 | 5/2010 | Thimineur et al. |
| 7,715,915 B1 | 5/2010 | Rye et al. |
| 7,734,340 B2 | 6/2010 | De Ridder |
| 7,742,810 B2 | 6/2010 | Moffitt et al. |
| 7,761,170 B2 | 7/2010 | Kaplan et al. |
| 7,778,704 B2 | 8/2010 | Rezai |
| 7,813,803 B2 | 10/2010 | Heruth et al. |
| 7,826,901 B2 | 11/2010 | Lee et al. |
| 7,853,322 B2 | 12/2010 | Bourget et al. |
| 7,860,570 B2 | 12/2010 | Whitehurst et al. |
| 7,877,136 B1 | 1/2011 | Moffitt et al. |
| 7,877,146 B2 | 1/2011 | Rezai |
| 7,881,805 B2 | 2/2011 | Bradley |
| 7,890,163 B2 | 2/2011 | Belalcazar |
| 7,890,176 B2 | 2/2011 | Jaax et al. |
| 7,890,182 B2 | 2/2011 | Parramon et al. |
| 7,914,452 B2 | 3/2011 | Hartley et al. |
| 7,933,654 B2 | 4/2011 | Merfeld et al. |
| 7,937,145 B2 | 5/2011 | Dobak |
| 8,000,794 B2 | 8/2011 | Lozano |
| 8,010,198 B2 | 8/2011 | Libbus et al. |
| 8,027,718 B2 | 9/2011 | Spinner |
| 8,046,075 B2 | 10/2011 | Rezai |
| 8,060,208 B2 | 11/2011 | Kilgore et al. |
| 8,082,039 B2 | 12/2011 | Kim et al. |
| 8,170,675 B2 | 5/2012 | Alataris et al. |
| 8,209,021 B2 | 6/2012 | Alataris et al. |
| 8,209,028 B2 | 6/2012 | Skelton et al. |
| 8,224,453 B2 | 7/2012 | De Ridder |
| 8,224,459 B1 | 7/2012 | Pianca |
| 8,255,057 B2 | 8/2012 | Ping et al. |
| 8,280,515 B2 | 10/2012 | Greenspan |
| 8,340,775 B1 | 12/2012 | Cullen et al. |
| 8,355,792 B2 | 1/2013 | Alataris et al. |
| 8,359,102 B2 | 1/2013 | Alataris et al. |
| 8,359,103 B2 | 1/2013 | Alataris et al. |
| 8,364,271 B2 | 1/2013 | De Ridder |
| 8,364,273 B2 | 1/2013 | De Ridder |
| 8,380,318 B2 | 2/2013 | Kishawi et al. |
| 8,396,559 B2 | 3/2013 | Alataris |
| 8,423,147 B2 | 4/2013 | Alataris et al. |
| 8,428,735 B2 | 4/2013 | Littlewood et al. |
| 8,428,748 B2 | 4/2013 | Alataris et al. |
| 8,509,905 B2 | 8/2013 | Alataris et al. |
| 8,612,018 B2 | 12/2013 | Gillbe |
| 8,649,874 B2 | 2/2014 | Alataris et al. |
| 8,666,506 B2 | 3/2014 | King |
| 8,751,009 B2 | 6/2014 | Wacnik |
| 8,768,469 B2 | 7/2014 | Tweden et al. |
| 8,805,544 B2 | 8/2014 | Pianca et al. |
| 8,805,554 B1 | 8/2014 | Pianca et al. |
| 8,825,166 B2 | 9/2014 | John |
| 8,886,326 B2 | 11/2014 | Alataris et al. |
| 8,886,328 B2 | 11/2014 | Alataris et al. |
| 8,892,209 B2 | 11/2014 | Alataris et al. |
| 8,918,172 B2 | 12/2014 | Moffitt et al. |
| 8,918,190 B2 | 12/2014 | Libbus et al. |
| 9,002,459 B2 | 4/2015 | Lee et al. |
| 9,067,076 B2 | 6/2015 | Nolan et al. |
| 9,180,298 B2 | 11/2015 | Alataris et al. |
| 9,295,840 B1 | 3/2016 | Thacker |
| 9,327,127 B2 | 5/2016 | Alataris et al. |
| 9,381,356 B2 | 7/2016 | Parker |
| 9,480,846 B2 | 11/2016 | Strother |
| 9,555,248 B2 | 1/2017 | De Ridder |
| 9,561,370 B2 | 2/2017 | Rezai |
| 9,833,614 B1 | 12/2017 | Gliner |
| 9,895,539 B1 | 2/2018 | Heit et al. |
| 10,076,668 B2 | 9/2018 | De Ridder |
| 10,092,758 B2 | 10/2018 | De Ridder |
| 10,149,978 B1 | 12/2018 | Park |
| 10,493,275 B2 | 12/2019 | Alataris |
| 2002/0055779 A1 | 5/2002 | Andrews |
| 2002/0128700 A1 | 9/2002 | Cross |
| 2003/0036783 A1 | 2/2003 | Bauhahn |
| 2003/0100931 A1 | 5/2003 | Mullett |
| 2003/0114899 A1* | 6/2003 | Woods ............... A61N 1/36071 607/60 |
| 2003/0120323 A1 | 6/2003 | Meadows et al. |
| 2003/0125786 A1 | 7/2003 | Gliner et al. |
| 2003/0144709 A1 | 7/2003 | Zabara et al. |
| 2003/0149450 A1 | 8/2003 | Mayberg |
| 2003/0195602 A1 | 10/2003 | Boling |
| 2003/0204221 A1 | 10/2003 | Rodriguez et al. |
| 2004/0015202 A1 | 1/2004 | Chandler et al. |
| 2004/0034394 A1 | 2/2004 | Woods et al. |
| 2004/0039425 A1 | 2/2004 | Greenwood-Van Meerveld |
| 2004/0059395 A1 | 3/2004 | North et al. |
| 2004/0073273 A1 | 4/2004 | Gluckman et al. |
| 2004/0093093 A1 | 5/2004 | Andrews |
| 2004/0116977 A1 | 6/2004 | Finch et al. |
| 2004/0116978 A1 | 6/2004 | Bradley |
| 2004/0122477 A1 | 6/2004 | Whitehorse |
| 2004/0127942 A1 | 7/2004 | Yomtov et al. |
| 2004/0127953 A1* | 7/2004 | Kilgore ............... A61N 1/32 607/46 |
| 2004/0158839 A1 | 8/2004 | Gliner et al. |
| 2004/0162590 A1 | 8/2004 | Whitehurst et al. |
| 2004/0167583 A1 | 8/2004 | Knudson et al. |
| 2004/0167584 A1 | 8/2004 | Carroll et al. |
| 2004/0172085 A1 | 9/2004 | Knudson et al. |
| 2004/0172086 A1 | 9/2004 | Knudson et al. |
| 2004/0172088 A1 | 9/2004 | Knudson et al. |

(56) References Cited

U.S. PATENT DOCUMENTS

| | | |
|---|---|---|
| 2004/0176812 A1 | 9/2004 | Knudson et al. |
| 2004/0186532 A1 | 9/2004 | Tadlock |
| 2004/0193228 A1 | 9/2004 | Gerber |
| 2004/0210270 A1 | 10/2004 | Erickson |
| 2004/0210271 A1 | 10/2004 | Campen et al. |
| 2004/0243205 A1 | 12/2004 | Keravel et al. |
| 2004/0267330 A1 | 12/2004 | Lee et al. |
| 2005/0021104 A1 | 1/2005 | DiLorenzo |
| 2005/0033381 A1 | 2/2005 | Carter et al. |
| 2005/0038484 A1 | 2/2005 | Knudson et al. |
| 2005/0038489 A1 | 2/2005 | Grill |
| 2005/0038490 A1 | 2/2005 | Gross et al. |
| 2005/0060001 A1 | 3/2005 | Singhal et al. |
| 2005/0070982 A1 | 3/2005 | Heruth et al. |
| 2005/0113877 A1 | 5/2005 | Spinelli et al. |
| 2005/0113878 A1 | 5/2005 | Gerber |
| 2005/0113882 A1 | 5/2005 | Cameron et al. |
| 2005/0119703 A1 | 6/2005 | DiLorenzo |
| 2005/0119713 A1 | 6/2005 | Whitehurst et al. |
| 2005/0143788 A1 | 6/2005 | Yun et al. |
| 2005/0143789 A1 | 6/2005 | Whitehurst et al. |
| 2005/0149148 A1 | 7/2005 | King |
| 2005/0153885 A1 | 7/2005 | Yun et al. |
| 2005/0154435 A1 | 7/2005 | Stern et al. |
| 2005/0182453 A1 | 8/2005 | Whitehurst et al. |
| 2005/0228451 A1* | 10/2005 | Jaax .................. A61N 1/36071 607/2 |
| 2005/0240241 A1 | 10/2005 | Yun et al. |
| 2005/0245978 A1 | 11/2005 | Varrichio et al. |
| 2005/0245987 A1 | 11/2005 | Woods |
| 2005/0246006 A1 | 11/2005 | Daniels |
| 2005/0267545 A1 | 12/2005 | Cory |
| 2005/0278000 A1 | 12/2005 | Strother et al. |
| 2006/0004422 A1 | 1/2006 | De Ridder |
| 2006/0009820 A1 | 1/2006 | Royle |
| 2006/0015153 A1 | 1/2006 | Gliner et al. |
| 2006/0030895 A1 | 2/2006 | Simon et al. |
| 2006/0041285 A1 | 2/2006 | Johnson |
| 2006/0052836 A1* | 3/2006 | Kim .................... A61N 1/0558 607/48 |
| 2006/0074456 A1 | 4/2006 | Pyles et al. |
| 2006/0079934 A1 | 4/2006 | Ogawa et al. |
| 2006/0079937 A1 | 4/2006 | King et al. |
| 2006/0095088 A1* | 5/2006 | De Ridder ......... A61N 1/36085 607/48 |
| 2006/0100671 A1 | 5/2006 | Ridder |
| 2006/0116742 A1 | 6/2006 | De Ridder |
| 2006/0149337 A1 | 7/2006 | John |
| 2006/0161219 A1 | 7/2006 | Mock et al. |
| 2006/0161235 A1 | 7/2006 | King |
| 2006/0167512 A1 | 7/2006 | Ross et al. |
| 2006/0167525 A1 | 7/2006 | King |
| 2006/0168805 A1 | 8/2006 | Hegland et al. |
| 2006/0190048 A1 | 8/2006 | Gerber |
| 2006/0224187 A1 | 10/2006 | Bradley et al. |
| 2006/0229687 A1 | 10/2006 | Goetz et al. |
| 2006/0253182 A1 | 11/2006 | King |
| 2007/0021801 A1 | 1/2007 | Heruth et al. |
| 2007/0021802 A1 | 1/2007 | Heruth et al. |
| 2007/0021803 A1 | 1/2007 | Deem et al. |
| 2007/0032827 A1 | 2/2007 | Katims |
| 2007/0039625 A1 | 2/2007 | Heruth et al. |
| 2007/0043400 A1 | 2/2007 | Donders et al. |
| 2007/0049988 A1 | 3/2007 | Carbunaru |
| 2007/0049991 A1 | 3/2007 | Klostermann et al. |
| 2007/0060954 A1 | 3/2007 | Cameron et al. |
| 2007/0066997 A1 | 3/2007 | He et al. |
| 2007/0073353 A1 | 3/2007 | Rooney et al. |
| 2007/0073354 A1 | 3/2007 | Knudson et al. |
| 2007/0083240 A1 | 4/2007 | Peterson et al. |
| 2007/0106337 A1 | 5/2007 | Errico et al. |
| 2007/0106342 A1 | 5/2007 | Schumann |
| 2007/0142863 A1 | 6/2007 | Bradley |
| 2007/0150029 A1 | 6/2007 | Bourget et al. |
| 2007/0150034 A1 | 6/2007 | Rooney et al. |
| 2007/0156183 A1 | 7/2007 | Rhodes |
| 2007/0167992 A1 | 7/2007 | Carley |
| 2007/0179559 A1 | 8/2007 | Giftakis et al. |
| 2007/0179579 A1 | 8/2007 | Feler et al. |
| 2007/0203537 A1 | 8/2007 | Goetz et al. |
| 2007/0213771 A1 | 9/2007 | Spinner et al. |
| 2007/0213789 A1 | 9/2007 | Nolan et al. |
| 2007/0239226 A1 | 10/2007 | Overstreet |
| 2007/0244522 A1 | 10/2007 | Overstreet |
| 2007/0255118 A1 | 11/2007 | Miesel et al. |
| 2007/0265675 A1 | 11/2007 | Lund et al. |
| 2007/0265681 A1 | 11/2007 | Gerber et al. |
| 2007/0276319 A1 | 11/2007 | Betts |
| 2007/0293915 A1 | 12/2007 | Kilgore et al. |
| 2007/0299482 A1 | 12/2007 | Littlewood et al. |
| 2008/0015667 A1 | 1/2008 | Gross |
| 2008/0033511 A1 | 2/2008 | Dobak |
| 2008/0058878 A1 | 3/2008 | King |
| 2008/0058888 A1 | 3/2008 | King |
| 2008/0065158 A1 | 3/2008 | Ben-Ezra |
| 2008/0086036 A1 | 4/2008 | Hartley |
| 2008/0097539 A1 | 4/2008 | Belalcazar |
| 2008/0103570 A1 | 5/2008 | Gerber |
| 2008/0109045 A1 | 5/2008 | Gross et al. |
| 2008/0154333 A1 | 6/2008 | Knudson et al. |
| 2008/0167697 A1 | 7/2008 | Johnson |
| 2008/0183259 A1 | 7/2008 | Bly et al. |
| 2008/0234791 A1 | 9/2008 | Arie et al. |
| 2008/0269854 A1 | 10/2008 | Hegland et al. |
| 2008/0281381 A1 | 11/2008 | Gerber et al. |
| 2008/0294221 A1 | 11/2008 | Kilgore et al. |
| 2008/0319511 A1 | 12/2008 | Pless |
| 2009/0018617 A1 | 1/2009 | Skelton et al. |
| 2009/0024187 A1 | 1/2009 | Erickson et al. |
| 2009/0036945 A1 | 2/2009 | Chancellor et al. |
| 2009/0054962 A1 | 2/2009 | Lefler et al. |
| 2009/0069803 A1 | 3/2009 | Starkebaum |
| 2009/0076565 A1 | 3/2009 | Surwit |
| 2009/0112282 A1 | 4/2009 | Kast et al. |
| 2009/0118777 A1 | 5/2009 | Iki |
| 2009/0125079 A1 | 5/2009 | Armstrong et al. |
| 2009/0132010 A1 | 5/2009 | Kronberg |
| 2009/0132016 A1 | 5/2009 | Putz |
| 2009/0157141 A1 | 6/2009 | Chiao et al. |
| 2009/0157149 A1 | 6/2009 | Wahlgren et al. |
| 2009/0196472 A1 | 8/2009 | Goetz et al. |
| 2009/0198306 A1 | 8/2009 | Goetz et al. |
| 2009/0204173 A1 | 8/2009 | Fang et al. |
| 2009/0204192 A1 | 8/2009 | Carlton et al. |
| 2009/0210041 A1 | 8/2009 | Kim et al. |
| 2009/0264973 A1 | 10/2009 | Boling et al. |
| 2009/0281595 A1 | 11/2009 | King et al. |
| 2009/0287274 A1 | 11/2009 | De Ridder |
| 2009/0287279 A1 | 11/2009 | Parramon et al. |
| 2009/0326611 A1 | 12/2009 | Gillbe |
| 2010/0010567 A1 | 1/2010 | Deem et al. |
| 2010/0016929 A1 | 1/2010 | Prochazka |
| 2010/0036454 A1 | 2/2010 | Bennett et al. |
| 2010/0042193 A1 | 2/2010 | Slavin |
| 2010/0057178 A1 | 3/2010 | Simon |
| 2010/0069993 A1 | 3/2010 | Greenspan |
| 2010/0094375 A1 | 4/2010 | Donders et al. |
| 2010/0125313 A1 | 5/2010 | Lee et al. |
| 2010/0137938 A1 | 6/2010 | Kishawi et al. |
| 2010/0152817 A1 | 6/2010 | Gillbe |
| 2010/0191307 A1 | 7/2010 | Fang et al. |
| 2010/0198298 A1 | 8/2010 | Glukhovsky |
| 2010/0228325 A1 | 9/2010 | Moffitt et al. |
| 2010/0241190 A1 | 9/2010 | Kilgore et al. |
| 2010/0249875 A1 | 9/2010 | Kishawi et al. |
| 2010/0256696 A1 | 10/2010 | Schleicher et al. |
| 2010/0274312 A1 | 10/2010 | Alataris et al. |
| 2010/0274314 A1 | 10/2010 | Alataris et al. |
| 2010/0274315 A1 | 10/2010 | Alataris et al. |
| 2010/0274316 A1 | 10/2010 | Alataris et al. |
| 2010/0274317 A1 | 10/2010 | Parker et al. |
| 2010/0274318 A1 | 10/2010 | Walker et al. |
| 2010/0274320 A1 | 10/2010 | Torgerson |
| 2010/0274326 A1 | 10/2010 | Chitre et al. |

(56) References Cited

U.S. PATENT DOCUMENTS

| | | |
|---|---|---|
| 2010/0324630 A1 | 12/2010 | Lee et al. |
| 2010/0331916 A1 | 12/2010 | Parramon et al. |
| 2011/0009919 A1 | 1/2011 | Carbunaru et al. |
| 2011/0009923 A1 | 1/2011 | Lee |
| 2011/0009927 A1 | 1/2011 | Parker et al. |
| 2011/0022114 A1 | 1/2011 | Navarro |
| 2011/0184301 A1 | 7/2011 | Holmstrom et al. |
| 2011/0184486 A1 | 7/2011 | De Ridder |
| 2011/0184488 A1 | 7/2011 | De Ridder |
| 2011/0201977 A1 | 8/2011 | Tass |
| 2011/0276107 A1 | 11/2011 | Simon et al. |
| 2011/0282412 A1 | 11/2011 | Glukhovsky et al. |
| 2012/0016437 A1 | 1/2012 | Alataris et al. |
| 2012/0016438 A1 | 1/2012 | Alataris et al. |
| 2012/0016439 A1 | 1/2012 | Alataris et al. |
| 2012/0089200 A1 | 4/2012 | Ranu et al. |
| 2012/0150252 A1 | 6/2012 | Feldman et al. |
| 2012/0172946 A1 | 7/2012 | Alataris et al. |
| 2012/0203304 A1 | 8/2012 | Alataris et al. |
| 2012/0209349 A1 | 8/2012 | Alataris et al. |
| 2012/0277833 A1 | 11/2012 | Gerber et al. |
| 2012/0283797 A1 | 11/2012 | De Ridder |
| 2013/0006325 A1 | 1/2013 | Woods et al. |
| 2013/0023951 A1 | 1/2013 | Greenspan |
| 2013/0041425 A1 | 2/2013 | Fang et al. |
| 2013/0066411 A1 | 3/2013 | Thacker et al. |
| 2013/0096643 A1 | 4/2013 | Fang et al. |
| 2013/0096644 A1 | 4/2013 | Fang et al. |
| 2013/0110196 A1 | 5/2013 | Alataris et al. |
| 2013/0123879 A1 | 5/2013 | Alataris et al. |
| 2013/0172955 A1 | 7/2013 | Alataris et al. |
| 2013/0204173 A1 | 8/2013 | Kelly et al. |
| 2013/0204320 A1 | 8/2013 | Alataris et al. |
| 2013/0204321 A1 | 8/2013 | Alataris et al. |
| 2013/0204322 A1 | 8/2013 | Alataris et al. |
| 2013/0204323 A1 | 8/2013 | Thacker et al. |
| 2013/0204324 A1 | 8/2013 | Thacker et al. |
| 2013/0204338 A1 | 8/2013 | Alataris et al. |
| 2013/0211487 A1 | 8/2013 | Fang et al. |
| 2013/0237948 A1 | 9/2013 | Donders |
| 2013/0261695 A1 | 10/2013 | Thacker et al. |
| 2013/0261696 A1 | 10/2013 | Thacker et al. |
| 2013/0261697 A1 | 10/2013 | Parker |
| 2014/0031896 A1 | 1/2014 | Alataris et al. |
| 2014/0142656 A1 | 5/2014 | Alataris et al. |
| 2014/0142657 A1 | 5/2014 | Alataris et al. |
| 2014/0142658 A1 | 5/2014 | Alataris et al. |
| 2014/0142659 A1 | 5/2014 | Alataris et al. |
| 2014/0142673 A1 | 5/2014 | Alataris et al. |
| 2014/0343622 A1 | 11/2014 | Alataris et al. |
| 2014/0379044 A1 | 12/2014 | Walker et al. |
| 2015/0012079 A1 | 1/2015 | Goroszeniuk et al. |
| 2015/0018896 A1 | 1/2015 | Alataris et al. |
| 2015/0032181 A1 | 1/2015 | Baynham |
| 2015/0032182 A1 | 1/2015 | Alataris et al. |
| 2015/0032183 A1 | 1/2015 | Alataris et al. |
| 2015/0039040 A1 | 2/2015 | Alataris et al. |
| 2015/0039049 A1 | 2/2015 | Alataris et al. |
| 2015/0039050 A1 | 2/2015 | Alataris et al. |
| 2015/0045853 A1 | 2/2015 | Alataris et al. |
| 2015/0045854 A1 | 2/2015 | Alataris et al. |
| 2015/0051664 A1 | 2/2015 | Alataris et al. |
| 2015/0073510 A1 | 3/2015 | Perryman |
| 2015/0217116 A1 | 8/2015 | Parramon et al. |
| 2015/0343220 A1 | 12/2015 | Alataris et al. |
| 2016/0121119 A1 | 5/2016 | Alataris et al. |
| 2016/0287872 A1 | 10/2016 | Alataris et al. |
| 2016/0287873 A1 | 10/2016 | Alataris et al. |
| 2016/0287874 A1 | 10/2016 | Alataris et al. |
| 2016/0287875 A1 | 10/2016 | Thacker et al. |
| 2016/0287888 A1 | 10/2016 | Alataris et al. |
| 2016/0303374 A1 | 10/2016 | Alataris et al. |
| 2017/0050021 A1 | 2/2017 | Cosman, Sr. |
| 2017/0165485 A1 | 6/2017 | Sullivan et al. |

FOREIGN PATENT DOCUMENTS

| | | |
|---|---|---|
| EP | 2243511 A2 | 10/2010 |
| EP | 2396075 A1 | 12/2011 |
| EP | 2448633 A1 | 5/2012 |
| EP | 2477693 A2 | 7/2012 |
| EP | 2630984 A1 | 8/2013 |
| EP | 2403589 B1 | 1/2014 |
| EP | 2421600 B1 | 3/2014 |
| EP | 2243510 B1 | 4/2014 |
| EP | 2459271 B1 | 4/2015 |
| EP | 2451523 B1 | 5/2018 |
| GB | 2449546 A | 11/2008 |
| GB | 2499546 | 11/2008 |
| JP | 2002200179 A | 7/2002 |
| JP | 2007528774 A | 10/2007 |
| JP | 2008500086 A | 1/2008 |
| SU | 1512625 A1 | 10/1989 |
| SU | 1690727 A1 | 11/1991 |
| WO | WO-02065896 A2 | 8/2002 |
| WO | WO-02/085448 | 10/2002 |
| WO | WO-02092165 A1 | 11/2002 |
| WO | WO-03015863 A2 | 2/2003 |
| WO | WO-03066154 A2 | 8/2003 |
| WO | WO-2004007018 A1 | 1/2004 |
| WO | WO-2005115532 A2 | 12/2005 |
| WO | WO-2006007048 | 1/2006 |
| WO | WO-2006057734 A1 | 6/2006 |
| WO | WO-2006063458 | 6/2006 |
| WO | WO-2006084635 A2 | 8/2006 |
| WO | WO-2006119046 A1 | 11/2006 |
| WO | WO-2007035925 A2 | 3/2007 |
| WO | WO-2007082382 A1 | 7/2007 |
| WO | WO-2007103324 A1 | 9/2007 |
| WO | WO-2007117232 A1 | 10/2007 |
| WO | WO-2008039982 A2 | 4/2008 |
| WO | WO-2008045434 A2 | 4/2008 |
| WO | WO-2008106174 A1 | 9/2008 |
| WO | WO-2008121891 A1 | 10/2008 |
| WO | WO-2008140940 | 11/2008 |
| WO | WO-2008142402 A1 | 11/2008 |
| WO | WO-2008153726 A2 | 12/2008 |
| WO | WO-2009018518 A1 | 2/2009 |
| WO | WO-2009061813 A1 | 5/2009 |
| WO | WO-2009097224 A1 | 8/2009 |
| WO | WO-2009129329 A1 | 10/2009 |
| WO | WO-2010111358 A2 | 9/2010 |
| WO | WO 2010124139 | 10/2010 |
| WO | WO 2010124144 | 10/2010 |
| WO | WO-2011014570 A1 | 2/2011 |
| WO | WO-2012154985 | 11/2012 |
| WO | WO-2016154091 A1 | 9/2016 |
| WO | WO-2017044904 | 3/2017 |
| WO | WO-201 7146658 | 8/2017 |

OTHER PUBLICATIONS

"The Need for Mechanism-Based Medicine in Neuromodulation," Neuromodulation: Technology at the Neural Interface, 2012, 7 pages.

Abejon et al., "Is Impedance a Parameter to be Taken into Account in Spinal Cord Stimulation?" Pain Physician, 2007, 8 pages.

Acticare.com website, http://web.archive.org/web/*/acticare.com, Internet Archive Way Back Machine, 2012, 22 pages.

Additional Arguments to Notice of Opposition of European Patent No. 2853285, filed by Medtronic, Inc., on May 17, 2017, 9 pages.

Advanced Neuromodulation Systems, Compustim SCS Systems, ; Clinical Manual, 1997, 52 pages.

Agnew et al., "Considerations for safety with chronically implanted nerve electrodes," Epilepsia, 31.s2, 1990, 6 pages.

Al-Kaisy et al., "10 kHz High-Frequency Spinal Cord Stimulation for Chronic Axial Low Back Pain in Patients With No History of Spinal Surgery: A Preliminary, Prospective, Open Label and Proof-of-Concept Study," Neuromodulation: Technology at the Neural Interface, 2016, 8 pages.

Al-Kaisy et al., "Prospective, Randomized, Sham-Control, Double Blind, Crossover Trial of Subthreshold Spinal Cord Stimulation at

(56) References Cited

OTHER PUBLICATIONS

Various Kilohertz Frequencies in Subjects Suffering from Failed Back Surgery Syndrome," International Neuromodulation Society, 2018, 9 pages.
Al-Kaisy et al., "Sustained Effectiveness of 10kHz High-Frequency Spinal Cord Stimulation for Patients with Chronic, Low Back Pain: 24-month Results of Prospective Multicenter Study," Pain Medicine, 2014, 8 pages.
Al-Kaisy et al., "The Use of 10-Kilohertz Spinal Cord Stimulation in a Cohort of Patients with Chronic Neuropathic Limb Pain Refractory to Medical Management," Neuromodulation Technology at the Neural; Interface, 2015, 6 pages.
Al-Kaisy et al., Poster: "High-Frequency Spinal Cord Stimulation at 10 kHz for the Treatment of Chronic Back Pain Patients without Prior Back Surgery," 2013, 1 page.
Alo et al., "Factors Affecting Impedance of Percutaneous Leads in Spinal Cord Stimulation," International Neuromodulation Society, vol. 9, No. 2, 2006, 8 pages.
Alo et al., "New Trends in Neuromodulation for the Management of; Neuropathic Pain," Neurosurgery, vol. 50, No. 4, Apr. 2002, 15 pages.
Amendment in Response to Ex Parte Office Action for U.S. Appl. No. 13/446,970, First Named Inventor: Konstantinos Alataris, Mailed: Nov. 28, 2012, 14 pages.
Amendment in Response to Non-Final Office Action for U.S. Appl. No. 13/245,450, First Named Inventor: Konstantinos Alataris, filed Feb. 7, 2012, 15 pages.
Amendment in Response to Non-Final Office Action for U.S. Appl. No. 12/765,747, First Named Inventor: Konstantinos Alataris, dated Jan. 24, 2014, 21 pages.
Applicant-Initiated Interview Summary for U.S. Appl. No. 13/245,450, First Named Inventor: Konstantinos Alataris, dated Feb. 1, 2012, 2 pages.
Applicant-Initiated Interview Summary for U.S. Appl. No. 13/725,770, First Named Inventor: Konstantinos Alataris, dated Apr. 5, 2013, 3 pages.
Applicant-Initiated Interview Summary for U.S. Appl. No. 12/765,747, First Named Inventor: Konstantinos Alataris, dated Sep. 11, 2013, 3 pages.
Application Data Sheet for U.S. Appl. No. 13/446,970 (U.S. Pat. No. 8,359,102), First Named Inventor: Konstantinos Alataris, filed Apr. 13, 2012, 6 pages.
Augustinsson et al., "Spinal Cord Stimulation in Cardiovascular Disease," Functional Neurosurgery, vol. 6, No. 1, Jan. 1995, 10 pages.
Bara et al., Poster re: High Frequency Spinal Cord Stimulation for Dominant Back Pain—1 year follow up, 2013, 1 page.
Barolat et al., "Multifactorial Analysis of Epidural Spinal Cord Stimulation," Sterotactic and Functional Neurosurgery, 1991; 56: 77-103.
Barolat et al., "Spinal Cord Stimulation for Chronic Pain Management," Seminars in Neurosurgery, vol. 15, Nos. 2/3, 2004, 26 pages.
Barolat et al., "Surgical Management of Pain—Spinal Cord Stimulation: Equipment and Implantation Techniques," Chapter 41, Thieme Medical Publishers, New York, 2002, 11 pages.
Bennett et al., "Spinal Cord Stimulation for Complex regional pain syndrome I [RSD]: a Retrospective Multicenter Experience from 1995 to 1998 of 101 patients." Neuromodulation, vol. 2, No. 3, 1999, 9 pages.
Benyamin et al., "A Case of Spinal Cord Stimulation in Raynaud's Phenomenon: Can Subthreshold Sensory Stimulation Have an Effect?" Pain Physician www.painphysicianjournal.com, 2007, 6 pages.
Bhadra et al., "High Frequency electrical conduction block of the pudendal nerve," Journal of Neural Engineering—Institute of Physics Publishing, ; 2006, 8 pages.
Bhadra et al., Stimulation of High-Frequency Sinusoidal Electrical Block of Mammalian Myelinated Axons, J Comput Neurosco, 22:313-326, 2007.

Bhadra MD, Niloy et al., "High-Frequency Electrical Conduction Block of Mammalian Peripheral Motor Nerve," Muscle and Nerve, Dec. 2005, 9 pages.
BionicNAVIGATOR Software Guide, Part MP9055261-001, 2004, 58 pages.
Boger et al., "Bladder Voiding by Combined High Frequency Electrical Pudendal Nerve Block and Sacral Root Stimulation," Neurourology and Urodynamics, 27, 2008, 5 pages.
Boston Scientific "Precision™ Spinal Cord Stimulator System Clinician Manual—Directions for Use," 2015, 74 pages.
Boston Scientific, News Release: "New Data Presented at NANS 2014 Demonstrate Long-Term, Low Back Pain Relief with Boston Scientific Precision Spectra™ Spinal Cord Stimulator System," Dec. 12, 2014, 8 pages.
Boston Scientific's Response to the Summons to Attend Oral Proceedings for European Patent No. 2207587, *Nevro Corp.* vs. *Boston Scientific Neuromodulation Corporation*, filed Sep. 6, 2018, 31 pages.
Bowman and McNeal, Response of Single Alpha Motoneurons to High-Frequency Pulse Trains, Appl. Neurophysiol. 49, p. 121-138, 1986, 10 pages.
Bronstein et al., "The Rationale Driving the Evolution of Deep Brain Stimulation of Constant-Current Devices," International Neuromodulation Society 2014, 5 pages.
Broseta et al., "High-Frequency cervical spinal cord stimulation in spasticity and motor disorders," Advances in Stereotactic and Functional Neurosurgery 7. Springer Verlag 1987, 6 pages.
Burton, Charles, "Dorsal Column Stimulation: Optimization of Application," Surgical Neurology, vol. 4, No. 1, Jul. 1975, 10 pages.
Butt et al., "Histological Findings Using Novel Stimulation Parameters in a Caprine Model," European Journal of Pain Supplements, 2011, 2 pages.
Cahana et al., "Acute Differential Modulation of Synaptic Transmission and Cell Survival During Exposure to Pulsed and Continuous Radiofrequency; Energy," Journal of Pain, vol. 4, No. 4, May 2003, 6 pages.
Cameron et al., "Effects of posture on stimulation parameters in spinal cord stimulation," Neuromodulation: Technology at the Neural Interface 1.4, 1998, 8 pages.
Camilleri et al., "Intra-abdominal vagal blocking (VBLOC therapy): clinical results with a new implantable medical device," Surgery 143.6, 2008, 9 pages.
Capdevila et al., "Continuous Peripheral Nerve Blocks in Hospital Wards after Orthopedics Surgery," Anesthesiology 2005, 103:1035-45, 10 pages.
ClinicalTrials.gov, "Safety and Effectiveness Study of the Precision SCS System Adapted for High-Rate Spinal Cord Stimulation (ACCELERATE)," https://clinicaltrials.gov/ct2/show/NCT02093793?term=boston+scientific&recr=Open&cond=%22Pain%22&rank=3, Feb. 2015, 3 pages.
Crapanzano et al., "High Frequency Spinal Cord Stimulation for Complex Regional Pain Syndrome: A Case Report," Pain Physician, 2017, 6 pages.
Crosby et al., "Stimulation Parameters Define the Effectiveness of Burst Spinal Cord Stimulation in a Rat Model of Neuropathic Pain," Neuromodulation Technology at the Neural Interface, International Neuromodulation Society, 2014, 8 pages.
Cuellar et al., "Effect of High Frequency Alternating Current on Spinal Afferent Nociceptive Transmission," Neuromodulation: Technology at the Neural Interface, ; 2012, 10 pages.
Curriculum Vitae and Declaration of Dr. Ganesan Baranidharan on behalf of European Patent No. 2630984, 19 pages, 2016.
Curriculum Vitae and Declaration of Dr. Jonathan Miller, 42 pages, Oct. 25, 2016.
Curriculum Vitae and Declaration of Dr. Simon James Thomson on behalf of European Patent No. 2630984, Oct. 24, 2016, 13 pages.
Curriculum Vitae and Declaration of Prof. Bengt Linderoth on behalf of European Patent No. 2630984, Oct. 21, 2016, 6 pages.
Curriculum Vitae of Michael A. Moffitt, 2015, 2 pages.
Dapoigny, "Vagal influence on colonic motor activity in conscious nonhuman primates," AM Journal Physiol., 1992, 262: G231-G236.

(56) References Cited

OTHER PUBLICATIONS

De Carolis et al., Poster: "Efficacy of Spinal Cord Stimulation (SCS) in the Treatment of Failed Back Surgery Syndrome (FBSS): a comparative study," 2013, 1 page.
De Ridder et al., U.S. Appl. No. 60/895,061, Applicant: Dirk De Ridder, filed Mar. 15, 2007, 47 pages.
Decision and Minutes: Opposition of European Patent No. 2421600 by Boston Scientific Neuromodulation Corporation, Apr. 3, 2017, 28 pages.
Decision Revoking the European Patent for Opposition by Medtronic, Inc., and Boston Scientific Neuromodulation Corporation for European Patent No. 2243510, mailed Jul. 27, 2017, 37 pages.
Declaration of Cameron C. McIntyre, Ph.D., May6, 2015, Attorney Ref: 1014.0248AB1, 88 pages.
Declaration of Cameron C. McIntyre, Ph.D., May 6, 2015, Attorney Ref: 1014.0248AB2, 57 pages.
Declaration of Dr. Jonathan Miller on behalf of European Patent No. 2853285, 26 pages, May 16, 2017.
Declaration of M. Jason D. Rahn for European Patent No. 2243510, dated Feb. 2, 2017, 2 pages.
Declaration of M. Jason D. Rahn, Jan. 7, 2015, 7 pages.
Declaration of Prof. Bengt Linderoth for European Patent No. 2421600, dated Dec. 16, 2016 2 pages.
Defendant's Boston Scientific Corporation's and Boston Scientific Neuromodulation Corporation's Preliminary Invalidity Contentions, Case No. 3:16-cv-06830-VC, filed Mar. 17, 2017, 159 pages.
DeRidder et al., "Are Paresthesias necessary for pain suppression in SCS—Burst Stimulation," BRAIN, Brain Research Center Antwerp of Innovative and Interdisciplinary Neuromodulation, 2010, 27 pages.
DeRidder et al., "Burst Spinal Cord Stimulation: Toward Paresthesia-Free Pain Suppression," www.neurosurgery-online.com, vol. 66, Nos. 5, May 2010, 5 pages.
Dorland's Illustrated Medical Dictionary, Twenty-sixth Edition, "Paresthesia," 1981, 4 pages.
Doug Atkins of Medtronic Neurological, "Medtronic Neurostimulation Leads, 510(k) Summary," Submission Prepared: Feb. 27, 2004, 6 pages.
Duyvendak et al., "Spinal Cord Stimulation With a Dual Quadripolar Surgical Lead Placed in General Anesthesia is Effective in Treating Intractable Low Back and Leg Pain," Neuromodulation: Technology at the Neural Interface, vol. 10, No. 2, 2007, 7 pages.
Eddicks et al., "Thoracic Spinal Cord Stimulation Improves Functional Status and Relieves Symptoms in Patients with Refractory Angina Pectoris: The First Placebo-Controlled Randomised Study," Heart Journal, 2007, 6 pages.
Ex Parte Office Action for U.S. Appl. No. 13/446,970, First Inventor Named: Konstantinos Alataris, Mailed: Oct. 15, 2012, 9 pages.
Feeling vs. Function Poster, Mager and Associates Consulting, 2009, 1 page.
First Preliminary Amendment for U.S. Appl. No. 13/446,970, First Named Inventor: Konstantinos Alataris, Mailed: May 18, 2012, 7 pages.
Geddes, "A Short History of the electrical stimulation of excitable tissue—Including Electrotherapeutic Applications," The Physiologist, vol. 27, No. 1, Feb. 1984, 51 pages.
Grill, Warren et al., "Stimulus Waveforms for Selective Neural Stimulation," IEEE Engineering in Medicine and Biology, Jul./Aug. 1995, pp. 375-385.
Gulve et al., Poster: "10kHz High Frequency Spinal Cord Stimulation: Middlesbrough Experience," 2013, 1 page.
Guo et al., "Design and Implement of a Mini-Instrument for Rehabilitation with Transcutaneous Electrical Nerve Stimulation," School of Medical Instrument and Food Engineering, University of Shanghai for Science and Technology, Shanghai China, Mar. 31, 2007, 5 pages.
Hefferman et al., "Efficacy of Transcutaneous Spinal Electroanalgesia in Acute Postoperative Pain Management," Anesthesiology, 2001, 2 pages.

Higuchi et al., "Exposure of the Dorsal Root Ganglion in Rats to Pulsed Radiofrequency Currents Activates Dorsal Horn Lamina I and II Neurons,"; Neurosurgery, vol. 50, No. 4, Apr. 2002, 7 pages.
Hilberstadt et al., "The Effect of Transcutaneous Spinal Electroanalgesia upon Chronic Pain: A single case study," Physiotherapy, vol. 86 No. 3, Mar. 2000, 2 pages.
Holsheimer—Effectiveness of Spinal Cord Stimulation in the Management of Chronic Pain: Analysis of Technical Drawbacks and Solutions, Neurosurgery, vol. 40, No. 5, May 1997, pp. 990-999.
Hopp et al., "Effect of anodal blockade of myelinated fibers on vagal c-fiber afferents," American Journal Physiological Society, Nov. 1980; 239(5), 9 pages.
Hoppenstein, Reuben, "Electrical Stimulation of the Ventral and Dorsal cols. of the Spinal Cord for Relief of Chronic Intractable Pain: Preliminary Report," Surgical Neurology, vol. 4, No. 1, Jul. 1975, 9 pages.
House et al., "Safety and Efficacy of the House/3M Cochlear Implant in Profoundly Deaf Adults," Otolaryngologic Clinics of North America, vol. 19, No. 2, May 1986, 12 pages.
Huxely et al., "Excitation and Conduction in Nerve: Quantitative Analysis," Science, Sep. 11, 1964; 145: 1154-9.
International Neuromodulation Society 10th World Congress, Neuromodulation: Technology that Improves Patient Care, London, England, May 21-26, 2011, 385 pages.
J.P. Morgan North America Equity Research, "Nevro—Let the Launch Begin: Senza Approved, Raising PT to $54," www.jpmorganmarkets.com, May 10, 2015, 8 pages.
J.P. Morgan North America Equity Research, "Nevro—Welcome to the Future of Spinal Cord Stimulation Initiating at OW with $34 Price Target," www.jpmorganmarkets.com, Dec. 1, 2014, 39 pages.
Jacques et al., "Development of a New Implantable Bio-Telestimulator," Surg. Neurol., vol. 13, May 1980, 2 pages.
Jain et al., Abstract—"Accelerate: A Prospective Multicenter Trial Evaluating the Use of High-Rate Spinal Cord Stimulation in the Management of Chronic Intractable Pain," The American Academy of Pain Medicine, 2015, 1 page.
Jang et al., "Analysis of Failed Spinal Cord Stimulation Trails in the Treatment of Intractable Chronic Pain," J. Korean Neurosurg Soc 43, 2008, 5 pages.
Jezernik et al., "Electrical Stimulation for the Treatment of Bladder; Dysfunction: Current Status and Future Possibilities," Neurological Research, vol. 24, Jul. 2002, 18 pages.
JMP Securities, "Nevro Corp. (NVRO) Initiating Coverage on Nevro Corp. with a Market Outperform Rating—Investment Highlights," Dec. 1, 2014, 42 pages.
Kapural et al., "Comparison of 10-kHz High Frequency and Traditional Low-Frequency Spinal Cord Stimulation for the Treatment of Chronic Back ; and Leg Pain: 24-Month Results From a Multicenter, Randomized, Controlled Pivotal Trial," Neurosurgery, vol. 79, No. 5, Nov. 2016, 11 pages.
Kapural et al., "Novel 10-Khz High Frequency Therapy (HF10 Therapy) is Superior to Traditional Low-Frequency Spinal Cord Stimulation for Treatment of Chronic Back and Leg Pain," Anesthesiology The Journal of American Society of Anesthesiologists, Inc., 2015, 11 pages.
Kilgore et al. "Nerve Conduction Block Utilizing High-Frequency Alternating Current" Medical & Biology Engineering and Computing, 2004, vol. 24, pp. 394-406.
Kilgore et al. "Reversible Nerve Conduction Block Using Kilohertz Frequency Alternating Current," Neuromodulation Technology at the Neural Interface, International Neuromodulation Society, 2013, 13 pages.
Kreitler et al., "Chapter 15: Implantable Devices and Drug Delivery Systems—The Handbook for Chronic Pain," NOVA Biomedical Books, New York, ; 2007, 17 pages.
Krista Oakes of Neuromed, Inc., "Implanted Spinal Cord Stimulator Lead 510(k) Summary of Safety and Effectiveness," Submission Prepared Feb. 21, 1996, 3 pages.
Kuechmann et al., Abstract #853: "Could Automatic Position Adaptive Stimulation Be Useful in Spinal Cord Stimulation?" Medtronic, Inc., Minneapolis, MN, European Journal of Pain 13, 2009, 1 page.

(56) References Cited

OTHER PUBLICATIONS

Kumar et al., "Spinal Cord Stimulation in Treatment of Chronic Benign Pain: Challenges in Treatment Planning and Present Status, a 22-Year Experience," Neurosurgery, vol. 58, No. 3, Mar. 2006, 16 pages.
Kumar et al., "The Effects of Spinal Cord Stimulation in Neuropathic Pain Are Sustained: A 24-month Follow-Up of the Prospective Randomized Controlled Multicenter Trial of the Effectiveness of Spinal Cord Stimulation," www.neurosurgery-online.com, vol. 63, No. 4, Oct. 2008, 9 pages.
Lambru et al., "Safety and Efficacy of Cervical 10 kHz Spinal Cord Stimulation in Chronic Refractory Primary Headaches: A Retrospective Case Series," The Journal of Headache and Pain, 2016, 8 pages.
Lempka et al., "Computational Analysis of Kilohertz Frequency Spinal Cord Stimulation for Chronic Pain Management," Anesthesiology, vol. 122, No. 6, Jun. 2015, 15 pages.
Linderoth et al., "Mechanisms of Spinal Cord Stimulation in Neuropathic and Ischemic Pain Syndromes," Neuromodulation, Chapter 25, 2009, 19 pages.
Linderoth et al., "Mechanisms of Spinal Cord Stimulation in Painful Syndromes: Role of Animal Models," Pain Medicine, vol. 7, No. S1, 2006, 13 pages.
Linderoth et al., "Physiology of Spinal Cord Stimulation: Review and Update," Neuromodulation, vol. 2, No. 3, 1999, 15 pages.
MacDonald, Alexander J. R, and Coates, Tim W., "The Discovery of Transcutaneous Spinal Electroanalgesia and Its Relief of Chronic Pain," Physiotherapy, vol. 81. No. 11, Nov. 1995, 9 pages.
Manola et al., "Technical Performance of Percutaneous Leads for Spinal Cord Stimulation: A Modeling Study," International Neuromodulation Society, 2005, 12 pages.
Mavoori et al., "An Autonomous implantable computer for neural recording and stimulation in unrestrained primates," Journal of Neuroscience Methods, 2005, 7 pages.
McCreery et al., "Charge Density and Charge Per Phase as Cofactors in Neural Injury Induced by Electrical Stimulation," IEEE Transactions on Biomedical Engineering, vol. 37, No. 10, Oct. 1990.
McCreery et al., "Damage in Peripheral Nerve from Continuous Electrical Stimulation: Comparison of Two Stimulus Waveforms," Medical and Biological Engineering and Computing, Jan. 1992, 6 pages.
McCreery et al., "Relationship between Stimulus Amplitude, Stimulus Frequency and Neural Damage During Electrical Stimulation of Sciatic Nerve of a Cat," Medical and Biological Engineering and Computing, May 1995, 4 pages.
Mediati, R.D., Mechanisms of Spinal Cord Stimulation, Florence Oct. 2, 2002.
Medtronic—Neurological Division, QuadPlus, Model 3888, Lead Kit for Spinal Cord Stimulation (SCS) Implant Manual, 1996, 33 pages.
Medtronic—Neurological Division, Resume II, Model 3587A, Lead Kit for Spinal Cord Stimulation (SCS) and Peripheral Nerve Stimulation (PNS), Implant Manual, 1996, 32 pages.
Medtronic—Neurological Division, Resume TL, Model 3986, Lead Kit for Spinal Cord Stimulation (SCS) and Peripheral Nerve Stimulation (PNS), Implant Manual, 1996, 27 pages.
Medtronic—Neurostimulation Systems: Expanding the Array of Pain Control Solutions, 1999, 6 pages.
Medtronic commercial leaflet entitled: Surgical Lead Comparison, 1999, 4 pages.
Medtronic, "Medtronic Pain Therapy—Using Neurostimulation for Chronic Pain, Information for Prescribers" 2007, 29 pages.
Medtronic, Pain Therapy Product Guide, Dec. 2008, 31 pages.
Medtronic, Pisces Quad 3487A, Pisces Quad Compact model 3887, Pisces Quad Plus 3888 Lead Kit, Implant Manual, 2008, 16 pages.
Medtronic: Spinal Cord Stimulation Systems, 2013, 4 pages.
Melzack, Ronald et al., "Pain Mechanisms: A New Theory," Science, vol. 150, No. 3699, Nov. 19, 1965, 9 pages.

Merriam Webster's Collegiate Dictionary, Tenth Edition, definition of "Implantable," 1995, 3 pages.
Meyerson et al., Mechanisms of spinal cord stimulation in neuropathic pain, Neurological Research, vol. 22, Apr. 2000, 5 pages.
Miller, Jonathan, "Neurosurgery Survival Guide—A Comprehensive Guide to Neurosurgical Diagnosis and Treatment," http://d3jonline.tripod.com/neurosurgery/, Nov. 14, 2016, 4 pages.
Miller, Jonathan, "Parameters of Spinal Cord Stimulation and Their Role in Electrical Charge Delivery: A Review," Neuromodulation: Technology at the Neural Interface, 2016.
Morgan Stanley Research North America, "Nevro Corp—There's Something Happening Here," Dec. 15, 2014, 12 pages.
Mosby's Medical Dictionary, 8th Edition, "Paresthesia," 2009, 3 pages.
Mounaïm et al., "New Neurostimulation Strategy and Corresponding Implantable Device to Enhance Bladder Functions," Biomedical Engineering Trends in Electronics, Communications and Software, Chapter 5, 2011, 15 pages.
Mueller et al., "The MED-EL SONATATI 100 Cochlear Implant: An evaluation of its safety in adults and children," Acta Oto-Laryngologica, vol. 131, No. 5, 2011, 8 pages.
Munglani, Rajesh, "The Longer Term Effect of Pulsed Radiofrequency for Neuropathic Pain," PAIN 80, 1999, 3 pages.
Nashold et al., "Dorsal Column Stimulation for Control Pain—Preliminary Report on 30 Patients," J. Neurosurg., vol. 36, May 1972, 8 pages.
Nevro—Chronic Pain and Treatments, http://www.nevro.com/English/Patients/Chronic-Pain-and-Treatments/default.aspx; 2016, 3 pages.
Nevro—Clinical Evidence, www.nevro.com/English/Physicians/Clinical-Evidence/default.aspx, 2016, 2 pages.
Nevro—HF10™ Therapy Fact Sheet, http://www.nevro.com/English/Newsroom/Resources/default.aspx, 2015, 4 pages.
Nevro—Leadership Through Innovation, J. P. Morgan 36th Annual Healthcare Conference, Jan. 8, 2018, 21 pages.
Nevro—Physician Overview www.nevro.com/English/Physicians/Physician-Overview/default.aspx, 2016, 5 pages.
Nevro—Senza System http://www.nevro.com/English/Physicians/Senza-System/default.aspx, 2016, 3 pages.
Nevro HF10 Therapy—New Hope for Chronic Back Pain and Leg Pain Sufferers, http://s21.q4cdn.com/478267292/files/doc_downloads/HF10-Therapy-New-Hope-for-Chronic-Pain.pdf, 2016, 2 pages.
Nevro Observations and Response to Notice of Oppositions filed by Medtronic Inc., and Boston Scientific for European Patent No. 2207587, mailed Aug. 26, 2016, 16 pages.
Nevro Observations and Response to Notice of Oppositions filed by Medtronic Inc., and Boston Scientific for European Patent No. 2586488, mailed May 18, 2018, 87 pages.
Nevro Response to Notice of Oppositions filed by Boston Scientific for European Patent No. 2421600, mailed Jul. 22, 2015, 16 pages.
Nevro Response to Notice of Oppositions filed by Medtronic and Boston Scientific for European Patent No. 2630984, mailed Dec. 7, 2015, 26 pages.
Nevro Response to Notice of Oppositions filed by Medtronic, Inc., and Boston Scientific Neuromodulation Corporation for European Patent No. 2207587, filed Aug. 26, 2016, 16 pages.
Nevro Response to Notice of Oppositions filed by Medtronic, Inc., and Boston Scientific Neuromodulation Corporation for European Patent No. 2630984, filed Dec. 7, 2015, 26 pages.
Nevro Response to Notice of Oppositions filed by Medtronic, Inc., and Boston Scientific Neuromodulation Corporation for European Patent No. 2853285, filed Nov. 3, 2017, 30 pages.
Nevro Response to Opposition of Division's Comments and Summons to Oral Proceedings for European Patent No. 2630984, mailed Oct. 25, 2016, 8 pages.
Nevro Senza Patient Manual, Jan. 16, 2015, 53 pages.
Nevro Senza Physician Implant Manual, Jan. 16, 2015, 31 pages.
Nevro website: HF10 Therapy Advantages, www.nevro.com/English/Patients/HF10-Therapy-Advantages/default.aspx, 2016, 3 pages.
Nevro Written Submission to Summons to Oral Proceedings for European Patent No. 2243510, filed Sep. 8, 2016, 8 pages.
Nevro Written Submissions and Response to Notice of Oppositions filed by Medtronic Inc., and Boston Scientific for European Patent No. 2243510, mailed Aug. 28, 2015, 17 pages.

(56) References Cited

OTHER PUBLICATIONS

Nevro Written Submissions for European Patent No. 2207587, Opponents: Medtronic Inc., and Boston Scientific Neuromodulation Corporation, mailed Jul. 24, 2018, 9 pages.
Nevro, PMA Approval Letter and Referenced Summary of Safety and Effectiveness Data (SSED) May 8, 2015, 60 pages.
Nevro's Notice of Appeal for Opposition by Medtronic, Inc., and Boston Scientific Neuromodulation Corporation for European Patent No. 2243510, mailed Aug. 3, 2017, 1 page.
Nevro's Response to Preliminary Opinion for Opposition by Medtronic, Inc., and Boston Scientific Neuromodulation Corporation for European Patent No. 2243510, mailed Feb. 3, 2017, 36 pages.
Nevro's presentation of HF10 therapy on Nevro's website, http://www.nevro.com/English/Home/default.aspx, 2016, 2 pages.
Nevro's Reply of the Patentee to the Notices of Opposition filed by Medtronic, Inc., and Boston Scientific Neuromodulation Corporation for EP2853285, filed Nov. 3, 2017, 34 pages.
Nevro's Response to Further Submission by Medtronic, Inc., and Boston Scientific Neuromodulation Corporation for European Patent No. 2243510, mailed Feb. 24, 2017, 9 pages.
Nevros Response to Opponent Submission of Declaration of Jonathan Miller in European Patent No. 2630984, mailed Nov. 18, 2016, 4 pages.
Nevro's Statement of Grounds of Appeal for EP2243510 (Appeal No. T 17484/17-3.4.01), filed Nov. 30, 2017, 16 pages.
News Release Details, "Nevro Corp. Announces Pricing of Initial Public Offering," 2014, 1 page.
NIDCD-NIH 2011, Cochlear Implant Brochure, http://www.nidcd.nih.gov/health/hearing/pages/coch.aspx, Jun. 29, 2012, 2 pages.
Non-Final Office Action for U.S. Appl. No. 12/765,747, First Named Inventor: Konstantinos Alataris, dated Jul. 25, 2013, 7 pages.
Non-Final Office Acton for U.S. Appl. No. 13/245,450, First Named Inventor: Konstantinos Alataris, dated Nov. 18, 2011, 11 pages.
North American Neuromodulation Society—14th Annual Meeting, "Neuromodulation: Vision 2010," Dec. 2-5, 2010, 9 pages.
North American Neuromodulation Society—16th Annual Meeting, "From Innovation to Reality Syllabus," Dec. 6-9, 2012, 198 pages.
North American Neuromodulation Society—Celebrating 20 years, 18th Annual Meeting Program Book, Dec. 11-14, 2014, 28 pages.
North American Neuromodulation Society, "Today's Vision, Tomorrow's Reality—17th Annual Meeting," Dec. 5-8, 2013, 12 pages.
North American Neuromodulation, "15th Annual Meeting, Our Crystal Anniversary," Dec. 8-11, 2011, 8 pages.
North et al., "Failed Back Surgery Syndrome: 5-year Follow-Up after Spinal; Cord Stimulator Implantation," Neurosurgery, Official Journal of the; Congress of Neurological Surgeons, vol. 28, No. 5, May 1991, 9 pages.
North et al., "Spinal Cord Stimulation for Axial Low Back Pain," SPINE, vol. 30, No. 12, 2005, 7 pages.
North et al., "Spinal Cord Stimulation for Chronic, Intractable Pain: Experience over Two Decades," Neurosurgery, vol. 32, No. 2, Mar. 1993, 12 pages.
North et al., "Spinal Cord Stimulation With Interleaved Pulses: A Randomized, Controlled Trial," vol. 10, No. 4, 2007, 9 pages.
Notice of Allowance for U.S. Appl. No. 13/245,450, First Named Inventor: Konstantinos Alataris, dated Mar. 14, 2012, 8 pages.
Notice of Opposition for European Patent No. 3156099, Proprietor of the Patent: Nevro Corporation; Opponent: Boston Scientific Neuromodulation Corporation, Dec. 15, 2017, 27 pages.
Notice of Opposition to a European Patent for European Patent No. 2586488, Proprietor of the Patent: Nevro Corporation; Opponent: Medtronic, Inc., Mar. 15, 2017, 7 pages.
Notice of Opposition to a European Patent for European Patent No. 2853285, Proprietor of the Patent: Nevro Corporation; Opponent: Medtronic, Inc., Apr. 19, 2017, 40 pages.
Notice of Opposition to a European Patent for European Patent No. 2853285, Proprietor of the Patent: Nevro Corporation; Opponent: Boston Scientific Neuromodulation Corporation, May 16, 2017, 18 pages.

Notice of Opposition to a European Patent, Argument and Facts for European Patent No. 2630984, Proprietor of the Patent: Nevro Corporation; Opponent: Medtronic, Mar. 17, 2015, 17 pages.
Notice of Opposition to a European Patent, Argument and Facts, and Annex for European Patent No. 2630984, Proprietor of the Patent: Nevro Corporation; Opponent: Boston Scientific Neuromodulation Corporation, Mar. 17, 2015, 21 pages.
Notice of Opposition to a European Patent, Argument and Facts, and Annex for European Patent No. 2421600, Proprietor of the Patent: Nevro Corporation; Opponent: Boston Scientific Neuromodulation Corporation, Dec. 4, 2014, 22 pages.
Notice of Opposition to a European Patent, Argument and Facts, for European Patent No. 2243510, Proprietor of the Patent: Nevro Corporation, Opponent: Medtronic, Jan. 8, 2015, 22 pages.
Notice of Opposition to a European Patent, Argument and Facts, and Annex for European Patent No. 2243510, Proprietor of the Patent: Nevro Corporation; Opponent: Boston Scientific Neuromodulation Corporation, Jan. 8, 2015, 28 pages.
Notice of Opposition to a European Patent, Argument and Facts, for European Patent No. 2207587, Proprietor of the Patent: Nevro Corporation; Opponent: Medtronic, Inc., Jan. 12, 2016, 22 pages.
Notice of Opposition to a European Patent, Argument and Facts, for European Patent No. 2207587, Proprietor of the Patent: Nevro Corporation; Opponent: Boston Scientific Neuromodulation Corporation, Jan. 8, 2016, 17 pages.
Notice of Opposition to a European Patent, Argument and Facts, for European Patent No. 2586488, Proprietor of the Patent: Nevro Corporation Opponent: Boston Scientific Neuromodulation Corporation, Dec. 15, 2017, 35 pages.
Oakley et al., "A New Spinal Cord Stimulation System Effectively Relieves Chronic, Intractable Pain: A Multicenter Prospective Clinical Study," Neuromodulation: Technology at the Neural Interface, vol. 10, No. 3, 2007, 17 pages.
Oakley et al., "Spinal Cord Stimulation in Axial Low Back Pain: Solving the Dilemma," Pain Medicine, vol. 7, No. S1, 2006, 6 pages.
Oakley, John C., "Spinal Cord Stimulation Mechanisms of Action," SPINE vol. 27, No. 22, copyright 2002, 10 pages.
OHSIPP Summer Newsletter, The Official Newsletter for the Ohio Society of Interventional Pain Physicians, vol. 1 Ed. 2, Summer 2010, 8 pages.
Opponent Boston Scientific: Response to Attend Oral Proceedings for European Patent No. 2630984, mailed Oct. 25, 2016, 21 pages.
Opponent Response to Patent Proprietor Comments to Declaration of Dr. Jonathan Miller for European Patent No. 2630984, mailed Nov. 22, 2016, 3 pages.
Opponents Boston Scientific Neuromodulation Corp.: Additional Observations in view of Oral Proceedings for European Patent No. 2243510, mailed Feb. 3, 2017, 8 pages.
Opponents Boston Scientific Neuromodulation Corporation: Response to Appeal in Opposition for European Patent No. 2243510, mailed May 2, 2018, 31 pages.
Opponents Boston Scientific Neuromodulation Corporation: Response to Nov. 9, 2017 Brief Communication in Opposition for European Patent No. 2853285, mailed Feb. 13, 2018, 9 pages.
Opponents Boston Scientific: Response to Summons to Attend Oral Proceedings for European Patent No. 2421600, mailed Jan. 2, 2017, 15 pages.
Opponents Medtronic, Inc.: Additional Observations in view of Oral Proceedings for European Patent No. 2243510, mailed Feb. 3, 2017, 10 pages.
Opponents Medtronic, Inc.: Facts and Arguments in Support of Opposition for European Patent No. 2586488, mailed Dec. 15, 2017, 18 pages.
Opponents Medtronic, Inc.: Response to Appeal in Opposition for European Patent No. 2243510, mailed Apr. 30, 2018, 23 pages.
Opponents Medtronic, Inc.: Response to Attend Oral Proceedings for European Patent No. 2630984, mailed Oct. 25, 2016, 26 pages.
Opponents Medtronic: Response to Nevro Requests and Submission for European Patent No. 22453510, mailed Mar. 29, 2017, 3 pages.
Opponents Response to Patentee's (Nevro) Written Submissions for European Patent No. 2243510, mailed Feb. 22, 2016, 21 pages.

(56) References Cited

OTHER PUBLICATIONS

Paicius et al., "Peripheral Nerve Field Stimulation for the Treatment of Chronic Low Back Pain: Preliminary Results of Long-Term Follow-up: A Case Series," Neuromodulation: Technology at the Neural Interface, vol. 10, Nos. 2007, 12 pages.
Palmer et al., "Transcutaneous electrical nerve stimulation and transcutaneous spinal electroanalgesia: A preliminary efficacy and mechanisms-based investigation," Physiotherapy, 95, 2009, 7 pages.
Patent Owner's Preliminary Response for Inter Partes Review for U.S. Pat. No. 8,359,102, Case No. IPR2015-01203, Petitioner: Boston Scientific Neuromodulation Corporation, Patent Owner: Nevro Corporation, mailed Sep. 1, 2015, 70 pages.
Patent Owner's Preliminary Response for Inter Partes Review for U.S. Pat. No. 8,359,102, Case No. IPR2015-01204, Petitioner: Boston Scientific Neuromodulation Corporation, Patent Owner: Nevro Corporation, mailed Sep. 1, 2015, 63 pages.
Paterson CA et al., "Determinants of Occurrence and vol. of Transpyloric Flow During Gastric Emptying of Liquids in Dogs: Importance of Vagal Input," Dig Dis Sci, 2000, 45: 1509-1516.
Perruchoud et al., "Analgesic Efficacy of High-Frequency Spinal Cord Stimulation: A Randomized Double-Blind Placebo-Controlled Study," Neuromodulation: Technology at Neural Interface, International Neuromodulation Society, 2013, 7 pages.
Petition for Inter Partes Review of Claims 1, 2, 11-15, 17-23, 25 and 26 for U.S. Pat. No. 8,359,102, Petitioner: Boston Scientific Neuromodulation Corporation, Patent Owner: Nevro Corporation, Attorney Ref: 1014.0248AB2, May 14, 2015, 45 pages.
Petition for Inter Partes Review of Claims 1, 2, 11-15, 17-23, 25 and 26 for U.S. Pat. No. 8,359,102, Petitioner: Boston Scientific Neuromodulation Corporation, Patent Owner: Nevro Corporation, Attorney Ref: 1014.0248AB1, May 14, 2015, 67 pages.
Petrofsky et al. "Impact of Recruitment Order on Electrode Design for Neural Prosthetics of Skeletal Muscle," AM Journal of Physical Medicine, 1981, vol. 60, No. 5, pp. 243-253.
Prausnitz et al., "The Effects of Electric Current Applied to Skin: A Review for Transdermal Drug Delivery," Advanced Drug Delivery Reviews 18, 1996, 31 pages.
Precision—Physician System Handbook, Advanced Bionic Corporation, Part 9055253-0001, 2005, 92 pages.
Precision—Physician Trail Kit Insert, Advanced Bionic Corporation, Part 9055258-0001, 2005, 2 pages.
Precision Spinal Cord Stimulation—Charging System Insert, Advanced Bionic Corporation, Part 9055074-0001, 2004, 2 pages.
Precision Spinal Cord Stimulation—Charging System, Advanced Bionic Corporation, Part 9055259-0001, 2004, 2 pages.
Precision Spinal Cord Stimulation—Patient System Handbook, Advanced Bionic Corporation, Part 9055072-0001, 2004, 93 pages.
Precision Spinal Cord Stimulation—Patient Trial Journal, Advanced Bionic Corporation, Part 9055260-0001, 2004, 10 pages.
Precision Spinal Cord Stimulation—Physician Implant Manual, Advanced Bionic Corporation, Part 9055100, 2004, 62 pages.
Precision Spinal Cord Stimulation—Physician Implant Manual, Advanced Bionic Corporation, Part 9055255-0001, 2005, 70 pages.
Precision Spinal Cord Stimulation—Physician Lead Manual, Advanced Bionic Corporation, Part No. 9055183-001, May 2004, 31 pages.
Precision Spinal Cord Stimulation—Physician Lead Manual, Advanced Bionic Corporation, Part 9055095, 2004, 62 pages.
Precision Spinal Cord Stimulation—Physician Lead Manual, Advanced Bionic Corporation, Part 9055256-0001, 2005, 56 pages.
Precision Spinal Cord Stimulation—Physician Trail Handbook, Advanced Bionic Corporation, Part 9055254-0001, 2005, 66 pages.
Precision Spinal Cord Stimulation—Physician Trail Kit Model SC-7005, Part 9055066-001, Advanced Bionic Corporation, 2004, 2 pages.
Precision Spinal Cord Stimulation—Remote Control Model SC-5200, Part 9055107-001, 2004, Advanced Bionic Corporation, 2 page.s.
Precision Spinal Cord Stimulation—Remote Control Model SC-5210, Advanced Bionic Corporation, Part 9055257-001, 2005, 2 pages.
Precision Spinal Cord Stimulation System—Patient System Handbook, Advanced Bionic Corporation, Part No. 9055184-001, May 2004, 86 pages.
Precision Spinal Cord Stimulation System, Patient Trial Handbook, Part 9055078, 2004, 74 pages.
Provision of Minutes in accordance with Rule 124(4) EPC for Opposition by Medtronic, Inc., and Boston Scientific Neuromodulation Corporation for European Patent No. 2243510, mailed Jul. 27, 2017, 23 pages.
Pudenz et al., "Development of an Implantable Telestimulator," Proc. 4th Ann. Nat'l Conf. Neuroelectric Soc., Mar. 10-12, 1971, 111-12 (Wulfsohn, Norman L. and Anthony Sances, Jr. (eds.) 1971, 4 pages.
Pudenz et al., "Neural Stimulation: Clinical and Laboratory Experiences," Surg. Neurol, 39: 1993, 8 pages.
Rapcan et al., Clinical Study, "High-Frequency—Spinal Cord Stimulation," Indexed and Abstracted in Science Citation Index Expanded and in Journal Citation Reports, 2015, 3 pages.
Reddy et al., "Comparison of Conventional and Kilohertz Frequency Epidural Stimulation in Patients Undergoing Trailing for Spinal Cord Stimulation: Clinical Considerations," World Neurosurgery, www.sciencedirect.com, 6 pages, 2015.
Remedi Pain Relief—ENM (Electronic Nerve Modulation), https://web.archive.org/web/20050906181041/http://www.remediuk.com/trials.htm, 2005, 5 pages.
Renew Neurostimulation System—Clinician's Manual—Advanced Neuromodulation Systems, Life Gets Better, 2000, 77 pages.
Resume of Jason D. Rahn, Jan. 7, 2015, 2 pages.
Robb et al., "Transcutaneous Electrical Nerve Stimulation vs. Transcutaneous Spinal Electroanalgesia for Chronic Pain Associated with ; Breast Cancer Treatments," Journal of Pain and Symptom Management, vol. 33, No. 4, Apr. 2007, 10 pages.
Rosenblueth et al., "The Blocking and Deblocking Effects of Alternating Currents on Nerve," Department of Physiology in Harvard Medical School, Nov. 1938, 13 pages.
Royle, John., "Transcutaneous Spinal Electroanalgesia and Chronic Pain," Physiotherapy, vol. 86, No. 5, May 2000, 1 page.
Schulman et al., "Battery Powered BION FES Network," Proceedings of the 26th Annual Conference of the IEEE EMBS, San Francisco, CA., Sep. 1-5, 2004, 4 pages.
Science Daily, "Chronic Pain Costs U.S. up to $635 billion, study shows," www.sciencedaily.com/releases/2012/09/120911091100.htm, Sep. 11, 2012, 2 pages.
Senza Spinal Cord Stimulation (SCS) System—P130022, http://www.fda.gov/MedicalDevices/ProductsandMedicalProcedures/DeviceApprovalsandClearances/Recently-ApprovedDevices/ucm449963.htm Oct. 14, 2016, 2 pages.
Sharan et al., "Evolving Patterns of Spinal Cord Stimulation in Patients Implanted for Intractable Low Back and Leg Pain," International Neuromodulation Society, vol. 5, No. 3, 2002, 13 pages.
Shealy et al., "Dorsal Column Electrohypalgesia," Jul. 1969, 8 pages.
Shealy MD, C. Norman et al., "Electrical Inhibition of Pain by Stimulation of the Dorsal Columns: Preliminary Clinical Report," Anesthesia and Analgesia Current Researches, vol. 446, No. 4, Jul.-Aug. 1967, 3 pages.
Shelden et al., "Depolarization in the Treatment of Trigeminal Neuralgia," Evaluation of Compression and Electrical Methods; Clinical Concept of Neurophysiological Mechanism, 1966, 8 pages.
Shelden et al., "Development and Clinical Capabilities of a New Implantable Biostimulator," The American J. of Surgery, vol. 124, Aug. 1972, 6 pages.
Shelden et al., Electrical Control of Facial Pain, Am. J. of Surgery, vol. 114, Aug. 1967, 6 pages.
Shelden et al., "Electrical stimulation of the nervous system," Surg. Neurol. vol. 4, No. 1, Jul. 1975, 6 pages.
Simpson et al., "A Randomized, Double-Blind, Crossover Study of the Use of Transcutaneous Spinal Electroanalgesia in Patients with Pain from Chronic Critical Limb Ischemia," Journal of Pain and Symptom ; Management, vol. 28, No. 5, Nov. 2004, 6 pages.
Simpson, BA, "Spinal Cord Stimulation in 60 cases of Intractable Pain." Journal of Neurology, Neurosurgery and Psychiatry, 1991; 54 pp. 196-199.

(56) References Cited

OTHER PUBLICATIONS

Simpson, BA, "Spinal Cord Stimulation." British Journal of Neurosurgery, 1997, Feb. 11 (1), 5-11, 7 pages.
Sluijter et al., "The Effects of Pulsed Radiofrequency Fields Applied to the Dorsal Root Ganglion—A Preliminary Report," The Pain Clinic, vol. 11, No. 2, 1998, 12 pages.
Smet et al., "Successful Treatment of Low Back Pain with a Novel Neuromodulation Device," AZ Nikolaas, 2010, 12 pages.
Smet et al., Poster: "High-Frequency Spinal Cord Stimulation at 10 kHz after Failed Traditional Spinal Cord Stimulation," NANS, 2013, 1 page.
Solomonow et al., "Control of Muscle Contractile Force through Indirect High-Frequency Stimulation," AM Journal of Physical Medicine, 1983, vol. 62, No. 3, pp. 71-82.
St. Jude Medical, "Clinician's Manual—Percutaneous Lead Kit, Models 3143, 3146, 3149, 3153, 3156, 3159, 3183, 3186, 3189," 2016, 24 pages.
St. Jude Medical, "Eon Mini™ Rechargeable IPG," Apr. 29, 2013, 3 pages.
St. Jude Medical, "Individualized Therapy through Diverse Lead Options," 2008, 6 pages.
Statement of Grounds of Appeal for the Opposition of European Patent No. 2421600 (Appeal No. T1450/17-3.4.01) by Boston Scientific Neuromodulation Corporation, Aug. 14, 2017, 17 pages.
Stimwave, News Release: "Stimwave Receives FDA Approval for High Frequency IDE," http://stimwave.com/newsroom/latest-news, Jun. 9, 2015, 2 pages.
Struijk et al., "Recruitment of Dorsal col. Fibers in Spinal Cord Stimulation: Influence of Collateral Branching," IEEE Transactions on Biomedical Engineering, vol. 39, No. 9, Sep. 1992, 10 pages.
Summons to Attend Oral Proceedings pursuant to Rule 115(1) EPC for European Patent No. 2207587, Applicant: Nevro Corporation, mailed Mar. 9, 2018, 15 pages.
Sweet et al., "Paresthesia-Free High Density Spinal Cord Stimulation for Postlaminectomy Syndrome in a Prescreened Population: A Prospective Case Series," Neuromodulation: Technology at the Neural Interface, 2015, 7 pages.
Swigris et al., "Implantable Spinal Cord Stimulator to Treat the Ischemic Manifestations of Thromboangiitis Obliterans (Buerger's disease)," Journal of Vascular Surgery, vol. 29, No. 5, 1998, 8 pages.
Tan et al., "Intensity Modulation: A Novel Approach to Percept Control in Spinal Cord Stimulation," Neuromodulation Technology at the Neural Interface, International Neuromodulation Society 2015, 6 pages.
Taylor et al., "The Cost Effectiveness of Spinal Cord Stimulation in the Treatment of Pain: A Systematic Review of the Literature," Journal of Pain and Symptom Management, vol. 27, No. 4., Apr. 2001, 9 pages.
Tesfaye et al., "Electrical Spinal Cord Stimulation for Painful Diabetic Peripheral Neuropathy," The Lancet, vol. 348, Dec. 21-28, 1996, 4 pages.
Thompson et al., "A double blind randomised controlled clinical trial on the effect of transcutaneous spinal electroanalgesia (TSE) on low back pain," European Journal of Pain, vol. 12, Issue 3, Apr. 2008, 6 pages.
Thomson et al., "Effects of Rate on Analgesia in Kilohertz Frequency Spinal Cord Stimulation: Results of the PROCO Randomized Controlled Trial," Neuromodulation: Technology at the Neural Interface, 2017, 10 pages.
Tiede et al., "Novel Spinal Cord Stimulation Parameters in Patients with Predominate Back Pain," Neuromodulation: Technology at the Neural Interface, 2013, 6 pages.
Tollison et al., "Practical Pain Management; Neurostimulation Techniques," Chapter 12, Lippincott Williams and Wilkins, Third Edition, 2002, 13 pages.
Towell et al., "High Frequency non-invasive stimulation over the spine: Effects on mood and mechanical pain tolerance in normal subjects," Behavioral Neurology, vol. 10, 1997, 6 pages.
Urban et al., "Percutaneous epidural stimulation of the spinal cord for relief of pain—Long Term Results," Journal of Neurosurgery, vol. 48, Mar. 1978, 7 pages.
Vadalouca et al., "Therapeutic Management of Chronic Neuropathic Pain: An Examination of Pharmacologic Treatment," Annals New York Academy of Sciences, 2006, pp. 164-186.
Van Butyen et al., "High Frequency Spinal Cord Stimulation for the Treatment of Chronic Back Pain Patients: Results of a Prospective Multicenter European Clinical Study," Neuromodulation Technology at the Neural Interface, International Neuromodulation Society, 2012, 8 pages.
Van Buyten et al., "Pain Relief for Axial Back Pain Patients," INS Meeting; Poster, May 2011, 1 page.
Van Den Honert et al. "Generation of Unidirectionally Propagated Action Potentials Nerve by Brief Stimuli" Science, vol. 26, pp. 1311-1312.
Van Den Honert, Mortimer JT, "A Technique for Collison Block of Peripheral Nerve: Frequency Dependence," MP-11 IEEE Trans. Biomed, Eng. 28: 379-382, 1981.
Van Havenbergh et al., "Spinal Cord Stimulation for the Treatment of Chronic Back Pain Patients: 500-Hz vs. 1000-Hz Burst Stimulation," Neuromodulation: Technology at the Neural Interface, International Neurmodulation Society, 2014, 4 pages.
Verrills et al., "Peripheral Nerve Field Stimulation for Chronic Pain: 100 Cases and Review of the Literature," Pain Medicine, 2011, 11 pages.
Verrills et al., "Salvaging Failed Neuromodulation Implants with Nevro High Frequency Spinal Cord System," NANS Poster, 2013, 1 page.
Von Korff et al., "Assessing Global Pain Severity by Self-Report in Clinical and Health Services Research," SPINE, vol. 25, No. 24, 2000, 12 pages.
Wallace et al., Poster: "Accelerate: A Prospective Multicenter Trial Evaluating the Use of High-Rate Spinal Cord Stimulation in the Management of Chronic Intractable Pain," Boston Scientific Corporation, 2015, 1 page.
Ward et al., "Electrical Stimulation Using Kilohertz-Frequency Alternating Current," Journal of the American Physical Therapy Association, vol. 89, No. 2, Feb. 2009, 12 pages.
Ward et al., "Variation in Motor Threshold with Frequency Using kHz Frequency Alternating Current," Muscle and Nerve, Oct. 2001, 9 pages.
Webster's Third New International Dictionary of the English Language Unabridged, "Paresthesia," 1993, 3 pages.
Weinberg et al., "Increasing the oscillation frequency of strong magnetic fields above 101 kHz significantly raises peripheral nerve excitation thresholds," Medical Physics Letter, May 2012, 6 pages.
Wesselink et al., Analysis of Current Density and Related Parameters in Spinal Cord Stimulation, IEEE Transaction on Rehabilitation Engineering vol. 6, No. 2, Jun. 1998, 8 pages.
Wolter et al., "Continuous Versus Intermittent Spinal Cord Stimulation: An Analysis of Factors Influencing Clinical Efficacy," Neuromodulation: Technology at Neural Interface, www.neuromodulationjournal.com, 2011, 8 pages.
Woo MY, Campbell B. "Asynchronous Firing and Block of Peripheral Nerve Conduction by 20KC Alternating Current," Los Angeles Neuro Society, Jun. 1964; 87-94.
Yearwood et al., "A Prospective Comparison of Spinal Cord Stimulation (SCS) Using Dorsal Column Stimulation (DCS), Intraspinal Nerve Root Stimulation (INRS), and Varying Pulse Width in the Treatment of Chronic Low Back Pain," Congress of Neurological Surgeons 56th Annual Meeting, Oct. 7-12, 2006, 2 pages.
Yearwood et al., "Pulse Width Programming in Spinal Cord Stimulation: A Clinical Study," Pain Physician Journal, Jul./Aug. 2010, 16 pages.
Yearwood et al., Case Reports: "A Prospective Comparison of Spinal Cord Stimulation (SCS) Using Dorsal col. Stimulation (DCS), Intraspinal Nerve Root Stimulation (INRS), and Varying Pulse Width in the Treatment of Chronic Low Back Pain," Presented at the Congress of Neurological Surgeons 56th Annual Meeting, Oct. 7-12, 2006, 7 pages.

(56) References Cited

OTHER PUBLICATIONS

Zhang et al., "Simulation Analysis of Conduction Block in Myelinated Axons Induced by High-Frequency Biphasic Rectangular Pulses," IEEE Transactions on Biomedical Engineering, vol. 53., No. 7, Jul. 2006, 4 pages.
Zhang et al., Changes Across Time in Spike Rate and Spike Amplitude of Auditory Nerve Fibers Stimulated by Electric Pulse Trains, Journal of the Association for Research of Otolaryngology, 2007, 17 pages.
Amendment in Response to Final Office Action for U.S. Appl. No. 13/607,617, Applicant: Alataris et al., filed Nov. 2, 2015, 22 pages.
Amendment in Response to Final Office Action for U.S. Appl. No. 14/164,057, Applicant: Alataris et al., filed Aug. 22, 2014, 16 pages.
Amendment in Response to Final Office Action for U.S. Appl. No. 13/620,307, Applicant: Fang et al., filed Apr. 3, 2015, 20 pages.
Amendment in Response to Non-Final Office Action for U.S. Appl. No. 13/620,235, Applicant: Alataris et al., filed Oct. 28, 2014, 25 pages.
Amendment in Response to Non-Final Office Action for U.S. Appl. No. 12/264,836, Applicant: Alataris et al., filed Dec. 3, 2014, 23 pages.
Amendment in Response to Non-Final Office Action for U.S. Appl. No. 13/620,307, Applicant: Fang et al., filed Sep. 3, 2014, 21 pages.
Amendment in Response to Non-Final Office Action for U.S. Appl. No. 13/830,886, Applicant: Alataris et al., filed Feb. 24, 2014, 14 pages.
Amendment in Response to Non-Final Office Action for U.S. Appl. No. 13/830,992, Applicant: Alataris et al., filed Feb. 24, 2014, 14 pages.
Amendment in Response to Non-Final Office Action for U.S. Appl. No. 13/831,241, Applicant: Thacker et al., filed Nov. 2, 2015, 25 pages.
Amendment in Response to Non-Final Office Action for U.S. Appl. No. 13/831,151, Applicant: Thacker et al., filed Nov. 2, 2015, 27 pages.
Amendment in Response to Non-Final Office Action for U.S. Appl. No. 13/831,300, Applicant: Thacker et al., filed Nov. 2, 2015, 25 pages.
Amendment in Response to Non-Final Office Action for U.S. Appl. No. 13/831,381, Applicant: Thacker et al., filed Nov. 2, 2015, 25 pages.
Amendment in Response to Non-Final Office Action for U.S. Appl. No. 14/037,230, Applicant: Alataris et al., filed Mar. 3, 2014, 20 pages.
Amendment in Response to Non-Final Office Action for U.S. Appl. No. 14/164,044, Applicant: Alataris et al., filed Jul. 16, 2014, 16 pages.
Amendment in Response to Non-Final Office Action for U.S. Appl. No. 14/164,096, Applicant: Alataris et al., filed Jul. 12, 2014, 16 pages.
Amendment in Response to Non-Final Office Action for U.S. Appl. No. 14/522,500, Applicant: Alataris et al., filed Aug. 27, 2015, 34 pages.
Amendment in Response to Non-Final Office Action for U.S. Appl. No. 14/525,134, Applicant: Alataris et al., filed Mar. 16, 2015, 26 pages.
Amendment in Response to Non-Final Office Action for U.S. Appl. No. 15/134,285, Applicant: Alataris et al., filed Aug. 31, 2017, 19 pages.
Amendment in Response to Non-Final Office Action for U.S. Appl. No. 13/831,057, Applicant: Alataris et al., filed Jan. 23, 2014, 15 pages.
Amendment in Response to Non-Final Office Action for U.S. Appl. No. 12/765,747, Applicant: Alataris et al., filed Jan. 24, 2014, 21 pages.
Amendment in Response to Non-Final Office Action for U.S. Appl. No. 14/522,500, Applicant: Alataris et al., filed Mar. 16, 2015, 26 pages.
Amendment in Response to Non-Final Office Action for U.S. Appl. No. 14/525,134, Applicant: Alataris et al., filed Aug. 27, 2015, 35 pages.
Amendment in Response to Non-Final Office Action for U.S. Appl. No. 13/705,021, Applicant: Fang et al., filed Feb. 11, 2014, 18 pages.
Amendment in Response to Non-Final Office Action for U.S. Appl. No. 13/705,045, Applicant: Fang et al., filed Feb. 11, 2014, 19 pages.
Nevro Amendments and Comments in Response to Opinion and Summons to Oral Proceedings for European Patent No. 10703574.3, mailed Jul. 28, 2014, 6 pages.
Nevro Response to Communication pursuant to Article 94(3) EPC for European Patent No. 2586488, filed Oct. 1, 2015, 12 pages.
Nevro Response to Communication pursuant to Article 94(3) EPC for European U.S. Appl. No. 14/152,029, filed Aug. 24, 2017, 3 pages.
Nevro Response to Communication pursuant to Rules 161(1) and 162 EPC for European Patent Application No. 10703574.3, dated May 21, 2012, 5 pages.
Nevro Response to Examination Report for European Patent Application No. 10703574.3, dated Nov. 27, 2013, 3 pages.
Exhibit A1: *Invalidity Chart v. MacDonald* (U.S. Pat. No. 5,776,170), Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), Mar. 17, 2017, 294 pages.
Exhibit A2: *Invalidity Chart v. Spinner* (U.S. Patent Application Publication No. 2007/0213771), Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), Mar. 17, 2017, 235 pages.
Exhibit A3: *Invalidity Chart v. Knudson* (U.S. Patent Application Publication No. 2007/0073354), Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), Mar. 17, 2017, 301 pages.
Exhibit A4: *Invalidity Chart v. Butukhanov* (Soviet Union Publication No. 1512625), Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), Mar. 17, 2017, 233 pages.
Exhibit A5: *Invalidity Chart v. Sluijter* (U.S. Pat. No. 6,246,912), Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), Mar. 17, 2017, 226 pages.
Exhibit A6: *Invalidity Chart v. Kilgore* (U.S. Pat. No. 7,389,145), Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), Mar. 17, 2017, 219 pages.
Exhibit A7: *Invalidity Chart v. Royle* (U.S. Patent Application Publication No. 2006/0009820), Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), Mar. 17, 2017, 188 pages.
Exhibit A8: *Invalidity Chart v. King* (U.S. Patent Application Publication No. 2007/0149148), Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), Mar. 17, 2017, 222 pages.
Exhibit A9: *Invalidity Chart v. DeRidder* (U.S. Patent Application Publication No. 2011/0184488), Boston Scientific Corporation's and Boston Scientific Neuromodulation Corporation's Invalidity

(56) References Cited

OTHER PUBLICATIONS

Contentions, *Nevro Corp. v. Boston Scientific Corporation and Boston Scientific Neuromodulation Corporation*, Case No. 3:16-cv-06830-VC (N.D. Cal.), Mar. 17, 2017, 266 pages.
Exhibit A10: *Invalidity Chart v. Fang* (U.S. Patent Application Publication No. 2009/0204173), Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), Mar. 17, 2017, 191 pages.
Exhibit B1: *Invalidity Chart v. Boston Scientific's Precision Spinal Cord Stimulation System*, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), Mar. 17, 2017, 337 pages.
Exhibit C1: 35 U.S.C. § 103(a) Invalidity Chart, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), Mar. 17, 2017, 400 pages.
Declaration of Rafael Carbunaru in Support of Boston Scientific's Invalidity Contentions, *Nevro Corp.* (Plaintiff) vs. *Boston Scientific Corporation and Boston Scientific Neuromodulation Corporation*, Case No. 3:16-cv-06830-VC, executed Mar. 17, 2017, 5 pages.
Exhibit A of Declaration of Rafael Carbunaru: "Physician Implant Manual—Precision," in Support in Support of Defendants Boston Scientific Corporation's and Boston Scientific Neuromodulation Corporation's Invalidity Contentions, Advanced Bionics, 2004, 62 pages.
Exhibit B of Declaration of Rafael Carbunaru: "Physician Lead Manual—Precision," in Support in Support of Defendants Boston Scientific Corporation's and Boston Scientific Neuromodulation Corporation's Invalidity Contentions, Advanced Bionics, 2004, 62 pages.
Exhibit C of Declaration of Rafael Carbunaru: "Patient System Handbook—Precision," in Support in Support of Defendants Boston Scientific Corporation's and Boston Scientific Neuromodulation Corporation's Invalidity Contentions, Advanced Bionics, 2004, 93 pages.
Boston Scientific's Answer to First Amended Complaint and Defense, *Nevro Corp.* vs. *Boston Scientific Corporation and Boston Scientific Neuromodulation Corporation*, Case No. 3:16-cv-06830-VC, Jul. 13, 2017, 22 pages.
Defendant's First Amended Preliminary Invalidity Contentions, *Nevro Corp. v. Boston Scientific Corporation and Boston Scientific Neuromodulation Corporation*, Case No. 3:16-cv-06830-VC, Jun. 17, 2017, 93 pages.
First Amended Complaint for Patent Infringement and Declaratory Judgment, *Nevro Corp. v. Boston Scientific Corporation and Boston Scientific Neuromodulation Corporation*, Case No. 3:16-cv-06830-VC, Jun. 29, 2017, 45 pages.
Amended Exhibit C1 (amendments redlined): 35 U.S.C. § 103(a) Invalidity Chart, Boston Scientific Corporation's and Boston Scientific Neuromodulation Corporation's Invalidity Contentions, *Nevro Corpv. Boston Scientific Corporation and Boston Scientific Neuromodulation Corporation*, Case No. 3:16-cv-06830-VC (N.D. Cal.), Jun. 13, 2017, 423 pages.
Plaintiff Nevro Corp's Motion to Strike Inequitable Conduct Allegations From Defendants' Twelfth Affirmative Defense; Memorandum of Points and Authorities, *Nevro Corp.* vs. *Boston Scientific Corporation and Boston Scientific Neuromodulation Corporation*, Case No. 3:16-cv-06830-VC, Aug. 3, 2017, 10 pages.
Boston Scientific's Opposition to Nevro's Motion to Strike Inequitable Conduct Allegations from Defendants' Twelfth Affirmative Defense (ECF No. 172), *Nevro Corp.* vs. *Boston Scientific Corporation and Boston Scientific Neuromodulation Corporation*, Case No. 3:16-cv-06830-VC, Aug. 17, 2017, 17 pages.

Defendant's Second Amended Preliminary Invalidity Contentions, *Nevro Corp.* vs. *Boston Scientific Corporation and Boston Scientific Neuromodulation Corporation*, Case No. 3:16-cv-06830-VC, Aug. 10, 2017, 108 pages.
Exhibit A1 for Defendant's Second Amended Preliminary Invalidity Contentions: *Invalidity Chart v. MacDonald* (U.S. Pat. No. 5,776,170), Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), Aug. 10, 2017, 168 pages.
Exhibit A2 for Defendant's Second Amended Preliminary Invalidity Contentions: *Invalidity Chart v. Spinner* (U.S. Patent Application Publication No. 2007/0213771), Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), Aug. 10, 2017, 129 pages.
Exhibit A3 for Defendant's Second Amended Preliminary Invalidity Contentions: *Invalidity Chart v. Knudson* (U.S. Patent Application Publication No. 2007/0073354), Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), Aug. 10, 2017, 173 pages.
Exhibit A5 for Defendant's Second Amended Preliminary Invalidity Contentions: *Invalidity Chart v. Sluijter* (U.S. Pat. No. 6,246,912), Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), Aug. 10, 2017, 135 pages.
Exhibit A6 for Defendant's Second Amended Preliminary Invalidity Contentions: *Invalidity Chart v. Kilgore* (U.S. Pat. No. 7,389,145), Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), Aug. 10, 2017, 110 pages.
Exhibit A7 for Defendant's Second Amended Preliminary Invalidity Contentions: *Invalidity Chart v. Royle* (U.S. Patent Application Publication No. 2006/0009820), Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), Aug. 10, 2017, 111 pages.
Exhibit A9 for Defendant's Second Amended Preliminary Invalidity Contentions: *Invalidity Chart v. DeRidder* (U.S. Patent Application Publication No. 2011/0184488), Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), Aug. 10, 2017, 160 pages.
Exhibit A10 for Defendant's Second Amended Preliminary Invalidity Contentions: *Invalidity Chart v. Fang* (U.S. Patent Application Publication No. 2009/0204173), Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), Aug. 10, 2017, 114 pages.
Exhibit A11 for Defendant's Second Amended Preliminary Invalidity Contentions: *Invalidity Chart v. Alataris* (U.S. Pat. No. 8,712,533), Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), Aug. 10, 2017, 13 pages.
Exhibit A12 for Defendant's Second Amended Preliminary Invalidity Contentions: *Invalidity Chart v. Gaunt* (U.S. Patent Publication No. 2006/0184211), Boston Scientific Corporation's and Boston Scientific Neuromodulation Corporation's Invalidity Contentions,

(56) References Cited

OTHER PUBLICATIONS

*Nevro Corp. v. Boston Scientific Corporation and Boston Scientific Neuromodulation Corporation*, Case No. 3:16-cv-06830-VC (N.D. Cal.), Aug. 10, 2017, 113 pages.
Exhibit B1 for Defendant's Second Amended Preliminary Invalidity Contentions: *Invalidity Chart v. Boston Scientific's Precision Spinal Cord Stimulation System*, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), Aug. 10, 2017, 180 pages.
Exhibit C1 for Defendant's Second Amended Preliminary Invalidity Contentions: 35 U.S.C. § 103(a) Invalidity Chart, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), Aug. 10, 2017, 174 pages.
Corrected Exhibit C1 for Defendant's Second Amended Preliminary Invalidity Contentions: 35 U.S.C. § 103(a) Invalidity Chart, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), Aug. 10, 2017, 171 pages.
Nevro's Motion for Summary Adjudication—Notice of Motion, Motion and Memorandum of Points and Authorities in the Support of Nevro's Motion for Summary Adjudication (Document 461), *Nevro Corp. vs. Boston Scientific Corporation and Boston Scientific Neuromodulation Corporation*, Case No. 3:16-cv-06830-VC-MEJ, filed Jul. 30, 2018, 50 pages.
Declaration of Konstantinos Alataris in Support of Nevro's Motion of Summary Adjudication (Document 342-1), *Nevro Corp. vs. Boston Scientific Corporation and Boston Scientific Neuromodulation Corporation*, Case No. 3:16-cv-06830-VC-MEJ, Apr. 11, 2018, 3 pages.
Exhibit 1 for Declaration of Konstantinos Alataris in Support of Nevro's Motion of Summary Adjudication (Document 342-2), Notes from NBI Mayo Physician Meeting Dec. 4, 2016, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), Apr. 12, 2018, 3 pages.
Exhibit 2 for Declaration of Konstantinos Alataris in Support of Nevro's Motion of Summary Adjudication (Document 342-3), Notes from NBI Development—Mayo Clinic Dec. 4, 2016, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 11 pages.
Exhibit 3 for Declaration of Konstantinos Alataris in Support of Nevro's Motion of Summary Adjudication (Document 342-4), Sep. 2007 Email between O. Filho and Konstantinos Alataris, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 4 pages.
Exhibit 4 for Declaration of Konstantinos Alataris in Support of Nevro's Motion of Summary Adjudication (Document 342-5) NBI Development Inc., Jun. 12, 2007 Board Meeting, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 31 pages.
Declaration of Ben Pless in Support of Nevro's Motion for Summary Adjudication (Updated Redacted Version of EFC No. 347-24), *Nevro Corp. vs. Boston Scientific Corporation and Boston Scientific Neuromodulation Corporation*, Case No. 3:16-cv-06830-VC-MEJ, Apr. 11, 2018, 64 pages.
Exhibit A for Declaration of Ben Pless in Support of Nevro's Motion for Summary Adjudication (Document 342-7) Curriculum Vitae of Benjamin Pless, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Jul. 30, 2018, 15 pages.
Declaration of Eric C. Pai in Support of Nevro's Motion for Summary Adjudication (Document 343), *Nevro Corp. vs. Boston Scientific Corporation and Boston Scientific Neuromodulation Corporation*, Case No. 3:16-cv-06830-VC-MEJ, Apr. 12, 2018, 11 pages.
Exhibit 1 for Declaration of Eric C. Pai in Support of Nevro's Motion for Summary Adjudication (Document 343-1) Chart—Asserted Claims with Disputed Terms Underlined, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 5 pages.
Exhibit 2 for Declaration of Eric C. Pai in Support of Nevro's Motion for Summary Adjudication (Document 343-2) Certified U.S. Pat. No. 8,359,102, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 34 pages.
Exhibit 3 for Declaration of Eric C. Pai in Support of Nevro's Motion for Summary Adjudication (Document 343-3) Certified U.S. Pat. No. 8,712,533, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 37 pages.
Exhibit 4 for Declaration of Eric C. Pai in Support of Nevro's Motion for Summary Adjudication (Document 343-4) Certified U.S. Pat. No. 8,768,472, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 37 pages.
Exhibit 5 for Declaration of Eric C. Pai in Support of Nevro's Motion for Summary Adjudication (Document 343-5) Certified U.S. Pat. No. 8,792,988, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 35 pages.
Exhibit 6 for Declaration of Eric C. Pai in Support of Nevro's Motion for Summary Adjudication (Document 343-6) Certified U.S. Pat. No. 9,327,125, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 40 pages.
Exhibit 7 for Declaration of Eric C. Pai in Support of Nevro's Motion for Summary Adjudication (Document 343-7) Certified U.S. Pat. No. 9,333,357, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 39 pages.
Exhibit 8 for Declaration of Eric C. Pai in Support of Nevro's Motion for Summary Adjudication (Document 343-8) Certified U.S. Pat. No. 9,480,842, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 38 pages.

(56) References Cited

OTHER PUBLICATIONS

Exhibit 9 for Declaration of Eric C. Pai in Support of Nevro's Motion for Summary Adjudication (Document 343-9) Article by Leonardo Kapural et al., Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 11 pages.

Exhibit 10 for Declaration of Eric C. Pai in Support of Nevro's Motion for Summary Adjudication (Document 343-10) Article by Antonio Foletti et al., Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 15 pages.

Exhibit 11 for Declaration of Eric C. Pai in Support of Nevro's Motion for Summary Adjudication (Document 343-11) Article by Leonardo Kapural et al., Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 12 pages.

Exhibit 12 for Declaration of Eric C. Pai in Support of Nevro's Motion for Summary Adjudication (Document 343-12) Poster by Mark Wallace et al., Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 2 pages.

Exhibit 13 for Declaration of Eric C. Pai in Support of Nevro's Motion for Summary Adjudication (Document 343-13) Summary of Safety and Effectiveness Data (SSED), Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 6 pages.

Exhibit 14 for Declaration of Eric C. Pai in Support of Nevro's Motion for Summary Adjudication (Document 343-14) Nevro—Notes from Las Vegas and Our Survey of 50 US pain docs, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 19 pages.

Exhibit 15 for Declaration of Eric C. Pai in Support of Nevro's Motion for Summary Adjudication (Document 343-15) Apr. 2012 Email between K. Bradley and J. Cassidy, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 5 pages.

Exhibit 16 for Declaration of Eric C. Pai in Support of Nevro's Motion for Summary Adjudication (Document 343-16) Entire Document Sealed, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 1 page.

Exhibit 17 for Declaration of Eric C. Pai in Support of Nevro's Motion for Summary Adjudication (Document 343-17) Entire Document Sealed, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 1 page.

Exhibit 18 for Declaration of Eric C. Pai in Support of Nevro's Motion for Summary Adjudication (Document 343-18) Entire Document Sealed, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 1 page.

Exhibit 19 for Declaration of Eric C. Pai in Support of Nevro's Motion for Summary Adjudication (Document 343-19) Entire Document Sealed, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 1 page.

Exhibit 20 for Declaration of Eric C. Pai in Support of Nevro's Motion for Summary Adjudication (Document 343-20) Redacted Version of Document Sought to be Sealed—Excerpts from May 18, 2018 Deposition of R. Carbunaru, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 12 pages.

Exhibit 21 for Declaration of Eric C. Pai in Support of Nevro's Motion for Summary Adjudication (Document 343-21) Certified U.S. Pat. No. 8,792,988, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 9 pages.

Exhibit 22 for Declaration of Eric C. Pai in Support of Nevro's Motion for Summary Adjudication (Document 462) Updated Redacted Version of ECF No. 347-10—Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Jul. 30, 2018, 9 pages.

Exhibit 23 for Declaration of Eric C. Pai in Support of Nevro's Motion for Summary Adjudication (Document 463) Updated Redacted Version of ECF No. 347-12, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Jul. 30, 2018, 23 pages.

Exhibit 24 for Declaration of Eric C. Pai in Support of Nevro's Motion for Summary Adjudication (Document 343-24) Redacted Version of Document Sought to Be Sealed—BSC's Supplemental Responses and Objections to Nevro First Set of Interrogatory Request, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 11 pages.

Exhibit 25 for Declaration of Eric C. Pai in Support of Nevro's Motion for Summary Adjudication (Document 464) Updated Redacted Version of ECF No. 347-16—BSC's Second Supplemental Responses and Objections to Nevro First Set of Interrogatory Request, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 12 pages.

Exhibit 26 for Declaration of Eric C. Pai in Support of Nevro's Motion for Summary Adjudication (Document 343-26) Decision Denying Institution of Inter Partes Review 37 CFR § 42.108—IPR2015-01203 U.S. Pat. No. 8,359,102, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 21 pages.

Exhibit 27 for Declaration of Eric C. Pai in Support of Nevro's Motion for Summary Adjudication (Document 343-27) Decision Denying Institution of Inter Partes Review 37 CFR § 42.108—IPR2015-01204 U.S. Pat. No. 8,359,102, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 15 pages.

(56) References Cited

OTHER PUBLICATIONS

Exhibit 28 for Declaration of Eric C. Pai in Support of Nevro's Motion for Summary Adjudication (Document 343-28) Certified U.S. Pat. No. 9,333,357, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 13 pages.

Exhibit 29 for Declaration of Eric C. Pai in Support of Nevro's Motion for Summary Adjudication (Document 343-29) Rebuttal Expert Report and Declaration of Gene Fridman, Ph.D., regarding Claim Construction—Feb. 14, 2018, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 13 pages.

Exhibit 30 for Declaration of Eric C. Pai in Support of Nevro's Motion for Summary Adjudication (Document 343-30) Deposition of Dr. Gene Fridman on Mar. 7, 2018, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 49 pages.

Exhibit 31 for Declaration of Eric C. Pai in Support of Nevro's Motion for Summary Adjudication (Document 343-31) Rebuttal Expert Report and Declaration of Gene Fridman, Ph.D., regarding Claim Construction—Jan. 18, 2018, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 12 pages.

Exhibit 32 for Declaration of Eric C. Pai in Support of Nevro's Motion for Summary Adjudication (Document 343-32) Deposition of Kaoru Lee Adair—May 10, 2017, Entire Document Sought to be Sealed, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 1 page.

Exhibit 33 for Declaration of Eric C. Pai in Support of Nevro's Motion for Summary Adjudication (Document 343-33) Expert Report and Declaration of Adam Lipson, M.D., pursuant to Federal Rule of Civil Procedure 26(A)(2)(B) dated Jan. 18, 2017, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 4 pages.

Exhibit 34 for Declaration of Eric C. Pai in Support of Nevro's Motion for Summary Adjudication (Document 343-34) Stedman's Medical Dictionary 27th Edition, definition "paresthesia", Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 4 pages.

Exhibit 35 for Declaration of Eric C. Pai in Support of Nevro's Motion for Summary Adjudication (Document 343-35) Dorland's Illustrated Medical Dictionary, definition "paresthesia", Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 4 pages.

Exhibit 36 for Declaration of Eric C. Pai in Support of Nevro's Motion for Summary Adjudication (Document 343-36) Mosby's Medical Dictionary, definition "paresthesia", Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 5 pages.

Exhibit 37 for Declaration of Eric C. Pai in Support of Nevro's Motion for Summary Adjudication (Document 343-37) National Institute of Neurological Disorders and Stroke - Paresthesia Information Page, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 4 pages.

Exhibit 38 for Declaration of Eric C. Pai in Support of Nevro's Motion for Summary Adjudication (Document 343-38) Videotaped Deposition of Richard T. Mihran, Ph.D. on Mar. 12, 2018, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 10 pages.

Exhibit 39 for Declaration of Eric C. Pai in Support of Nevro's Motion for Summary Adjudication (Document 343-39) Boston Scientific—Precision Spinal Cord Stimulator System with MultiWave Technology Clinician Manual,, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 68 pages.

Exhibit 40 for Declaration of Eric C. Pai in Support of Nevro's Motion for Summary Adjudication (Document 343-40) BSC's Amended and Supplemental Responses and Objections to Nevro's Second Set of Interrogatories (Nos. 9, 10) dated Aug. 24, 2017, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 18 pages.

Exhibit 41 for Declaration of Eric C. Pai in Support of Nevro's Motion for Summary Adjudication (Document 343-41) Rebuttal Expert Report of Richard T. Mihran, Ph.D. dated Feb. 14, 2018, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 23 pages.

Exhibit 42 for Declaration of Eric C. Pai in Support of Nevro's Motion for Summary Adjudication (Document 343-42) Redacted Version of Document Sought to be Sealed—Videotaped Deposition of Nevro Corp, with designated corporate representative Jim Cassidy on May 17, 2017, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 5 pages.

Exhibit 43 for Declaration of Eric C. Pai in Support of Nevro's Motion for Summary Adjudication (Document 343-43) Entire Document Sought to be Sealed—Deposition of Kaoru Lee Adair taken on May 10, 2017, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 1 page.

Exhibit 44 for Declaration of Eric C. Pai in Support of Nevro's Motion for Summary Adjudication (Document 343-44) Entire Document Sought to be Sealed—Deposition of Kaoru Lee Adair taken on May 10, 2017, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 1 page.

Exhibit 45 for Declaration of Eric C. Pai in Support of Nevro's Motion for Summary Adjudication (Document 343-45) Entire Document Sought to be Sealed - Deposition of Kaoru Lee Adair taken on May 10, 2017, Boston Scientific Corporation's and Boston Scientific Neuromodulation Corporation's Invalidity Contentions, *Nevro*

(56) References Cited

OTHER PUBLICATIONS

Corp. v. *Boston Scientific Corporation and Boston Scientific Neuromodulation Corporation*, Case No. 3:16-cv-06830-VC (N.D. Cal.), filed Apr. 12, 2018, 1 page.
Exhibit 46 for Declaration of Eric C. Pai in Support of Nevro's Motion for Summary Adjudication (Document 343-46) Entire Document Sought to be Sealed—Deposition of Kaoru Lee Adair taken on May 10, 2017, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 1 page.
Exhibit 47 for Declaration of Eric C. Pai in Support of Nevro's Motion for Summary Adjudication (Document 343-47) Entire Document Sought to be Sealed—Deposition of Kaoru Lee Adair taken on May 10, 2017, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 1 page.
Exhibit 48 for Declaration of Eric C. Pai in Support of Nevro's Motion for Summary Adjudication (Document 343-48) Defendant's Identification of 40 Prior Art Grounds for Invalidity dated Dec. 22, 2017, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 4 pages.
Exhibit 49 for Declaration of Eric C. Pai in Support of Nevro's Motion for Summary Adjudication (Document 343-49) Defendant's Second Amended Preliminary Invalidity Contentions dated Aug. 10, 2017, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 47 pages.
Exhibit 50 for Declaration of Eric C. Pai in Support of Nevro's Motion for Summary Adjudication (Document 343-50) Declaration of Rafael Carbunaru in Support of Boston Scientific's Invalidity Contentions dated Mar. 17, 2017, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 6 pages.
Exhibit 51 for Declaration of Eric C. Pai in Support of Nevro's Motion for Summary Adjudication (Document 343-51) Declaration of Kaoru Lee Adair in Support of Boston Scientific's Motion to Dismiss Nevro's Declaratory Judgment Claims dated Dec. 27, 2016, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 5 pages.
Exhibit 52 for Declaration of Eric C. Pai in Support of Nevro's Motion for Summary Adjudication (Document 343-52) Expert Report of Richard T. Mihran, Ph.D., regarding Invalidity of U.S. Pat. Nos. 8,712,533; 9,327,125; 8,359,102; 9,480,842; 9,333,357; 8,792,988; and 8,768,472 dated Jan. 18, 2018, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 78 pages.
Exhibit 53 for Declaration of Eric C. Pai in Support of Nevro's Motion for Summary Adjudication (Document 343-53) Redacted Version of Document Sought to be Sealed—Rebuttal Expert Report and Declaration of Daniel Lanovaz dated Feb. 14, 2017, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 6 pages.
Exhibit 54 for Declaration of Eric C. Pai in Support of Nevro's Motion for Summary Adjudication (Document 343-54) Certified U.S. Pat. No. 8,712,533, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 13 pages.
Exhibit 55 for Declaration of Eric C. Pai in Support of Nevro's Motion for Summary Adjudication (Document 343-55) U.S. Patent Application No. 2009/0204173 to Fang et al., Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 33 pages.
Exhibit 56 for Declaration of Eric C. Pai in Support of Nevro's Motion for Summary Adjudication (Document 343-56) Deposition of Konstantinos Alataris dated Nov. 14, 2017, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 34 pages.
Exhibit 57 for Declaration of Eric C. Pai in Support of Nevro's Motion for Summary Adjudication (Document 343-57) Videotaped Deposition of Andre B. Walker dated Nov. 10, 2017, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 26 pages.
Exhibit 58 for Declaration of Eric C. Pai in Support of Nevro's Motion for Summary Adjudication (Document 343-58) Videotaped Deposition of Zi-Ping Fang dated Nov. 2, 2017, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 12 pages.
Exhibit 59 for Declaration of Eric C. Pai in Support of Nevro's Motion for Summary Adjudication (Document 343-59) Videotaped Deposition of Anthony Vincent Caparso dated Nov. 2, 2017, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 8 pages.
Exhibit 60 for Declaration of Eric C. Pai in Support of Nevro's Motion for Summary Adjudication (Document 343-60) Videotaped Deposition of Brian Erickson dated Dec. 15, 2017, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 44 pages.
Exhibit 61 for Declaration of Eric C. Pai in Support of Nevro's Motion for Summary Adjudication (Document 343-61) Deposition of Yougandh Chitre dated Nov. 20, 2017, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 6 pages.
Exhibit 62 for Declaration of Eric C. Pai in Support of Nevro's Motion for Summary Adjudication (Document 343-62) Deposition of Sangsoo Wesley Park dated Nov. 27, 2017, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 8 pages.

(56) References Cited

OTHER PUBLICATIONS

Exhibit 63 for Declaration of Eric C. Pai in Support of Nevro's Motion for Summary Adjudication (Document 343-63) Deposition of Jon Parker dated Nov. 16, 2017, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 8 pages.

Exhibit 64 for Declaration of Eric C. Pai in Support of Nevro's Motion for Summary Adjudication (Document 343-64) Videotaped James Thacker dated Dec. 7, 2017 (vol. 1), Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 10 pages.

Exhibit 65 for Declaration of Eric C. Pai in Support of Nevro's Motion for Summary Adjudication (Document 343-65) Sep. 2007 Email between O. Filho and K. Alataris, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 4 pages.

Exhibit 66 for Declaration of Eric C. Pai in Support of Nevro's Motion for Summary Adjudication (Document 343-66) Redacted Version of Document Sought to be Sealed—BSC's Dec. 1, 2017 Supplemental Responses and Objections to Nevro's Second Set of Interrogatories (Nos. 10 and 14), Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 13 pages.

Exhibit 67 for Declaration of Eric C. Pai in Support of Nevro's Motion for Summary Adjudication (Document 343-67) Certified U.S. Appl. No. 60/985,353, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 63 pages.

Exhibit 68 for Declaration of Eric C. Pai in Support of Nevro's Motion for Summary Adjudication (Document 343-68) Certified U.S. Appl. No. 12/264,836, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 67 pages.

Exhibit 69 for Declaration of Eric C. Pai in Support of Nevro's Motion for Summary Adjudication (Document 343-69) Certified Copy for U.S. Appl. No. 12/264,836, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 119 pages.

Exhibit 70 for Declaration of Eric C. Pai in Support of Nevro's Motion for Summary Adjudication (Document 343-70) Request to Add to Originally Named Inventors for U.S. Appl. No. 12/264,836, filed Aug. 13, 2012, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 27 pages.

Exhibit 71 for Declaration of Eric C. Pai in Support of Nevro's Motion for Summary Adjudication (Document 343-71) Poster by Yearwood et al., Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 8 pages.

Exhibit 72 for Declaration of Eric C. Pai in Support of Nevro's Motion for Summary Adjudication (Document 343-72) Case Report by Yearwood et al., Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 3 pages.

Exhibit 73 for Declaration of Eric C. Pai in Support of Nevro's Motion for Summary Adjudication (Document 343-73) Entire Document Sought to be Sealed—Deposition of Rafael Carbunaru taken on Nov. 14, 2017, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 1 page.

Exhibit 74 for Declaration of Eric C. Pai in Support of Nevro's Motion for Summary Adjudication (Document 343-74) Deposition of David Caraway dated Nov. 14, 2017, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 9 pages.

Exhibit 75 for Declaration of Eric C. Pai in Support of Nevro's Motion for Summary Adjudication (Document 343-75) Boston Scientific document, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 5 pages.

Declaration of Carson D. Anderson in Support of Nevro's Administrative Motion to File under Seal Portions of Nevro's Motion for Summary Adjudication and Supporting Documents (Document 348), *Nevro Corp. vs. Boston Scientific Corporation and Boston Scientific Neuromodulation Corporation*, Case No. 3:16-cv-06830-VC-MEJ, Apr. 16, 2018, 10 pages.

Exhibit A for Declaration of Carson D. Anderson in Support of Nevro's Administrative Motion to File under Seal Portions of Nevro's Motion for Summary Adjudication and Supporting Documents (Document 347-1) Redacted Version of Document Sought to Be Filed under Seal—Nevro's Notice of Motion, *Nevro Corp. vs. Boston Scientific Corporation and Boston Scientific Neuromodulation Corporation*, Case No. 3:16-cv-06830-VC-MEJ, Apr. 16, 2018, 50 pages.

Exhibit A—Updated—for Declaration of Carson D. Anderson in Support of Nevro's Administrative Motion to File under Seal Portions of Nevro's Motion for Summary Adjudication and Supporting Documents (Document 347-2 / Document 461) Redacted Version of Document Sought to Be Filed under Seal—Nevro's Motion for Summary Adjudication, *Nevro Corp. vs. Boston Scientific Corporation and Boston Scientific Neuromodulation Corporation*, Case No. 3:16-cv-06830-VC-MEJ, Jul. 30, 2018, 50 pages.

Exhibit B for Declaration of Carson D. Anderson in Support of Nevro's Administrative Motion to File under Seal Portions of Nevro's Motion for Summary Adjudication and Supporting Documents (Document 347-3) Redacted Version of Document Sought to Be Filed under Seal—Videotaped Deposition of Rafael Carbunaru, Ph.D., taken Nov. 15, 2017, *Nevro Corp. vs. Boston Scientific Corporation and Boston Scientific Neuromodulation Corporation*, Case No. 3:16-cv-06830-VC-MEJ, filed Apr. 16, 2018, 46 pages.

Exhibit C for Declaration of Carson D. Anderson in Support of Nevro's Administrative Motion to File under Seal Portions of Nevro's Motion for Summary Adjudication and Supporting Documents (Document 347-5) Boston Scientific Neuromodulation—SPRINT High Rate—Product Opportunity Proposal, *Nevro Corp. vs. Boston Scientific Corporation and Boston Scientific Neuromodulation Corporation*, Case No. 3:16-cv-06830-VC-MEJ, filed Apr. 16, 2018, 14 pages.

Exhibit D for Declaration of Carson D. Anderson in Support of Nevro's Administrative Motion to File under Seal Portions of Nevro's Motion for Summary Adjudication and Supporting Documents (Document 347-7) Redacted Version of Document Sought to be Filed under Seal—Boston Scientific Neuromodulation—Sprint High Rate—Project Authorization Review, *Nevro Corp. vs. Boston*

(56) References Cited

OTHER PUBLICATIONS

*Scientific Corporation and Boston Scientific Neuromodulation Corporation*, Case No. 3:16-cv-06830-VC-MEJ, filed Apr. 16, 2018, 7 pages.
Exhibit E for Declaration of Carson D. Anderson in Support of Nevro's Administrative Motion to File under Seal Portions of Nevro's Motion for Summary Adjudication and Supporting Documents (Document 347-9) Redacted Version of Document Sought to be Filed under Seal—Videotaped Deposition of Kaoru Lee Adair, *Nevro Corp.* vs. *Boston Scientific Corporation and Boston Scientific Neuromodulation Corporation*, Case No. 3:16-cv-06830-VC-MEJ, filed Apr. 16, 2018, 12 pages.
Exhibit E—Updated—for Declaration of Carson D. Anderson in Support of Nevro's Administrative Motion to File under Seal Portions of Nevro's Motion for Summary Adjudication and Supporting Documents (Document 347-10) Redacted Version of Document Sought to be Filed under Seal—Videotaped Deposition of Kaoru Lee Adair, taken Nov. 17, 2017, *Nevro Corp.* vs. *Boston Scientific Corporation and Boston Scientific Neuromodulation Corporation*, Case No. 3:16-cv-06830-VC-MEJ, filed Apr. 16, 2018, 12 pages.
Exhibit F for Declaration of Carson D. Anderson in Support of Nevro's Administrative Motion to File under Seal Portions of Nevro's Motion for Summary Adjudication and Supporting Documents (Document 347-11) Redacted Version of Document Sought to be Filed under Seal—Videotaped Deposition of Kaoru Lee Adair, taken May 10, 2017, *Nevro Corp.* vs. *Boston Scientific Corporation and Boston Scientific Neuromodulation Corporation*, Case No. 3:16-cv-06830-VC-MEJ, filed Apr. 16, 2018, 23 pages.
Exhibit F—Updated—for Declaration ofCarson D. Anderson in Support of Nevro's Administrative Motion to File under Seal Portions of Nevro's Motion for Summary Adjudication and Supporting Documents (Document 347-12) Redacted Version of Document Sought to be Filed under Seal—Videotaped Deposition of Kaoru Lee Adair, taken May 10, 2017, *Nevro Corp.* vs. *Boston Scientific Corporation and Boston Scientific Neuromodulation Corporation*, Case No. 3:16-cv-06830-VC-MEJ, filed Apr. 16, 2018, 23 pages.
Exhibit G for Declaration of Carson D. Anderson in Support of Nevro's Administrative Motion to File under Seal Portions of Nevro's Motion for Summary Adjudication and Supporting Documents (Document 347-13) BSC's Supplemental Responses and Objections to Nevro's First Set of Interrogatory Requests (1-8), *Nevro Corp.* vs. *Boston Scientific Corporation and Boston Scientific Neuromodulation Corporation*, Case No. 3:16-cv-06830-VC-MEJ, filed Apr. 16, 2018, 12 pages.
Exhibit H for Declaration of Carson D. Anderson in Support of Nevro's Administrative Motion to File under Seal Portions of Nevro's Motion for Summary Adjudication and Supporting Documents (Document 347-15) Redacted Version of Document Sought to be Filed under Seal—BSC's Second Supplemental Responses and Objections to Nevro's First Set of Interrogatory Requests (1-8), *Nevro Corp.* vs. *Boston Scientific Corporation and Boston Scientific Neuromodulation Corporation*, Case No. 3:16-cv-06830-VC-MEJ, filed Apr. 16, 2018, 12 pages.
Exhibit H—Updated—for Declaration of Carson D. Anderson in Support of Nevro's Administrative Motion to File under Seal Portions of Nevro's Motion for Summary Adjudication and Supporting Documents (Document 347-16) Updated Redacted Version of Document Sought to be Filed under Seal—BSC's Second Supplemental Responses and Objections to Nevro's First Set of Interrogatory Requests (1-8), *Nevro Corp.* vs. *Boston Scientific Corporation and Boston Scientific Neuromodulation Corporation*, Case No. 3:16-cv-06830-VC-MEJ, filed Apr. 16, 2018, 12 pages.
Exhibit I for Declaration ofCarson D. Anderson in Support of Nevro's Administrative Motion to File under Seal Portions of Nevro's Motion for Summary Adjudication and Supporting Documents (Document 347-17) Redacted Version of Document Sought to be Filed under Seal—Rebuttal Expert Report of Richard T. Mihran, Ph.D., *Nevro Corp.* vs. *Boston Scientific Corporation and Boston Scientific Neuromodulation Corporation*, Case No. 3:16-cv-06830-VC-MEJ, filed Apr. 16, 2018, 24 pages.
Exhibit J for Declaration of Carson D. Anderson in Support of Nevro's Administrative Motion to File under Seal Portions of Nevro's Motion for Summary Adjudication and Supporting Documents (Document 347-19) Redacted Version of Document Sought to be Filed under Seal—Oct. 24, 2016 Boston Scientific Letter to U.S. Food and Drug Administration, *Nevro Corp.* vs. *Boston Scientific Corporation and Boston Scientific Neuromodulation Corporation*, Case No. 3:16-cv-06830-VC-MEJ, filed Apr. 16, 2018, 5 pages.
Exhibit K for Declaration of Carson D. Anderson in Support of Nevro's Administrative Motion to File under Seal Portions of Nevro's Motion for Summary Adjudication and Supporting Documents (Document 347-21) Redacted Version of Document Sought to be Filed under Seal—Rebuttal Expert Report and Declaration of Daniel Lanovaz dated Feb. 14, 2017, *Nevro Corp.* vs. *Boston Scientific Corporation and Boston Scientific Neuromodulation Corporation*, Case No. 3:16-cv-06830-VC-MEJ, filed Apr. 16, 2018, 7 pages.
Exhibit L for Declaration of Carson D. Anderson in Support of Nevro's Administrative Motion to File under Seal Portions of Nevro's Motion for Summary Adjudication and Supporting Documents (Document 347-23) Redacted Version of Document Sought to be Filed under Seal—Declaration of Ben Pless in Support of Nevro's Motion of Summary Adjudication dated Apr. 12, 2018, *Nevro Corp.* vs. *Boston Scientific Corporation and Boston Scientific Neuromodulation Corporation*, Case No. 3:16-cv-06830-VC-MEJ, filed Apr. 16, 2018, 64 pages.
Exhibit L—Updated—for Declaration ofCarson D. Anderson in Support of Nevro's Administrative Motion to File under Seal Portions of Nevro's Motion for Summary Adjudication and Supporting Documents (Document 347-24) Updated Redacted Version of Document Sought to be Filed under Seal—Declaration of Ben Pless in Support of Nevro's Motion of Summary Adjudication dated Apr. 12, 2018, *Nevro Corp.* vs. *Boston Scientific Corporation and Boston Scientific Neuromodulation Corporation*, Case No. 3:16-cv-06830-VC-MEJ, filed Apr. 16, 2018, 64 pages.
Declaration of Rafael Carbunaru in Support of Nevro's Administrative Motion to File under Seal Portions of Nevro's Motion for Summary Adjudication and Supporting Documents (Document 347-25), *Nevro Corp.* vs. *Boston Scientific Corporation and Boston Scientific Neuromodulation Corporation*, Case No. 3:16-cv-06830-VC-MEJ, filed Apr. 16, 2018, 13 pages.
[Proposed] Order Granting Administrative Motion to File under Seal Portions of Nevro's Administrative Motion to File under Seal Portions of Nevro's Motion for Summary Adjudication and Supporting Documents (ECF No. 341) (Document 347-26), *Nevro Corp.* vs. *Boston Scientific Corporation and Boston Scientific Neuromodulation Corporation*, Case No. 3:16-cv-06830-VC-MEJ, filed Apr. 16, 2018, 5 pages.
Boston Scientific's Responsive Claim Construction Brief, Opposition to Nevro's Motion for Summary Adjudication and Supporting Documents (Document 466), Updated Redacted Version of ECF No. 357-4, *Nevro Corp.* vs. *Boston Scientific Corporation and Boston Scientific Neuromodulation Corporation*, Case No. 3:16-cv-06830-VC-MEJ, filed Jul. 30, 2018, 61 pages.
Expert Report and Declaration of Gene Fridman, Ph.D., regarding Claim Construction (Document 358-1), *Nevro Corp.* vs. *Boston Scientific Corporation and Boston Scientific Neuromodulation Corporation*, Case No. 3:16-cv-06830-VC-MEJ, filed Apr. 26, 2018, 18 pages.
Rebuttal Expert Report and Declaration of Gene Fridman, Ph.D., regarding Claim Construction (Document 358-2), *Nevro Corp.* vs. *Boston Scientific Corporation and Boston Scientific Neuromodulation Corporation*, Case No. 3:16-cv-06830-VC-MEJ, filed Apr. 26, 2018, 11 pages.
Declaration of Richard T. Mihran, Ph.D., regarding Claim Construction Brief (Document 358-3), *Nevro Corp.* vs. *Boston Scientific Corporation and Boston Scientific Neuromodulation Corporation*, Case No. 3:16-cv-06830-VC-MEJ, filed Apr. 26, 2018, 2 pages.
Exhibit A for Declaration of Richard T. Mihran, Ph.D., regarding Claim Construction Brief (Document 358-4), Expert Report of

(56) References Cited

OTHER PUBLICATIONS

Richard T. Mihran, Ph.D. regarding Invalidity of U.S. Pat. Nos. 8,712,533; 9,327,125; 8,359,102; 9,480,842; 9,333,357; 8,792,988; and 8,768,472, *Nevro Corp. vs. Boston Scientific Corporation and Boston Scientific Neuromodulation Corporation*, Case No. 3:16-cv-06830-VC-MEJ, filed Apr. 26, 2018, 129 pages.
Exhibit B Declaration of Richard T. Mihran, Ph.D., regarding Claim Construction Brief (Document 358-5), Redacted Version of Document Sought to be Filed under Seal—Rebuttal Expert Report of Richard T. Mihran, Ph.D., *Nevro Corp. vs. Boston Scientific Corporation and Boston Scientific Neuromodulation Corporation*, Case No. 3:16-cv-06830-VC-MEJ, filed Apr. 26, 2018, 79 pages.
Declaration of Clara W. Wang in Support of Boston Scientific's Responsive regarding Claim Construction Brief; Opposition to Nevro's Motion for Summary Judgement and Opening Motion for Summary Judgement (Document 358-6), *Nevro Corp. vs. Boston Scientific Corporation and Boston Scientific Neuromodulation Corporation*, Case No. 3:16-cv-06830-VC-MEJ, filed Apr. 26, 2018, 8 pages.
Exhibit 1 for Declaration of Clara W. Wang in Support of Boston Scientific's Responsive regarding Claim Construction Brief; Opposition to Nevro's Motion for Summary Judgement and Opening Motion for Summary Judgement (Document 358-7), Sep. 2005 Email between K. Bradley and M. Moffitt, *Nevro Corp. vs. Boston Scientific Corporation and Boston Scientific Neuromodulation Corporation*, Case No. 3:16-cv-06830-VC-MEJ, filed Apr. 26, 2018, 2 pages.
Exhibit 2 for Declaration of Clara W. Wang in Support of Boston Scientific's Responsive regarding Claim Construction Brief; Opposition to Nevro's Motion for Summary Judgement and Opening Motion for Summary Judgement (Document 358-8), Filed under Seal—Document NEVRO_BSXCA0165810-52, *Nevro Corp. vs. Boston Scientific Corporation and Boston Scientific Neuromodulation Corporation*, Case No. 3:16-cv-06830-VC-MEJ, filed Apr. 26, 2018, 1 page.
Exhibit 3 for Declaration of Clara W. Wang in Support of Boston Scientific's Responsive regarding Claim Construction Brief; Opposition to Nevro's Motion for Summary Judgement and Opening Motion for Summary Judgement (Document 358-9), Filed under Seal—Document NEVRO_BSXCA0389050-100, *Nevro Corp. vs. Boston Scientific Corporation and Boston Scientific Neuromodulation Corporation*, Case No. 3:16-cv-06830-VC-MEJ, filed Apr. 26, 2018, 1 page.
Exhibit 4 for Declaration of Clara W. Wang in Support of Boston Scientific's Responsive regarding Claim Construction Brief; Opposition to Nevro's Motion for Summary Judgement and Opening Motion for Summary Judgement (Document 358-10), Summary of Safety and Effectiveness Data (SSED), *Nevro Corp. vs. Boston Scientific Corporation and Boston Scientific Neuromodulation Corporation*, Case No. 3:16-cv-06830-VC-MEJ, filed Apr. 26, 2018, 57 pages.
Exhibit 5 for Declaration of Clara W. Wang in Support of Boston Scientific's Responsive regarding Claim Construction Brief; Opposition to Nevro's Motion for Summary Judgement and Opening Motion for Summary Judgement (Document 358-11), Article by Andres et al., *Nevro Corp. vs. Boston Scientific Corporation and Boston Scientific Neuromodulation Corporation*, Case No. 3:16-cv-06830-VC-MEJ, filed Apr. 26, 2018, 22 pages.
Exhibit 6 for Declaration of Clara W. Wang in Support of Boston Scientific's Responsive regarding Claim Construction Brief; Opposition to Nevro's Motion for Summary Judgement and Opening Motion for Summary Judgement (Document 358-12), Article by Thomson et al., *Nevro Corp. vs. Boston Scientific Corporation and Boston Scientific Neuromodulation Corporation*, Case No. 3:16-cv-06830-VC-MEJ, filed Apr. 26, 2018, 11 pages.
Exhibit 7 for Declaration of Clara W. Wang in Support of Boston Scientific's Responsive regarding Claim Construction Brief; Opposition to Nevro's Motion for Summary Judgement and Opening Motion for Summary Judgement (Document 358-13), Filed under Seal—Document labeled NEVRO_BSXCA0053540-89, *Nevro Corp. vs. Boston Scientific Corporation and Boston Scientific Neuromodulation Corporation*, Case No. 3:16-cv-06830-VC-MEJ, filed Apr. 26, 2018, 1 page.
Exhibit 8 for Declaration of Clara W. Wang in Support of Boston Scientific's Responsive regarding Claim Construction Brief; Opposition to Nevro's Motion for Summary Judgement and Opening Motion for Summary Judgement (Document 358-14), Filed under Seal—Document labeled NEVRO_BSXCA0055766-70, *Nevro Corp. vs. Boston Scientific Corporation and Boston Scientific Neuromodulation Corporation*, Case No. 3:16-cv-06830-VC-MEJ, filed Apr. 26, 2018, 1 page.
Exhibit 9 for Declaration of Clara W. Wang in Support of Boston Scientific's Responsive regarding Claim Construction Brief; Opposition to Nevro's Motion for Summary Judgement and Opening Motion for Summary Judgement (Document 358-15), Filed under Seal—Document labeled NEVRO_BSXCA0049348-69, *Nevro Corp. vs. Boston Scientific Corporation and Boston Scientific Neuromodulation Corporation*, Case No. 3:16-cv-06830-VC-MEJ, filed Apr. 26, 2018, 1 page.
Exhibit 10 for Declaration of Clara W. Wang in Support of Boston Scientific's Responsive regarding Claim Construction Brief; Opposition to Nevro's Motion for Summary Judgement and Opening Motion for Summary Judgement (Document 358-16), Videotaped Deposition of Rafael Carbunaru, Ph.D., taken on Nov. 15, 2017, *Nevro Corp. vs. Boston Scientific Corporation and Boston Scientific Neuromodulation Corporation*, Case No. 3:16-cv-06830-VC-MEJ, filed Apr. 26, 2018, 9 pages.
Exhibit 11 for Declaration of Clara W. Wang in Support of Boston Scientific's Responsive regarding Claim Construction Brief; Opposition to Nevro's Motion for Summary Judgement and Opening Motion for Summary Judgement (Document 358-17), Redacted Version of Document Sought to be Filed under Sealed—Videotaped Deposition of Jim Cassidy, taken on Nov. 29, 2017, *Nevro Corp. vs. Boston Scientific Corporation and Boston Scientific Neuromodulation Corporation*, Case No. 3:16-cv-06830-VC-MEJ, filed Apr. 26, 2018, 9 pages.
Exhibit 12 for Declaration of Clara W. Wang in Support of Boston Scientific's Responsive regarding Claim Construction Brief; Opposition to Nevro's Motion for Summary Judgement and Opening Motion for Summary Judgement (Document 467), Filed under Sealed—Videotaped Deposition of Kaoru Lee Adair, taken on Nov. 17, 2017, *Nevro Corp. vs. Boston Scientific Corporation and Boston Scientific Neuromodulation Corporation*, Case No. 3:16-cv-06830-VC-MEJ, filed Apr. 26, 2018, 10 pages.
Exhibit 13 for Declaration of Clara W. Wang in Support of Boston Scientific's Responsive regarding Claim Construction Brief; Opposition to Nevro's Motion for Summary Judgement and Opening Motion for Summary Judgement (Document 358-19), Redacted Version of Document Sought to be Filed under Seal—Videotaped Deposition of Jim Cassidy, taken on Nov. 30, 2017, *Nevro Corp. vs. Boston Scientific Corporation and Boston Scientific Neuromodulation Corporation*, Case No. 3:16-cv-06830-VC-MEJ, filed Apr. 26, 2018, 10 pages.
Exhibit 14 for Declaration of Clara W. Wang in Support of Boston Scientific's Responsive regarding Claim Construction Brief; Opposition to Nevro's Motion for Summary Judgement and Opening Motion for Summary Judgement (Document 358-20), Apr. 2018 Email between K. Carter and MoFo-NevroBSX, taken on Nov. 30, 2017, *Nevro Corp. vs. Boston Scientific Corporation and Boston Scientific Neuromodulation Corporation*, Case No. 3:16-cv-06830-VC-MEJ, filed Apr. 26, 2018, 2 pages.
Exhibit 15 for Declaration of Clara W. Wang in Support of Boston Scientific's Responsive regarding Claim Construction Brief; Opposition to Nevro's Motion for Summary Judgement and Opening Motion for Summary Judgement (Document 358-21), Boston Scientific Advancing Science for Life—Technical Sales Training, *Nevro Corp. vs. Boston Scientific Corporation and Boston Scientific Neuromodulation Corporation*, Case No. 3:16-cv-06830-VC-MEJ, filed Apr. 26, 2018, 3 pages.
Exhibit 16 for Declaration of Clara W. Wang in Support of Boston Scientific's Responsive regarding Claim Construction Brief; Opposition to Nevro's Motion for Summary Judgement and Opening Motion for Summary Judgement (Document 358-22), Product Speci-

(56) References Cited

OTHER PUBLICATIONS fication for Ninja System, *Nevro Corp. vs. Boston Scientific Corporation and Boston Scientific Neuromodulation Corporation*, Case No. 3:16-cv-06830-VC-MEJ, filed Apr. 26, 2018, 3 pages.
Exhibit 17 for Declaration of Clara W. Wang in Support of Boston Scientific's Responsive regarding Claim Construction Brief; Opposition to Nevro's Motion for Summary Judgement and Opening Motion for Summary Judgement (Document 358-23), Deposition of Ben Pless, taken on Apr. 10, 2018, *Nevro Corp. vs. Boston Scientific Corporation and Boston Scientific Neuromodulation Corporation*, Case No. 3:16-cv-06830-VC-MEJ, filed Apr. 26, 2018, 3 pages.
Exhibit 18 for Declaration of Clara W. Wang in Support of Boston Scientific's Responsive regarding Claim Construction Brief; Opposition to Nevro's Motion for Summary Judgement and Opening Motion for Summary Judgement (Document 358-24), Merriam-Webster's Collegiate Dictionary, *Nevro Corp. vs. Boston Scientific Corporation and Boston Scientific Neuromodulation Corporation*, Case No. 3:16-cv-06830-VC-MEJ, filed Apr. 26, 2018, 5 pages.
Exhibit 19 for Declaration of Clara W. Wang in Support of Boston Scientific's Responsive regarding Claim Construction Brief; Opposition to Nevro's Motion for Summary Judgement and Opening Motion for Summary Judgement (Document 358-25), Merriam-Webster's Collegiate Dictionary, *Nevro Corp. vs. Boston Scientific Corporation and Boston Scientific Neuromodulation Corporation*, Case No. 3:16-cv-06830-VC-MEJ, filed Apr. 26, 2018, 5 pages.
Exhibit 20 for Declaration of Clara W. Wang in Support of Boston Scientific's Responsive regarding Claim Construction Brief; Opposition to Nevro's Motion for Summary Judgement and Opening Motion for Summary Judgement (Document 358-26), Concise Oxford Dictionary, *Nevro Corp. vs. Boston Scientific Corporation and Boston Scientific Neuromodulation Corporation*, Case No. 3:16-cv-06830-VC-MEJ, filed Apr. 26, 2018, 5 pages.
Exhibit 21 for Declaration of Clara W. Wang in Support of Boston Scientific's Responsive regarding Claim Construction Brief; Opposition to Nevro's Motion for Summary Judgement and Opening Motion for Summary Judgement (Document 358-27), Final Office Action for U.S. Appl. No. 15/134,285, dated Nov. 28, 2017, *Nevro Corp. vs. Boston Scientific Corporation and Boston Scientific Neuromodulation Corporation*, Case No. 3:16-cv-06830-VC-MEJ, filed Apr. 26, 2018, 22 pages.
Exhibit 22 for Declaration of Clara W. Wang in Support of Boston Scientific's Responsive regarding Claim Construction Brief; Opposition to Nevro's Motion for Summary Judgement and Opening Motion for Summary Judgement (Document 358-28), U.S. Pat. No. 8,355,797 by Caparso et al., *Nevro Corp. vs. Boston Scientific Corporation and Boston Scientific Neuromodulation Corporation*, Case No. 3:16-cv-06830-VC-MEJ, filed Apr. 26, 2018, 21 pages.
Exhibit 23 for Declaration of Clara W. Wang in Support of Boston Scientific's Responsive regarding Claim Construction Brief; Opposition to Nevro's Motion for Summary Judgement and Opening Motion for Summary Judgement (Document 358-29), Redacted Version of the Document Sought to be Filed under Seal—Deposition of Jon Parker dated Nov. 16, 2017, *Nevro Corp. vs. Boston Scientific Corporation and Boston Scientific Neuromodulation Corporation*, Case No. 3:16-cv-06830-VC-MEJ, filed Apr. 26, 2018, 12 pages.
Exhibit 24 for Declaration of Clara W. Wang in Support of Boston Scientific's Responsive regarding Claim Construction Brief; Opposition to Nevro's Motion for Summary Judgement and Opening Motion for Summary Judgement (Document 358-30), Redacted Version of the Document Sought to be Filed under Seal—Corrected Rebuttal Expert Report of Ben Plesss regarding Validity dated Mar. 5, 2018, *Nevro Corp. vs. Boston Scientific Corporation and Boston Scientific Neuromodulation Corporation*, Case No. 3:16-cv-06830-VC-MEJ, filed Apr. 26, 2018, 55 pages.
Exhibit 25 for Declaration of Clara W. Wang in Support of Boston Scientific's Responsive regarding Claim Construction Brief; Opposition to Nevro's Motion for Summary Judgement and Opening Motion for Summary Judgement (Document 358-31), Deposition of Dr. Gene Fridman dated Mar. 7, 2018, *Nevro Corp. vs. Boston Scientific Corporation and Boston Scientific Neuromodulation Corporation*, Case No. 3:16-cv-06830-VC-MEJ, filed Apr. 26, 2018, 14 pages.
Exhibit 26 for Declaration of Clara W. Wang in Support of Boston Scientific's Responsive regarding Claim Construction Brief; Opposition to Nevro's Motion for Summary Judgement and Opening Motion for Summary Judgement (Document 358-32), Redacted Version of Document Sought to be Filed under Seal—Opening Expert Report of Ben Pless regarding Infringement dated Jan. 18, 2018, *Nevro Corp. vs. Boston Scientific Corporation and Boston Scientific Neuromodulation Corporation*, Case No. 3:16-cv-06830-VC-MEJ, filed Apr. 26, 2018, 23 pages.
Exhibit 27 for Declaration of Clara W. Wang in Support of Boston Scientific's Responsive regarding Claim Construction Brief; Opposition to Nevro's Motion for Summary Judgement and Opening Motion for Summary Judgement (Document 358-33), U.S. Patent Application Publication No. 2017/0050021 to Cosman Sr., *Nevro Corp. vs. Boston Scientific Corporation and Boston Scientific Neuromodulation Corporation*, Case No. 3:16-cv-06830-VC-MEJ, filed Apr. 26, 2018, 32 pages.
Exhibit 28 for Declaration of Clara W. Wang in Support of Boston Scientific's Responsive regarding Claim Construction Brief; Opposition to Nevro's Motion for Summary Judgement and Opening Motion for Summary Judgement (Document 358-34), Expert Report of William S. Rosenberg, Md, Faans, dated Jan. 18, 2018, *Nevro Corp. vs. Boston Scientific Corporation and Boston Scientific Neuromodulation Corporation*, Case No. 3:16-cv-06830-VC-MEJ, filed Apr. 26, 2018, 4 pages.
Exhibit 29 for Declaration of Clara W. Wang in Support of Boston Scientific's Responsive regarding Claim Construction Brief; Opposition to Nevro's Motion for Summary Judgement and Opening Motion for Summary Judgement (Document 358-35), Declaration of David Caraway, M.D. Ph.D., dated Feb. 16, 2016, *Nevro Corp. vs. Boston Scientific Corporation and Boston Scientific Neuromodulation Corporation*, Case No. 3:16-cv-06830-VC-MEJ, filed Apr. 26, 2018, 8 pages.
Exhibit 30 for Declaration of Clara W. Wang in Support of Boston Scientific's Responsive regarding Claim Construction Brief; Opposition to Nevro's Motion for Summary Judgement and Opening Motion for Summary Judgement (Document 358-36), Filed under Seal—Document NEVRO_BSXCA0073295-300, *Nevro Corp. vs. Boston Scientific Corporation and Boston Scientific Neuromodulation Corporation*, Case No. 3:16-cv-06830-VC-MEJ, filed Apr. 26, 2018, 1 page.
Exhibit 31 for Declaration of Clara W. Wang in Support of Boston Scientific's Responsive regarding Claim Construction Brief; Opposition to Nevro's Motion for Summary Judgement and Opening Motion for Summary Judgement (Document 358-37), Article by Alexander J.R. Macdonald et al., *Nevro Corp. vs. Boston Scientific Corporation and Boston Scientific Neuromodulation Corporation*, Case No. 3:16-cv-06830-VC-MEJ, filed Apr. 26, 2018, 10 pages.
Exhibit 32 for Declaration of Clara W. Wang in Support of Boston Scientific's Responsive regarding Claim Construction Brief; Opposition to Nevro's Motion for Summary Judgement and Opening Motion for Summary Judgement (Document 358-38), U.S. Pat. No. 5,776,170 to MacDonald et al., *Nevro Corp. vs. Boston Scientific Corporation and Boston Scientific Neuromodulation Corporation*, Case No. 3:16-cv-06830-VC-MEJ, filed Apr. 26, 2018, 12 pages.
Exhibit 33 for Declaration of Clara W. Wang in Support of Boston Scientific's Responsive regarding Claim Construction Brief; Opposition to Nevro's Motion for Summary Judgement and Opening Motion for Summary Judgement (Document 358-39), File History for U.S. Appl. No. 14/525,134, issued Mar. 12, 2015, *Nevro Corp. vs. Boston Scientific Corporation and Boston Scientific Neuromodulation Corporation*, Case No. 3:16-cv-06830-VC-MEJ, filed Apr. 26, 2018, 34 pages.
Exhibit 34 for Declaration of Clara W. Wang in Support of Boston Scientific's Responsive regarding Claim Construction Brief; Opposition to Nevro's Motion for Summary Judgement and Opening Motion for Summary Judgement (Document 358-40), Filed under Seal—Document NEVRO_BSXCA0108347-8, *Nevro Corp. vs. Bos-*

(56) References Cited

OTHER PUBLICATIONS ton Scientific Corporation and Boston Scientific Neuromodulation Corporation, Case No. 3:16-cv-06830-VC-MEJ, filed Apr. 26, 2018, 1 page.

Boston Scientific's Responsive Claim Construction Brief, Opposition to in Nevro's Motion for Summary Judgment and Opening Motion for Summary Judgment (Document 358), *Nevro Corp. vs. Boston Scientific Corporation and Boston Scientific Neuromodulation Corporation*, Case No. 3:16-cv-06830-VC-MEJ, filed Apr. 26, 2018, 60 pages.

Exhibit 35 for Declaration of Clara W. Wang in Support of Boston Scientific's Responsive regarding Claim Construction Brief; Opposition to Nevro's Motion for Summary Judgement and Opening Motion for Summary Judgement (Document 358-41), Non-Final Office Action for U.S. Appl. No. 14/503,259, dated Dec. 3, 2015, *Nevro Corp. vs. Boston Scientific Corporation and Boston Scientific Neuromodulation Corporation*, Case No. 3:16-cv-06830-VC-MEJ, filed Apr. 26, 2018, 11 pages.

Exhibit 36 for Declaration of Clara W. Wang in Support of Boston Scientific's Responsive regarding Claim Construction Brief; Opposition to Nevro's Motion for Summary Judgement and Opening Motion for Summary Judgement (Document 358-42), Documents from File History for U.S. Appl. No. 14/261,369, *Nevro Corp. vs. Boston Scientific Corporation and Boston Scientific Neuromodulation Corporation*, Case No. 3:16-cv-06830-VC-MEJ, filed Apr. 26, 2018, 59 pages.

Exhibit 37 for Declaration of Clara W. Wang in Support of Boston Scientific's Responsive regarding Claim Construction Brief; Opposition to Nevro's Motion for Summary Judgement and Opening Motion for Summary Judgement (Document 358-43), Final Office Action for U.S. Appl. No. 15/134,285, dated Nov. 28, 2017, *Nevro Corp. vs. Boston Scientific Corporation and Boston Scientific Neuromodulation Corporation*, Case No. 3:16-cv-06830-VC-MEJ, filed Apr. 26, 2018, 22 pages.

Exhibit 38 for Declaration of Clara W. Wang in Support of Boston Scientific's Responsive regarding Claim Construction Brief; Opposition to Nevro's Motion for Summary Judgement and Opening Motion for Summary Judgement (Document 358-44), U.S. National Library of Medicine—ClinicalTrials.gov, *Nevro Corp. vs. Boston Scientific Corporation and Boston Scientific Neuromodulation Corporation*, Case No. 3:16-cv-06830-VC-MEJ, filed Apr. 26, 2018, 6 pages.

Exhibit 39 for Declaration of Clara W. Wang in Support of Boston Scientific's Responsive regarding Claim Construction Brief; Opposition to Nevro's Motion for Summary Judgement and Opening Motion for Summary Judgement (Document 358-45), Redacted Version of Document Sought to be Filed under Seal—Jan. 23, 2014 Correspondence to Boston Scientific Corporation, *Nevro Corp. vs. Boston Scientific Corporation and Boston Scientific Neuromodulation Corporation*, Case No. 3:16-cv-06830-VC-MEJ, filed Apr. 26, 2018, 10 pages.

Exhibit 40 for Declaration of Clara W. Wang in Support of Boston Scientific's Responsive regarding Claim Construction Brief; Opposition to Nevro's Motion for Summary Judgement and Opening Motion for Summary Judgement (Document 358-46), Redacted Version of Document Sought to be Filed under Seal—Nov. 23, 2016 Email and Correspondence to Kaoru Adair, *Nevro Corp. vs. Boston Scientific Corporation and Boston Scientific Neuromodulation Corporation*, Case No. 3:16-cv-06830-VC-MEJ, filed Apr. 26, 2018, 8 pages.

Exhibit 41 for Declaration of Clara W. Wang in Support of Boston Scientific's Responsive regarding Claim Construction Brief; Opposition to Nevro's Motion for Summary Judgement and Opening Motion for Summary Judgement (Document 358-47), Boston Scientific—Investigational Device Exemption (IDE) Application, submission date Feb. 21, 2013, *Nevro Corp. vs. Boston Scientific Corporation and Boston Scientific Neuromodulation Corporation*, Case No. 3:16-cv-06830-VC-MEJ, filed Apr. 26, 2018, 5 pages.

Exhibit 42 for Declaration of Clara W. Wang in Support of Boston Scientific's Responsive regarding Claim Construction Brief; Opposition to Nevro's Motion for Summary Judgement and Opening Motion for Summary Judgement (Document 358-48), Redacted Version of Document Sought to be Filed under Seal—Boston Scientific—A Randomized Controlled Study to Evaluate the Safety and Effectiveness of the Precision Spinal Cord Stimulator System Adapted for High-Rate Spinal Cord Stimulation, *Nevro Corp. vs. Boston Scientific Corporation and Boston Scientific Neuromodulation Corporation*, Case No. 3:16-cv-06830-VC-MEJ, filed Apr. 26, 2018, 5 pages.

Exhibit 43 for Declaration of Clara W. Wang in Support of Boston Scientific's Responsive regarding Claim Construction Brief; Opposition to Nevro's Motion for Summary Judgement and Opening Motion for Summary Judgement (Document 358-49), World Medical Association—WMA Declaration of Helsinki—Ethical Principles for Medical Research Involving Human Subjects, *Nevro Corp. vs. Boston Scientific Corporation and Boston Scientific Neuromodulation Corporation*, Case No. 3:16-cv-06830-VC-MEJ, filed Apr. 26, 2018, 3 pages.

Exhibit 44 for Declaration of Clara W. Wang in Support of Boston Scientific's Responsive regarding Claim Construction Brief; Opposition to Nevro's Motion for Summary Judgement and Opening Motion for Summary Judgement (Document 358-50), U.S. Patent Application Publication No. 2007/0073354 to Knudson et al., *Nevro Corp. vs. Boston Scientific Corporation and Boston Scientific Neuromodulation Corporation*, Case No. 3:16-cv-06830-VC-MEJ, filed Apr. 26, 2018, 15 pages.

Exhibit 45 for Declaration of Clara W. Wang in Support of Boston Scientific's Responsive regarding Claim Construction Brief; Opposition to Nevro's Motion for Summary Judgement and Opening Motion for Summary Judgement (Document 358-51), U.S. Patent Application Publication No. 2007/0060954 to Cameron et al., *Nevro Corp. vs. Boston Scientific Corporation and Boston Scientific Neuromodulation Corporation*, Case No. 3:16-cv-06830-VC-MEJ, filed Apr. 26, 2018, 21 pages.

Exhibit 46 for Declaration of Clara W. Wang in Support of Boston Scientific's Responsive regarding Claim Construction Brief; Opposition to Nevro's Motion for Summary Judgement and Opening Motion for Summary Judgement (Document 358-52), Documents from File History for U.S. Appl. No. 12/765,747, *Nevro Corp. vs. Boston Scientific Corporation and Boston Scientific Neuromodulation Corporation*, Case No. 3:16-cv-06830-VC-MEJ, filed Apr. 26, 2018, 57 pages.

Exhibit 47 for Declaration of Clara W. Wang in Support of Boston Scientific's Responsive regarding Claim Construction Brief; Opposition to Nevro's Motion for Summary Judgement and Opening Motion for Summary Judgement (Document 358-53), Response to Final Office Action for U.S. Appl. No. 14/292,671, filed Jan. 17, 2017, *Nevro Corp. vs. Boston Scientific Corporation and Boston Scientific Neuromodulation Corporation*, Case No. 3:16-cv-06830-VC-MEJ, filed Apr. 26, 2018, 12 pages.

Exhibit 48 for Declaration of Clara W. Wang in Support of Boston Scientific's Responsive regarding Claim Construction Brief; Opposition to Nevro's Motion for Summary Judgement and Opening Motion for Summary Judgement (Document 358-54), Response to Non-Final Office Action for U.S. Appl. No. 14/503,259, filed Mar. 16, 2015, *Nevro Corp. vs. Boston Scientific Corporation and Boston Scientific Neuromodulation Corporation*, Case No. 3:16-cv-06830-VC-MEJ, filed Apr. 26, 2018, 30 pages.

Exhibit 49 for Declaration of Clara W. Wang in Support of Boston Scientific's Responsive regarding Claim Construction Brief; Opposition to Nevro's Motion for Summary Judgement and Opening Motion for Summary Judgement (Document 358-55), Redacted Version of Document Sought to be Filed under Seal—Deposition of Konstantinos Alataris dated Nov. 14, 2017, *Nevro Corp. vs. Boston Scientific Corporation and Boston Scientific Neuromodulation Corporation*, Case No. 3:16-cv-06830-VC-MEJ, filed Apr. 26, 2018, 21 pages.

Exhibit 50 for Declaration of Clara W. Wang in Support of Boston Scientific's Responsive regarding Claim Construction Brief; Opposition to Nevro's Motion for Summary Judgement and Opening Motion for Summary Judgement (Document 358-56), Chart for Asserted Claims by Limitation Category, *Nevro Corp. vs. Boston*

(56) References Cited

OTHER PUBLICATIONS

*Scientific Corporation and Boston Scientific Neuromodulation Corporation*, Case No. 3:16-cv-06830-VC-MEJ, filed Apr. 26, 2018, 12 pages.
Exhibit 51 for Declaration of Clara W. Wang in Support of Boston Scientific's Responsive regarding Claim Construction Brief; Opposition to Nevro's Motion for Summary Judgement and Opening Motion for Summary Judgement (Document 358-57), U.S. Patent Application Publication No. 2009/0204173 to Fang et al., *Nevro Corp. vs. Boston Scientific Corporation and Boston Scientific Neuromodulation Corporation*, Case No. 3:16-cv-06830-VC-MEJ, filed Apr. 26, 2018, 33 pages.
Exhibit 52 for Declaration of Clara W. Wang in Support of Boston Scientific's Responsive regarding Claim Construction Brief; Opposition to Nevro's Motion for Summary Judgement and Opening Motion for Summary Judgement (Document 358-58), Applicant-Initiated Interview Summary for U.S. Appl. No. 14/037,262, dated Feb. 25, 2014, *Nevro Corp. vs. Boston Scientific Corporation and Boston Scientific Neuromodulation Corporation*, Case No. 3:16-cv-06830-VC-MEJ, filed Apr. 26, 2018, 5 pages.
Exhibit 53 for Declaration of Clara W. Wang in Support of Boston Scientific's Responsive regarding Claim Construction Brief; Opposition to Nevro's Motion for Summary Judgement and Opening Motion for Summary Judgement (Document 358-59), Redacted Version of Document Sought to be Filed under Seal—Videotaped Deposition of Zi-Ping Fang dated Nov. 2, 2017, *Nevro Corp. vs. Boston Scientific Corporation and Boston Scientific Neuromodulation Corporation*, Case No. 3:16-cv-06830-VC-MEJ, filed Apr. 26, 2018, 16 pages.
Exhibit 54 for Declaration of Clara W. Wang in Support of Boston Scientific's Responsive regarding Claim Construction Brief; Opposition to Nevro's Motion for Summary Judgement and Opening Motion for Summary Judgement (Document 358-60), Handwritten Figure, *Nevro Corp. vs. Boston Scientific Corporation and Boston Scientific Neuromodulation Corporation*, Case No. 3:16-cv-06830-VC-MEJ, filed Apr. 26, 2018, 3 pages.
Exhibit 55 for Declaration of Clara W. Wang in Support of Boston Scientific's Responsive regarding Claim Construction Brief; Opposition to Nevro's Motion for Summary Judgement and Opening Motion for Summary Judgement (Document 358-61), Handwritten Figure, *Nevro Corp. vs. Boston Scientific Corporation and Boston Scientific Neuromodulation Corporation*, Case No. 3:16-cv-06830-VC-MEJ, filed Apr. 26, 2018, 3 pages.
Exhibit 56 for Declaration of Clara W. Wang in Support of Boston Scientific's Responsive regarding Claim Construction Brief; Opposition to Nevro's Motion for Summary Judgement and Opening Motion for Summary Judgement (Document 358-62), Declaration of Rafael Cabunaru in Support of Boston Scientific's Invalidity Contentions, *Nevro Corp. vs. Boston Scientific Corporation and Boston Scientific Neuromodulation Corporation*, Case No. 3:16-cv-06830-VC-MEJ, filed Apr. 26, 2018, 132 pages.
Exhibit 57 for Declaration of Clara W. Wang in Support of Boston Scientific's Responsive regarding Claim Construction Brief; Opposition to Nevro's Motion for Summary Judgement and Opening Motion for Summary Judgement (Document 358-63), Deposition of David Caraway, M.D., Ph.D., dated Nov. 14, 2017, *Nevro Corp. vs. Boston Scientific Corporation and Boston Scientific Neuromodulation Corporation*, Case No. 3:16-cv-06830-VC-MEJ, filed Apr. 26, 2018, 15 pages.
Exhibit 58 for Declaration of Clara W. Wang in Support of Boston Scientific's Responsive regarding Claim Construction Brief; Opposition to Nevro's Motion for Summary Judgement and Opening Motion for Summary Judgement (Document 358-64), Filed under Seal—Document NEVRO_BSXCA0209790-812, *Nevro Corp. vs. Boston Scientific Corporation and Boston Scientific Neuromodulation Corporation*, Case No. 3:16-cv-06830-VC-MEJ, filed Apr. 26, 2018, 1 page.
Exhibit 59 for Declaration of Clara W. Wang in Support of Boston Scientific's Responsive regarding Claim Construction Brief; Opposition to Nevro's Motion for Summary Judgement and Opening Motion for Summary Judgement (Document 358-65), Videotaped Deposition of Dr. James North taken on Nov. 18, 2017, *Nevro Corp. vs. Boston Scientific Corporation and Boston Scientific Neuromodulation Corporation*, Case No. 3:16-cv-06830-VC-MEJ, filed Apr. 26, 2018, 11 pages.
Exhibit 60 for Declaration of Clara W. Wang in Support of Boston Scientific's Responsive regarding Claim Construction Brief; Opposition to Nevro's Motion for Summary Judgement and Opening Motion for Summary Judgement (Document 358-66), Videotaped Deposition of Robert Nathan taken on Nov. 15, 2017, *Nevro Corp. vs. Boston Scientific Corporation and Boston Scientific Neuromodulation Corporation*, Case No. 3:16-cv-06830-VC-MEJ, filed Apr. 26, 2018, 11 pages.
Exhibit 61 for Declaration of Clara W. Wang in Support of Boston Scientific's Responsive regarding Claim Construction Brief; Opposition to Nevro's Motion for Summary Judgement and Opening Motion for Summary Judgement (Document 358-67), Case Report by Yearwood et al., *Nevro Corp. vs. Boston Scientific Corporation and Boston Scientific Neuromodulation Corporation*, Case No. 3:16-cv-06830-VC-MEJ, filed Apr. 26, 2018, 3 pages.
Exhibit 62 for Declaration of Clara W. Wang in Support of Boston Scientific's Responsive regarding Claim Construction Brief; Opposition to Nevro's Motion for Summary Judgement and Opening Motion for Summary Judgement (Document 358-68), Videotaped Deposition of Dr. William S. Rosenberg dated Mar. 21, 2018, *Nevro Corp. vs. Boston Scientific Corporation and Boston Scientific Neuromodulation Corporation*, Case No. 3:16-cv-06830-VC-MEJ, filed Apr. 26, 2018, 11 pages.
Exhibit 63 for Declaration of Clara W. Wang in Support of Boston Scientific's Responsive regarding Claim Construction Brief; Opposition to Nevro's Motion for Summary Judgement and Opening Motion for Summary Judgement (Document 358-69), Document by Yearwood et al., *Nevro Corp. vs. Boston Scientific Corporation and Boston Scientific Neuromodulation Corporation*, Case No. 3:16-cv-06830-VC-MEJ, filed Apr. 26, 2018, 8 pages.
Exhibit 64 for Declaration of Clara W. Wang in Support of Boston Scientific's Responsive regarding Claim Construction Brief; Opposition to Nevro's Motion for Summary Judgement and Opening Motion for Summary Judgement (Document 358-70), Redacted Version of Document Sought to be Filed under Seal—Videotaped Deposition of James Thacker (vol. I) dated Dec. 7, 2017, *Nevro Corp. vs. Boston Scientific Corporation and Boston Scientific Neuromodulation Corporation*, Case No. 3:16-cv-06830-VC-MEJ, filed Apr. 26, 2018, 35 pages.
Exhibit 65 for Declaration of Clara W. Wang in Support of Boston Scientific's Responsive regarding Claim Construction Brief; Opposition to Nevro's Motion for Summary Judgement and Opening Motion for Summary Judgement (Document 358-71), Filed under Seal—Document NEVRO_BSXCA0118164-203, *Nevro Corp. vs. Boston Scientific Corporation and Boston Scientific Neuromodulation Corporation*, Case No. 3:16-cv-06830-VC-MEJ, filed Apr. 26, 2018, 1 page.
Exhibit 66 for Declaration of Clara W. Wang in Support of Boston Scientific's Responsive regarding Claim Construction Brief; Opposition to Nevro's Motion for Summary Judgement and Opening Motion for Summary Judgement (Document 358-72), Videotaped Deposition of Kerry Bradley dated Nov. 8, 2017, *Nevro Corp. vs. Boston Scientific Corporation and Boston Scientific Neuromodulation Corporation*, Case No. 3:16-cv-06830-VC-MEJ, filed Apr. 26, 2018, 10 pages.
Exhibit 67 for Declaration of Clara W. Wang in Support of Boston Scientific's Responsive regarding Claim Construction Brief; Opposition to Nevro's Motion for Summary Judgement and Opening Motion for Summary Judgement (Document 358-73), Response to Final Office Action for U.S. Appl. No. 12/765,685, filed Sep. 19, 2013, *Nevro Corp. vs. Boston Scientific Corporation and Boston Scientific Neuromodulation Corporation*, Case No. 3:16-cv-06830-VC-MEJ, filed Apr. 26, 2018, 15 pages.
Exhibit 68 for Declaration of Clara W. Wang in Support of Boston Scientific's Responsive regarding Claim Construction Brief; Opposition to Nevro's Motion for Summary Judgement and Opening Motion for Summary Judgement (Document 358-74), Response to Non-Final Office Action for U.S. Appl. No. 13/830,992, filed Feb.

(56) References Cited

OTHER PUBLICATIONS 24, 2014, *Nevro Corp. vs. Boston Scientific Corporation and Boston Scientific Neuromodulation Corporation*, Case No. 3:16-cv-06830-VC-MEJ, filed Apr. 26, 2018, 15 pages.
Rebuttal Expert Report and Declaration of Daniel Lanovaz (Document 359), *Nevro Corp. vs. Boston Scientific Corporation and Boston Scientific Neuromodulation Corporation*, Case No. 3:16-cv-06830-VC-MEJ, filed Apr. 26, 2018, 10 pages.
Nevro's Reply in Support of its Motion for Summary Adjudication and Opposition to BSC's Motion for Summary Judgement (Document 468), Updated Redacted Version of ECF No. 382-2, *Nevro Corp. vs. Boston Scientific Corporation and Boston Scientific Neuromodulation Corporation*, Case No. 3:16-cv-06830-VC-MEJ, filed Jul. 30, 2018, 40 pages.
Declaration of Joshua Goshorn in Support of Nevro's Reply in Support of Motion for Summary Adjudication and Opposition to BSC's Motion for Summary Judgement (Document 375), *Nevro Corp. vs. Boston Scientific Corporation and Boston Scientific Neuromodulation Corporation*, Case No. 3:16-cv-06830-VC-MEJ, filed May 10, 2018, 2 pages.
Exhibit A for Declaration of Joshua Goshorn in Support of Nevro's Reply in Support of Motion for Summary Adjudication and Opposition to BSC's Motion for Summary Judgement (Document 375-1), Entire Document Sought—Joshua Goshorn opening Expert Report, *Nevro Corp. vs. Boston Scientific Corporation and Boston Scientific Neuromodulation Corporation*, Case No. 3:16-cv-06830-VC-MEJ, filed May 10, 2018, 1 page.
Declaration of Ben Pless in Support of Nevro's Reply in Support of Motion for Summary Adjudication and Opposition to BSC's Motion for Summary Judgement (Document 376), *Nevro Corp. vs. Boston Scientific Corporation and Boston Scientific Neuromodulation Corporation*, Case No. 3:16-cv-06830-VC-MEJ, filed May 10, 2018, 2 pages.
Exhibit A for Declaration of Ben Pless in Support of Nevro's Reply in Support of Motion for Summary Adjudication and Opposition to BSC's Motion for Summary Judgement (Document 376-1), Redacted Version of Document Sought to be Sealed—Opening Expert Report of Ben Pless, *Nevro Corp. vs. Boston Scientific Corporation and Boston Scientific Neuromodulation Corporation*, Case No. 3:16-cv-06830-VC-MEJ, filed May 10, 2018, 151 pages.
Exhibit B for Declaration of Ben Pless in Support of Nevro's Reply in Support of Motion for Summary Adjudication and Opposition to BSC's Motion for Summary Judgement (Document 376-2), Redacted Version of Document Sought to be Sealed—Corrected Rebuttal Expert Report of Ben Pless regarding Validity, dated Mar. 5, 2018, *Nevro Corp. vs. Boston Scientific Corporation and Boston Scientific Neuromodulation Corporation*, Case No. 3:16-cv-06830-VC-MEJ, filed May 10, 2018, 116 pages.
Declaration of William Sanford Rosenberg in Support of Nevro's Reply in Support of Motion for Summary Adjudication and Opposition to BSC's Motion for Summary Judgement (Document 377), *Nevro Corp. vs. Boston Scientific Corporation and Boston Scientific Neuromodulation Corporation*, Case No. 3:16-cv-06830-VC-MEJ, filed May 10, 2018, 2 pages.
Exhibit A for Declaration of William Sanford Rosenberg in Support of Nevro's Reply in Support of Motion for Summary Adjudication and Opposition to BSC's Motion for Summary Judgement (Document 377-1), Curriculum Vitae of William Sanford Rosenberg, M.D., *Nevro Corp. vs. Boston Scientific Corporation and Boston Scientific Neuromodulation Corporation*, Case No. 3:16-cv-06830-VC-MEJ, filed May 10, 2018, 21 pages.
Exhibit B for Declaration of William Sanford Rosenberg in Support of Nevro's Reply in Support of Motion for Summary Adjudication and Opposition to BSC's Motion for Summary Judgement (Document 377-2), Redacted Version of Document Sought to be Sealed—Deposition of William Sanford Rosenberg, M.D. Faams, *Nevro Corp. vs. Boston Scientific Corporation and Boston Scientific Neuromodulation Corporation*, Case No. 3:16-cv-06830-VC-MEJ, filed May 10, 2018, 40 pages.
Declaration of Robert Schiff in Support of Nevro's Reply in Support of Motion for Summary Adjudication and Opposition to BSC's Motion for Summary Judgement (Document 378), *Nevro Corp. vs. Boston Scientific Corporation and Boston Scientific Neuromodulation Corporation*, Case No. 3:16-cv-06830-VC-MEJ, filed May 10, 2018, 2 pages.
Exhibit A—Updated—for Declaration of Robert Schiff in Support of Nevro's Reply in Support of Motion for Summary Adjudication and Opposition to BSC's Motion for Summary Judgement (Document 410), Redacted Version of ECF No. 382-10—Exhibit A to the May 9, 2018 Declaration of Robert Schiff, *Nevro Corp. vs. Boston Sci7ntific Corporation and Boston Scientific Neuromodulation Corporation*, Case No. 3:16-cv-06830-VC-MEJ, filed May 10, 2018, 72 pages.
Declaration of Nicholas Fung in Support of Nevro's Reply in Support of Motion for Summary Adjudication and Opposition to BSC's Motion for Summary Judgement (Document 379), *Nevro Corp. vs. Boston Scientific Corporation and Boston Scientific Neuromodulation Corporation*, Case No. 3:16-cv-06830-VC-MEJ, filed May 10, 2018, 5 pages.
Exhibit 1 for Declaration of Nicholas Fung in Support of Nevro's Reply in Support of Motion for Summary Adjudication and Opposition to BSC's Motion for Summary Judgement (Document 379-1), Claims Chart, *Nevro Corp. vs. Boston Scientific Corporation and Boston Scientific Neuromodulation Corporation*, Case No. 3:16-cv-06830-VC-MEJ, filed May 10, 2018, 3 pages.
Exhibit 2 for Declaration of Nicholas Fung in Support of Nevro's Reply in Support of Motion for Summary Adjudication and Opposition to BSC's Motion for Summary Judgement (Document 379-2), Entire Document Sought to be Sealed—Document BSC-NVRO_00713169-172, *Nevro Corp. vs. Boston Scientific Corporation and Boston Scientific Neuromodulation Corporation*, Case No. 3:16-cv-06830-VC-MEJ, filed May 10, 2018, 1 page.
Exhibit 3 for Declaration of Nicholas Fung in Support of Nevro's Reply in Support of Motion for Summary Adjudication and Opposition to BSC's Motion for Summary Judgement (Document 379-3), Redacted Version of Document Sought to be Sealed—BSC's Second Supplemental Responses and Objections to Nevro's First Set of Interrogatory Request (1-8), *Nevro Corp. vs. Boston Scientific Corporation and Boston Scientific Neuromodulation Corporation*, Case No. 3:16-cv-06830-VC-MEJ, filed May 10, 2018, 13 pages.
Exhibit 4 for Declaration of Nicholas Fung in Support of Nevro's Reply in Support of Motion for Summary Adjudication and Opposition to BSC's Motion for Summary Judgement (Document 379-4), Redacted Version of Document Sought to be Sealed—Videotaped Deposition of Sridhar Kothandaraman, *Nevro Corp. vs. Boston Scientific Corporation and Boston Scientific Neuromodulation Corporation*, Case No. 3:16-cv-06830-VC-MEJ, filed May 10, 2018, 14 pages.
Exhibit 5 for Declaration of Nicholas Fung in Support of Nevro's Reply in Support of Motion for Summary Adjudication and Opposition to BSC's Motion for Summary Judgement (Document 379-5), Videotaped Deposition of Brian Erickson dated Dec. 15, 2017, *Nevro Corp. vs. Boston Scientific Corporation and Boston Scientific Neuromodulation Corporation*, Case No. 3:16-cv-06830-VC-MEJ, filed May 10, 2018, 7 pages.
Exhibit 6 for Declaration of Nicholas Fung in Support of Nevro's Reply in Support of Motion for Summary Adjudication and Opposition to BSC's Motion for Summary Judgement (Document 379-6), Plaintiffs Brief regarding Claim Construction of the "Adapted To" Claim Term, *Nevro Corp. vs. Boston Scientific Corporation and Boston Scientific Neuromodulation Corporation*, Case No. 3:16-cv-06830-VC-MEJ, filed May 10, 2018, 7 pages.
Exhibit 7 for Declaration of Nicholas Fung in Support of Nevro's Reply in Support of Motion for Summary Adjudication and Opposition to BSC's Motion for Summary Judgement (Document 379-7), Plaintiffs Response Brief regarding Claim Construction of the "Adapted To" Claim Term, *Nevro Corp. vs. Boston Scientific Corporation and Boston Scientific Neuromodulation Corporation*, Case No. 3:16-cv-06830-VC-MEJ, filed May 10, 2018, 6 pages.
Exhibit 8 for Declaration of Nicholas Fung in Support of Nevro's Reply in Support of Motion for Summary Adjudication and Opposition to BSC's Motion for Summary Judgement (Document 379-8),

(56) References Cited

OTHER PUBLICATIONS

Deposition of Ben Pless dated Apr. 10, 2018, *Nevro Corp. vs. Boston Scientific Corporation and Boston Scientific Neuromodulation Corporation*, Case No. 3:16-cv-06830-VC-MEJ, filed May 10, 2018, 31 pages.
Exhibit 9 for Declaration of Nicholas Fung in Support of Nevro's Reply in Support of Motion for Summary Adjudication and Opposition to BSC's Motion for Summary Judgement (Document 379-9), Deposition of Dr. Gene Fridman dated Mar. 7, 2018, *Nevro Corp. vs. Boston Scientific Corporation and Boston Scientific Neuromodulation Corporation*, Case No. 3:16-cv-06830-VC-MEJ, filed May 10, 2018, 62 pages.
Exhibit 10 for Declaration of Nicholas Fung in Support of Nevro's Reply in Support of Motion for Summary Adjudication and Opposition to BSC's Motion for Summary Judgement (Document 379-10), Expert Report and Declaration of Gene Fridman, Ph.D., regarding Claim Construction, *Nevro Corp. vs. Boston Scientific Corporation and Boston Scientific Neuromodulation Corporation*, Case No. 3:16-cv-06830-VC-MEJ, filed May 10, 2018, 6 pages.
Exhibit 11 for Declaration of Nicholas Fung in Support of Nevro's Reply in Support of Motion for Summary Adjudication and Opposition to BSC's Motion for Summary Judgement (Document 379-11), Article by Tan et al., *Nevro Corp. vs. Boston Scientific Corporation and Boston Scientific Neuromodulation Corporation*, Case No. 3:16-cv-06830-VC-MEJ, filed May 10, 2018, 8 pages.
Exhibit 12 for Declaration of Nicholas Fung in Support of Nevro's Reply in Support of Motion for Summary Adjudication and Opposition to BSC's Motion for Summary Judgement (Document 379-12), Decision Denying Institution of Inter Partes Review for U.S. Pat. No. 8,359,102 (Case IPR2015-01203), *Nevro Corp. vs. Boston Scientific Corporation and Boston Scientific Neuromodulation Corporation*, Case No. 3:16-cv-06830-VC-MEJ, filed May 10, 2018, 21 pages.
Exhibit 13 for Declaration of Nicholas Fung in Support of Nevro's Reply in Support of Motion for Summary Adjudication and Opposition to BSC's Motion for Summary Judgement (Document 379-13), Certified U.S. Pat. No. 9,327,125, *Nevro Corp. vs. Boston Scientific Corporation and Boston Scientific Neuromodulation Corporation*, Case No. 3:16-cv-06830-VC-MEJ, filed May 10, 2018, 66 pages.
Exhibit 14 for Declaration of Nicholas Fung in Support of Nevro's Reply in Support of Motion for Summary Adjudication and Opposition to BSC's Motion for Summary Judgement (Document 379-14), U.S. Pat. No. 9,492,664, *Nevro Corp. vs. Boston Scientific Corporation and Boston Scientific Neuromodulation Corporation*, Case No. 3:16-cv-06830-VC-MEJ, filed May 10, 2018, 25 pages.
Exhibit 15 for Declaration of Nicholas Fung in Support of Nevro's Reply in Support of Motion for Summary Adjudication and Opposition to BSC's Motion for Summary Judgement (Document 379-15), U.S. Pat. No. 9,339,655, *Nevro Corp. vs. Boston Scientific Corporation and Boston Scientific Neuromodulation Corporation*, Case No. 3:16-cv-06830-VC-MEJ, filed May 10, 2018, 23 pages.
Exhibit 16 for Declaration of Nicholas Fung in Support of Nevro's Reply in Support of Motion for Summary Adjudication and Opposition to BSC's Motion for Summary Judgement (Document 379-16), Redacted Version of Document Sought to be Sealed—Videotaped Deposition of Richard T. Mihran, Ph.D., dated Mar. 12, 2018, *Nevro Corp. vs. Boston Scientific Corporation and Boston Scientific Neuromodulation Corporation*, Case No. 3:16-cv-06830-VC-MEJ, filed May 10, 2018, 29 pages.
Exhibit 17 for Declaration of Nicholas Fung in Support of Nevro's Reply in Support of Motion for Summary Adjudication and Opposition to BSC's Motion for Summary Judgement (Document 379-17), Redacted Version of Document Sought to be Sealed—Videotaped Deposition of Jim Cassidy, dated May 17, 2017, *Nevro Corp. vs. Boston Scientific Corporation and Boston Scientific Neuromodulation Corporation*, Case No. 3:16-cv-06830-VC-MEJ, filed May 10, 2018, 13 pages.
Exhibit 18 for Declaration of Nicholas Fung in Support of Nevro's Reply in Support of Motion for Summary Adjudication and Opposition to BSC's Motion for Summary Judgement (Document 379-18), Redacted Version of Document Sought to be Sealed—Deposition of Adam Lipson, M.D., dated Apr. 12, 2018, *Nevro Corp. vs. Boston Scientific Corporation and Boston Scientific Neuromodulation Corporation*, Case No. 3:16-cv-06830-VC-MEJ, filed May 10, 2018, 10 pages.
Exhibit 19 for Declaration of Nicholas Fung in Support of Nevro's Reply in Support of Motion for Summary Adjudication and Opposition to BSC's Motion for Summary Judgement (Document 379-19), Redacted Version of Document Sought to be Sealed—BSC's Nov. 10, 17 Supplemental Responses and Objections to Nevro's Interrogatory Requests Nos. 2, 4, 5, and 7, *Nevro Corp. vs. Boston Scientific Corporation and Boston Scientific Neuromodulation Corporation*, Case No. 3:16-cv-06830-VC-MEJ, filed May 10, 2018, 9 pages.
Exhibit 20 for Declaration of Nicholas Fung in Support of Nevro's Reply in Support of Motion for Summary Adjudication and Opposition to BSC's Motion for Summary Judgement (Document 379-20), Entire Document Sought to be Sealed—Deposition of Kaoru Adair, *Nevro Corp. vs. Boston Scientific Corporation and Boston Scientific Neuromodulation Corporation*, Case No. 3:16-cv-06830-VC-MEJ, filed May 10, 2018, 1 page.
Exhibit 21—Updated—for Declaration of Nicholas Fung in Support of Nevro's Reply in Support of Motion for Summary Adjudication and Opposition to BSC's Motion for Summary Judgement (Document 471), Redacted Version of ECF No. 382-24—Videotaped Deposition of Kaoru Adair dated May 10, 2017, *Nevro Corp. vs. Boston Scientific Corporation and Boston Scientific Neuromodulation Corporation*, Case No. 3:16-cv-06830-VC-MEJ, filed May 10, 2018, 18 pages.
Exhibit 23 for Declaration of Nicholas Fung in Support of Nevro's Reply in Support of Motion for Summary Adjudication and Opposition to BSC's Motion for Summary Judgement (Document 379-23), Entire Document Sought to be Sealed—Document BSC-NVRO_00720938-940, *Nevro Corp. vs. Boston Scientific Corporation and Boston Scientific Neuromodulation Corporation*, Case No. 3:16-cv-06830-VC-MEJ, filed May 10, 2018, 1 page.
Exhibit 24 for Declaration of Nicholas Fung in Support of Nevro's Reply in Support of Motion for Summary Adjudication and Opposition to BSC's Motion for Summary Judgement (Document 379-24), Redacted Version of Document Sought to be Sealed—Deposition of Joshua Goshorn, dated Mar. 23, 2018, *Nevro Corp. vs. Boston Scientific Corporation and Boston Scientific Neuromodulation Corporation*, Case No. 3:16-cv-06830-VC-MEJ, filed May 10, 2018, 15 pages.
Exhibit 25 for Declaration of Nicholas Fung in Support of Nevro's Reply in Support of Motion for Summary Adjudication and Opposition to BSC's Motion for Summary Judgement (Document 379-25), Redacted Version of Document Sought to be Sealed—Videotaped Deposition of Daniel Lanovaz, dated Mar. 21, 2018, *Nevro Corp. vs. Boston Scientific Corporation and Boston Scientific Neuromodulation Corporation*, Case No. 3:16-cv-06830-VC-MEJ, filed May 10, 2018, 11 pages.
Exhibit 26 for Declaration of Nicholas Fung in Support of Nevro's Reply in Support of Motion for Summary Adjudication and Opposition to BSC's Motion for Summary Judgement (Document 379-26), Redacted Version of Document Sought to be Sealed—Rebuttal Expert Report of Richard T. Mihran, Ph.D. dated Feb. 14, 2018, *Nevro Corp. vs. Boston Scientific Corporation and Boston Scientific Neuromodulation Corporation*, Case No. 3:16-cv-06830-VC-MEJ, filed May 10, 2018, 23 pages.
Exhibit 27 for Declaration of Nicholas Fung in Support of Nevro's Reply in Support of Motion for Summary Adjudication and Opposition to BSC's Motion for Summary Judgement (Document 379-27), Expert Report of Richard T. Mihran, Ph.D., regarding Invalidity of U.S. Pat. Nos. 8,712,533; 9,327,125; 8,359,102; 9,480,842; 9,333,357; 8,792,988, and 8,768,472, *Nevro Corp. vs. Boston Scientific Corporation and Boston Scientific Neuromodulation Corporation*, Case No. 3:16-cv-06830-VC-MEJ, filed May 10, 2018, 6 pages.
Exhibit 28 for Declaration of Nicholas Fung in Support of Nevro's Reply in Support of Motion for Summary Adjudication and Opposition to BSC's Motion for Summary Judgement (Document 379-

(56) References Cited

OTHER PUBLICATIONS

28), Declaration of Rafael Carbunaru in Support of Boston Scientific's Invalidity Contentions, *Nevro Corp. vs. Boston Scientific Corporation and Boston Scientific Neuromodulation Corporation*, Case No. 3:16-cv-06830-VC-MEJ, filed May 10, 2018, 13 pages.
Exhibit 29 for Declaration of Nicholas Fung in Support of Nevro's Reply in Support of Motion for Summary Adjudication and Opposition to BSC's Motion for Summary Judgement (Document 379-29), Redacted Version of Document Sought to be Sealed—Videotaped Deposition of Nevro Corp., with designated corporate representative Rafael Carbunaru, dated May 18, 2017, *Nevro Corp. vs. Boston Scientific Corporation and Boston Scientific Neuromodulation Corporation*, Case No. 3:16-cv-06830-VC-MEJ, filed May 10, 2018, 8 pages.
Declaration of Carson D. Anderson in Support of Nevro's Administrative Motion to File under Seal Portions of Nevro's Reply in Support of It's Motion for Summary Adjudication and Opposition to BSC's Motion for Summary Judgement (Document 382), *Nevro Corp. vs. Boston Scientific Corporation and Boston Scientific Neuromodulation Corporation*, Case No. 3:16-cv-06830-VC-MEJ, filed May 14, 2018, 13 pages.
Exhibit A—Updated—for Declaration of Carson D. Anderson in Support of Nevro's Administrative Motion to File under Seal Portions of Nevro's Reply in Support of It's Motion for Summary Adjudication and Opposition to BSC's Motion for Summary Judgement (Document 468), Redacted Version of ECF No. 382-2—Nevro's Reply in Support of its Motion for Summary Adjudication and Opposition to BSC's Motion for Summary Judgment, *Nevro Corp. vs. Boston Scientific Corporation and Boston Scientific Neuromodulation Corporation*, Case No. 3:16-cv-06830-VC-MEJ, filed May 14, 2018, 40 pages.
Exhibit B for Declaration of Carson D. Anderson in Support of Nevro's Administrative Motion to File under Seal Portions of Nevro's Reply in Support of It's Motion for Summary Adjudication and Opposition to BSC's Motion for Summary Judgement (Document 382-3), Redacted Version of Document Sought to be Filed under Seal—Expert Report of Joshua Goshorn, *Nevro Corp. vs. Boston Scientific Corporation and Boston Scientific Neuromodulation Corporation*, Case No. 3:16-cv-06830-VC-MEJ, filed May 14, 2018, 15 pages.
Exhibit C for Declaration of Carson D. Anderson in Support of Nevro's Administrative Motion to File under Seal Portions of Nevro's Reply in Support of It's Motion for Summary Adjudication and Opposition to BSC's Motion for Summary Judgement (Document 382-5), Redacted Version of Document Sought to be Filed under Seal—Expert Report of William S. Rosenberg, M.D., Faans, *Nevro Corp. vs. Boston Scientific Corporation and Boston Scientific Neuromodulation Corporation*, Case No. 3:16-cv-06830-VC-MEJ, filed May 14, 2018, 41 pages.
Exhibit D—Updated—for Declaration of Carson D. Anderson in Support of Nevro's Administrative Motion to File under Seal Portions of Nevro's Reply in Support of It's Motion for Summary Adjudication and Opposition to BSC's Motion for Summary Judgement (Document 469), Redacted Version of ECF No. 382-8—Opening Expert Report of Ben Pless regarding Infringement, dated Jan. 18, 2018, *Nevro Corp. vs. Boston Scientific Corporation and Boston Scientific Neuromodulation Corporation*, Case No. 3:16-cv-06830-VC-MEJ, filed May 14, 2018, 152 pages.
Exhibit E—Updated—for Declaration of Carson D. Anderson in Support of Nevro's Administrative Motion to File under Seal Portions of Nevro's Reply in Support of It's Motion for Summary Adjudication and Opposition to BSC's Motion for Summary Judgement (Document 470), Redacted Version of ECF No. 382-10—Expert Report of Robert Schiff, Ph.D., RAC, CQA, FRAPS, *Nevro Corp. vs. Boston Scientific Corporation and Boston Scientific Neuromodulation Corporation*, Case No. 3:16-cv-06830-VC-MEJ, filed May 14, 2018, 72 pages.
Exhibit F for Declaration of Carson D. Anderson in Support of Nevro's Administrative Motion to File under Seal Portions of Nevro's Reply in Support of It's Motion for Summary Adjudication and Opposition to BSC's Motion for Summary Judgement (Document 382-11), Redacted Version of Document Sought to be Filed under Seal—Cross-Border HCP Arrangement Request, *Nevro Corp. vs. Boston Scientific Corporation and Boston Scientific Neuromodulation Corporation*, Case No. 3:16-cv-06830-VC-MEJ, filed May 14, 2018, 6 pages.
Exhibit G for Declaration of Carson D. Anderson in Support of Nevro's Administrative Motion to File under Seal Portions of Nevro's Reply in Support of It's Motion for Summary Adjudication and Opposition to BSC's Motion for Summary Judgement (Document 382-13), Redacted Version of Document Sought to be Filed under Seal—BSC's Second Supplemental Responses and Objections to Nevro's First Set of Interrogatory Request (1-8), *Nevro Corp. vs. Boston Scientific Corporation and Boston Scientific Neuromodulation Corporation*, Case No. 3:16-cv-06830-VC-MEJ, filed May 14, 2018, 14 pages.
Exhibit H for Declaration of Carson D. Anderson in Support of Nevro's Administrative Motion to File under Seal Portions of Nevro's Reply in Support of It's Motion for Summary Adjudication and Opposition to BSC's Motion for Summary Judgement (Document 382-15), Redacted Version of Document Sought to be Filed under Seal—Videotaped Deposition of Sridhar Kothandaraman, dated Nov. 17, 2017, *Nevro Corp. vs. Boston Scientific Corporation and Boston Scientific Neuromodulation Corporation*, Case No. 3:16-cv-06830-VC-MEJ, filed May 14, 2018, 15 pages.
Exhibit I for Declaration ofCarson D. Anderson in Support of Nevro's Administrative Motion to File under Seal Portions of Nevro's Reply in Support of It's Motion for Summary Adjudication and Opposition to BSC's Motion for Summary Judgement (Document 382-17), Redacted Version of Document Sought to be Filed under Seal—Videotaped Deposition of Richard T. Mihran, dated Mar. 12, 2018, *Nevro Corp. vs. Boston Scientific Corporation and Boston Scientific Neuromodulation Corporation*, Case No. 3:16-cv-06830-VC-MEJ, filed May 14, 2018, 30 pages.
Exhibit J for Declaration of Carson D. Anderson in Support of Nevro's Administrative Motion to File under Seal Portions of Nevro's Reply in Support of It's Motion for Summary Adjudication and Opposition to BSC's Motion for Summary Judgement (Document 382-19), Redacted Version of Document Sought to be Filed under Seal—BSC's Nov. 10, 2017 Supplemental Responses and Objections to Nevro's Interrogatory Requests Nos. 2, 4, 5, and 7, *Nevro Corp. vs. Boston Scientific Corporation and Boston Scientific Neuromodulation Corporation*, Case No. 3:16-cv-06830-VC-MEJ, filed May 14, 2018, 10 pages.
Exhibit K for Declaration of Carson D. Anderson in Support of Nevro's Administrative Motion to File under Seal Portions of Nevro's Reply in Support of It's Motion for Summary Adjudication and Opposition to BSC's Motion for Summary Judgement (Document 382-21), Redacted Version of Document Sought to be Filed under Seal—Dec. 14, 2016 Correspondence between Boston Scientific and U.S. Food and Drug Administration, *Nevro Corp. vs. Boston Scientific Corporation and Boston Scientific Neuromodulation Corporation*, Case No. 3:16-cv-06830-VC-MEJ, filed May 14, 2018, 23 pages.
Exhibit L—Updated for Declaration of Carson D. Anderson in Support of Nevro's Administrative Motion to File under Seal Portions of Nevro's Reply in Support of It's Motion for Summary Adjudication and Opposition to BSC's Motion for Summary Judgement (Document 471), Updated Redacted Version of ECF No. 382-24—Videotaped Deposition of Kaoru Lee Adair, dated May 10, 2017, *Nevro Corp. vs. Boston Scientific Corporation and Boston Scientific Neuromodulation Corporation*, Case No. 3:16-cv-06830-VC-MEJ, filed May 14, 2018, 18 pages.
Exhibit M for Declaration ofCarson D. Anderson in Support of Nevro's Administrative Motion to File under Seal Portions of Nevro's Reply in Support of It's Motion for Summary Adjudication and Opposition to BSC's Motion for Summary Judgement (Document 382-25), Redacted Version of Document Sought to be Filed under Seal—Nevro Corp.'s First Amended Disclosure of Asserted Claims and Infringement Contentions, *Nevro Corp. vs. Boston Scientific Corporation and Boston Scientific Neuromodulation Corporation*, Case No. 3:16-cv-06830-VC-MEJ, filed May 14, 2018, 7 pages.

(56) References Cited

OTHER PUBLICATIONS

Exhibit N for Declaration of Carson D. Anderson in Support of Nevro's Administrative Motion to File under Seal Portions of Nevro's Reply in Support of It's Motion for Summary Adjudication and Opposition to BSC's Motion for Summary Judgement (Document 382-27), Redacted Version of Document Sought to be Filed under Seal—Feb. 2016 Email regarding Precision 10K Training Follow-up, *Nevro Corp.* vs. *Boston Scientific Corporation and Boston Scientific Neuromodulation Corporation*, Case No. 3:16-cv-06830-VC-MEJ, filed May 14, 2018, 5 pages.

Exhibit O for Declaration of Carson D. Anderson in Support of Nevro's Administrative Motion to File under Seal Portions of Nevro's Reply in Support of It's Motion for Summary Adjudication and Opposition to BSC's Motion for Summary Judgement (Document 382-29), Redacted Version of Document Sought to be Filed under Seal—Deposition of Joshua Goshorn dated Mar. 23, 2018, *Nevro Corp.* vs. *Boston Scientific Corporation and Boston Scientific Neuromodulation Corporation*, Case No. 3:16-cv-06830-VC-MEJ, filed May 14, 2018, 16 pages.

Exhibit P for Declaration of Carson D. Anderson in Support of Nevro's Administrative Motion to File under Seal Portions of Nevro's Reply in Support of It's Motion for Summary Adjudication and Opposition to BSC's Motion for Summary Judgement (Document 382-31), Redacted Version of Document Sought to be Filed under Seal—Videotaped Deposition of Daniel Lanovaz dated Mar. 21, 2018, *Nevro Corp.* vs. *Boston Scientific Corporation and Boston Scientific Neuromodulation Corporation*, Case No. 3:16-cv-06830-VC-MEJ, filed May 14, 2018, 12 pages.

[Proposed] Order Granting Administrative Motion to File under Seal Portions of Nevro's Reply in Support of It's Motion for Summary Adjudication and Opposition to BSC's Motion for Summary Judgement and Supporing Documents (Document 382-33), *Nevro Corp.* vs. *Boston Scientific Corporation and Boston Scientific Neuromodulation Corporation*, Case No. 3:16-cv-06830-VC-MEJ, filed May 14, 2018, 7 pages.

Updated Boston Scientific's Reply in Support of Motion for Summary Judgement (Document 473), Updated Redacted Version of ECF No. 397-3, *Nevro Corp.* vs. *Boston Scientific Corporation and Boston Scientific Neuromodulation Corporation*, Case No. 3:16-cv-06830-VC-MEJ, filed Jul. 30, 2018, 27 pages.

Declaration of Carson D. Anderson in Support of Boston Scientific's Reply in Support of Motion for Summary Judgement (Document 398-1), Redacted Version of Document Sought to be Filed under Seal—Cross-Border HCP Arrangement Request, *Nevro Corp.* vs. *Boston Scientific Corporation and Boston Scientific Neuromodulation Corporation*, Case No. 3:16-cv-06830-VC-MEJ, filed May 24, 2018, 3 pages.

Exhibit 1 for Declaration of Carson D. Anderson in Support of Boston Scientific's Reply in Support of Motion for Summary Judgement (Document 398-2), Redacted Version of Document Sought to be Filed under Seal—May 2004 Email regarding Post-Market Studies for AB SCS System, *Nevro Corp.* vs. *Boston Scientific Corporation and Boston Scientific Neuromodulation Corporation*, Case No. 3:16-cv-06830-VC-MEJ, filed May 24, 2018, 5 pages.

Exhibit 2 for Declaration of Carson D. Anderson in Support of Boston Scientific's Reply in Support of Motion for Summary Judgement (Document 398-3), Redacted Version of Document Sought to be Filed under Seal—Corrected Rebuttal Expert Report of Ben Pless regarding Validity, dated Mar. 5, 2018, *Nevro Corp.* vs. *Boston Scientific Corporation and Boston Scientific Neuromodulation Corporation*, Case No. 3:16-cv-06830-VC-MEJ, filed May 24, 2018, 4 pages.

Exhibit 3 for Declaration of Carson D. Anderson in Support of Boston Scientific's Reply in Support of Motion for Summary Judgement (Document 398-4), U.S. Pat. No. 7,389,145 by Kilgore et al., *Nevro Corp.* vs. *Boston Scientific Corporation and Boston Scientific Neuromodulation Corporation*, Case No. 3:16-cv-06830-VC-MEJ, filed May 24, 2018, 12 pages.

Exhibit 4 for Declaration of Carson D. Anderson in Support of Boston Scientific's Reply in Support of Motion for Summary Judgement (Document 398-5), Redacted Version of Document Sought to be Filed under Seal—Videotaped Deposition of Robert Schiff, dated Mar. 15, 2018, *Nevro Corp.* vs. *Boston Scientific Corporation and Boston Scientific Neuromodulation Corporation*, Case No. 3:16-cv-06830-VC-MEJ, filed May 24, 2018, 19 pages.

Exhibit 5 for Declaration of Carson D. Anderson in Support of Boston Scientific's Reply in Support of Motion for Summary Judgement (Document 398-6), Filed under Seal—Document NEVRO_BSXCA0093092-109, *Nevro Corp.* vs. *Boston Scientific Corporation and Boston Scientific Neuromodulation Corporation*, Case No. 3:16-cv-06830-VC-MEJ, filed May 24, 2018, 1 page.

Exhibit 6 for Declaration of Carson D. Anderson in Support of Boston Scientific's Reply in Support of Motion for Summary Judgement (Document 398-7), Filed under Seal—Document NEVRO_BSXCA0067869-75, *Nevro Corp.* vs. *Boston Scientific Corporation and Boston Scientific Neuromodulation Corporation*, Case No. 3:16-cv-06830-VC-MEJ, filed May 24, 2018, 1 page.

Exhibit 7 for Declaration of Carson D. Anderson in Support of Boston Scientific's Reply in Support of Motion for Summary Judgement (Document 398-8), Filed under Seal—Document NEVRO_BSXCA0147580-86, *Nevro Corp.* vs. *Boston Scientific Corporation and Boston Scientific Neuromodulation Corporation*, Case No. 3:16-cv-06830-VC-MEJ, filed May 24, 2018, 1 page.

Exhibit 8 for Declaration of Carson D. Anderson in Support of Boston Scientific's Reply in Support of Motion for Summary Judgement (Document 398-9), Filed under Seal—Opening Expert Report of Ben Pless regarding Infringement, dated Jan. 18, 2018, *Nevro Corp.* vs. *Boston Scientific Corporation and Boston Scientific Neuromodulation Corporation*, Case No. 3:16-cv-06830-VC-MEJ, filed May 24, 2018, 7 pages.

Exhibit 9 for Declaration of Carson D. Anderson in Support of Boston Scientific's Reply in Support of Motion for Summary Judgement (Document 398-10), Filed under Seal—Expert Report of W. Todd Schoettelkotte Relating to Damages, dated Jan. 18, 2018, *Nevro Corp.* vs. *Boston Scientific Corporation and Boston Scientific Neuromodulation Corporation*, Case No. 3:16-cv-06830-VC-MEJ, filed May 24, 2018, 1 page.

Exhibit 10 for Declaration ofCarson D. Anderson in Support of Boston Scientific's Reply in Support of Motion for Summary Judgement (Document 398-11), Redacted Version of Document Sought to be Filed under Seal—Design Change Analysis Form (DCAF), *Nevro Corp.* vs. *Boston Scientific Corporation and Boston Scientific Neuromodulation Corporation*, Case No. 3:16-cv-06830-VC-MEJ, filed May 24, 2018, 2 pages.

Exhibit 11 for Declaration of Carson D. Anderson in Support of Boston Scientific's Reply in Support of Motion for Summary Judgement (Document 398-12), Redacted Version of Document Sought to be Filed under Seal—Videotaped Deposition of Rafael Carbunaru, Ph.D., dated Nov. 14, 2017, *Nevro Corp.* vs. *Boston Scientific Corporation and Boston Scientific Neuromodulation Corporation*, Case No. 3:16-cv-06830-VC-MEJ, filed May 24, 2018, 9 pages.

Exhibit 12 for Declaration ofCarson D. Anderson in Support of Boston Scientific's Reply in Support of Motion for Summary Judgement (Document 398-13), Declaration of James Thacker under 37 CFR 1.1.32, dated Jun. 6, 2013, *Nevro Corp.* vs. *Boston Scientific Corporation and Boston Scientific Neuromodulation Corporation*, Case No. 3:16-cv-06830-VC-MEJ, filed May 24, 2018, 9 pages.

Exhibit 13 for Declaration ofCarson D. Anderson in Support of Boston Scientific's Reply in Support of Motion for Summary Judgement (Document 398-14), Information Disclosure Statement SB-08 Form for U.S. Appl. No. 14/525,134, *Nevro Corp.* vs. *Boston Scientific Corporation and Boston Scientific Neuromodulation Corporation*, Case No. 3:16-cv-06830-VC-MEJ, filed May 24, 2018, 13 pages.

Exhibit 14 for Declaration ofCarson D. Anderson in Support of Boston Scientific's Reply in Support of Motion for Summary Judgement (Document 398-15), Amendment in Response to Final Office Action for U.S. Appl. No. 12/765,685, filed Sep. 19, 2013,

(56) References Cited

OTHER PUBLICATIONS

*Nevro Corp.* vs. *Boston Scientific Corporation and Boston Scientific Neuromodulation Corporation*, Case No. 3:16-cv-06830-VC-MEJ, filed May 24, 2018, 15 pages.
Exhibit 15 for Declaration of Carson D. Anderson in Support of Boston Scientific's Reply in Support of Motion for Summary Judgement (Document 398-16), Amendment in Response to Non-Final Office Action for U.S. Appl. No. 13/830,992, filed Feb. 24, 2014, *Nevro Corp.* vs. *Boston Scientific Corporation and Boston Scientific Neuromodulation Corporation*, Case No. 3:16-cv-06830-VC-MEJ, filed May 24, 2018, 15 pages.
Exhibit 16 for Declaration ofCarson D. Anderson in Support of Boston Scientific's Reply in Support of Motion for Summary Judgement (Document 398-17), Amendment in Response to Final Office Action for U.S. Appl. No. 14/292,671, filed Jan. 17, 2017, *Nevro Corp.* vs. *Boston Scientific Corporation and Boston Scientific Neuromodulation Corporation*, Case No. 3:16-cv-06830-VC-MEJ, filed May 24, 2018, 12 pages.
Declaration of J. Lawrence Stevens in Support of Boston Scientific's Reply in Support of Motion for Summary Judgement (Document 398-18), *Nevro Corp.* vs. *Boston Scientific Corporation and Boston Scientific Neuromodulation Corporation*, Case No. 3:16-cv-06830-VC-MEJ, filed May 24, 2018, 34 pages.
Declaration of Rafael Carbunaru in Support of Boston Scientific Administrative Motion to File under Seal Portions of Boston Scientific's Opposition to Nevro's Motion to Strike BSC's Undisclosed Invalidity Theories (Dkt No. 340) and Supporting Documents (Document 355-2), *Nevro Corp.* vs. *Boston Scientific Corporation and Boston Scientific Neuromodulation Corporation*, Case No. 3:16-cv-06830-VC-MEJ, filed Apr. 26, 2018, 3 pages.
Declaration of Sridhar Kothandaraman (Document 356-1), *Nevro Corp.* vs. *Boston Scientific Corporation and Boston Scientific Neuromodulation Corporation*, Case No. 3:16-cv-06830-VC-MEJ, filed Apr. 26, 2018, 4 pages.
Exhibit B to the Declaration of Clara W. Wang in Support of Nevro's Administrative Motion to File under Seal Portions of Nevro's Reply to Strike BSC's Invalidity Positions and Supporting Documents (Dkt No. 366) (Document 368-4), *Nevro Corp.* vs. *Boston Scientific Corporation and Boston Scientific Neuromodulation Corporation*, Case No. 3:16-cv-06830-VC-MEJ, filed May 7, 2018, 10 pages.
Order Re: Claim Construction and Cross-Motions for Summary Judgement (Document 449), *Nevro Corp.* vs. *Boston Scientific Corporation and Boston Scientific Neuromodulation Corporation*, Case No. 3:16-cv-06830-VC-MEJ, filed Jul. 24, 2018, 9 pages.
Tentative Ruling (Document 422), *Nevro Corp.* vs. *Boston Scientific Corporation and Boston Scientific Neuromodulation Corporation*, Case No. 3:16-cv-06830-VC-MEJ, filed Jul. 5, 2018, 3 pages.
Corrected Rebuttal Expert Report of Ben Pless Regarding Validity on behalf of Plaintiff Nevro Corp., regarding Invalidity of U.S. Pat. Nos. 8,712,533, 9,327,125, 8,359,102, 9,480,842, 9,333,357, 8,792,988, and 8,768,472, *Nevro Corp.* vs. *Boston Scientific Corporation and Boston Scientific Neuromodulation Corporation*, Case No. 3:16-cv-06830-VC-MEJ, Mar. 5, 2018, 785 pages.
Rebuttal Expert Report of Richard T. Mihran, Ph.D., regarding Invalidity of U.S. Pat. Nos. 8,712,533, 9,327,125, 8,359,102, 9,480,842, 9,333,357, 8,792,988, and 8,768,472, *Nevro Corp.* vs. *Boston Scientific Corporation and Boston Scientific Neuromodulation Corporation*, Case No. 3:16-cv-06830-VC-MEJ, Feb. 14, 2018, 195 pages.
Expert Report of Richard T. Mihran, Ph.D., regarding Invalidity of U.S. Pat. Nos. 8,712,533, 9,327,125, 8,359,102, 9,480,842, 9,333,357, 8,792,988, and 8,768,472, *Nevro Corp.* vs. *Boston Scientific Corporation and Boston Scientific Neuromodulation Corporation*, Case No. 3:16-cv-06830-VC-MEJ, Jan. 18, 2018, 958 pages.
Brief for Plaintiff-Appellant Nevro Corp., *Nevro Corp.* vs. *Boston Scientific Corporation and Boston Scientific Neuromodulation Corporation*, Case No. 3:16-cv-06830-VC-MEJ, filed Nov. 8, 2018, 341 pages.

Boston Scientific's Response to the Summons to Attend Oral Proceedings for European Patent No. 2853285, *Nevro Corp.* vs. *Boston Scientific Neuromodulation Corporation and Medtronic, Inc*, filed Nov. 30, 2018, 5 pages.
Medtronic's Response to the Summons to Attend Oral Proceedings for European Patent No. 2853285, *Nevro Corp.* vs. *Boston Scientific Neuromodulation Corporation and Medtronic, Inc.*, filed Nov. 30, 2018, 8 pages.
Decision Rejecting the Opposition (Art. 101(2) EPC) for European Patent No. 2207587, *Nevro Corp.* vs. *Boston Scientific Neuromodulation Corporation and Medtronic, Inc.*, Jan. 4, 2019, 18 pages.
Provision of Minutes in accordance with Rule 124(4) EPC for Opposition by Medtronic, Inc., and Boston Scientific Neuromodulation Corporation for European Patent No. 2207587, mailed Jan. 4, 2019, 10 pages.
Medtronic's Submissions Commenting on the Auxiliary Requests for European Patent No. 2853285, *Nevro Corp.* vs. *Boston Scientific Neuromodulation Corporation and Medtronic, Inc*, filed Jan. 11, 2019, 13 pages.
U.S. Appl. No. 15/606,869, filed May 26, 2017, Lee.
Medtronic—Spinal Cord Stimulation (SCS) Patient Management Guidelines for Clinicians, 1999, 114 pages.
Nevro—Leadership Through Innovation, J. P. Morgan 36th Annual Healthcare Conference, Jan. 24, 2019, 2 pages.
Notice of Opposition for European Patent No. 3156099, Proprietor of the Patent: Nevro Corporation; Opponent: Medtronic, Inc., Mar. 11, 2019, 31 pages.
Opponent Response to Patent Proprietor Comments to Declaration of Dr. Baranidharan for European Patent No. 2630984, mailed Nov. 8, 2016, 3 pages.
Opponents Boston Scientific Neuromodulation Corporation.: Statement Setting Out the Grounds of Appeal for European Patent No. 2207587, mailed May 2, 2019, 12 pages.
Opponents Medtronic, Inc.: Response to Grounds of Appeal for European Patent No. 2630984, mailed Dec. 19, 2017, 23 pages.
Opponents Medtronic, Inc.: Statement Setting Out the Grounds of Appeal for European Patent No. 2207587, mailed May 19, 2019, 21 pages.
Reply of the Patent Proprietor, Nevro Corporation for European Patent No. 2207587, Opponet 1: Medtronic, Inc., and Opponent 2: Boston Scientific Neuromodulation Corporation, mailed Sep. 25, 2019.
Non-Confidential Opening Brief of Appellant Stimwave Technologies, Inc. for Plaintiff-Appellee: *Nevro Corp* vs. Defendant-Appellant: *Stimwave Technologies, Inc.*, United States Court of Appeals for Federal Circuit, Case 19-CV-325, filed Sep. 24, 2019, 156 pages.
Principal and Response Brief for Defendants-Cross-Appellants Boston Scientific Corporation's and Boston Scientific Neuromodulation Corporation's, *Nevro Corp.* v. *Boston Scientific Corporation and Boston Scientific Neuromodulation Corporation*, Case No. 3:16-cv-06830-VC (N.D. Cal.), Jan. 17, 2019, 71 pages.
Reply Brief for Defendants-Cross-Appellants Boston Scientific Corporation's and Boston Scientific Neuromodulation Corporation's, *Nevro Corp.* v. *Boston Scientific Corporation and Boston Scientific Neuromodulation Corporation*, Case No. 3:16-cv-06830-VC (N.D. Cal.), Jun. 3, 2019, 26 pages.
Response and Reply Brief for Plaintiff-Appellant Nevro Corp., *Nevro Corp.* v. *Boston Scientific Corporation and Boston Scientific Neuromodulation Corporation*, Case No. 3:16-cv-06830-VC (N.D. Cal.), Apr. 12, 2019, 68 pages.
Memorandum Opinion, Plaintiff: *Nevro Corp.* vs. Defendant-Appellant: *Stimwave Technologies, Inc.*, United States Court for the District of Delaware, Civil Action No. 19-325-CFC, Case 19-CV-325, filed Jul. 24, 2019, 46 pages.
Summons to Attend Oral Proceedings pursuant to Rule 115(1) EPC for European Patent No. 3156099, Applicant: Nevro Corporation, mailed Nov. 22, 2019, 21 pages.
Communication Submitted with Corrected Exhibits for U.S. Pat. No. 8,359,102, Case No. IPR2015-01204, Petitioner: Boston Scientific Neuromodulation Corporation, Patent Owner: Nevro Corporation, dated Jun. 4, 2015, 4 pages.

(56) References Cited

OTHER PUBLICATIONS

Decision Denying Institution of Inter Partes Review for U.S. Pat. No. 8,359,102, Case No. IPR2015-01204, Petitioner: Boston Scientific Neuromodulation Corporation, Patent Owner: Nevro Corporation, mailed Nov. 30, 2015, 14 pages.
European Extended Search Report for European Patent Application No. 17154846.4, Applicant: Nevro Corporation, dated Jul. 11, 2017, 6 pages.
European Search Report for European Application No. 10160641.6, Applicant: Nevro Corporation, mailed Apr. 12, 2011, 7 pages.
Exhibit 1101: U.S. Pat. No. 8,359,102, for U.S. Pat. No. 8,359,102, Case No. IPR2015-01204, Petitioner: Boston Scientific Neuromodulation Corporation, Patent Owner: Nevro Corporation, filed Jun. 4, 2015, 32 pages.
Exhibit 1102: U.S. Patent Publication No. 2007/0073354, for U.S. Pat. No. 8,359,102, Case No. IPR2015-01204, Petitioner: Boston Scientific Neuromodulation Corporation, Patent Owner: Nevro Corporation, filed Jun. 4, 2015, 14 pages.
Exhibit 1103: U.S. Patent Publication No. 2011/0184488, for U.S. Pat. No. 8,359,102, Case No. IPR2015-01204, Petitioner: Boston Scientific Neuromodulation Corporation, Patent Owner: Nevro Corporation, filed Jun. 4, 2015, 18 pages.
Exhibit 1104: U.S. Pat. No. 5,776,170, for U.S. Pat. No. 8,359,102, Case No. IPR2015-01204, Petitioner: Boston Scientific Neuromodulation Corporation, Patent Owner: Nevro Corporation, filed Jun. 4, 2015, 11 pages.
Exhibit 1105: U.S. Appl. No. 13/245,450 file history, Office Action, Nov. 18, 2011, for U.S. Pat. No. 8,359,102, Case No. IPR2015-01204, Petitioner: Boston Scientific Neuromodulation Corporation, Patent Owner: Nevro Corporation, filed Jun. 4, 2015, 11 pages.
Exhibit 1106: U.S. Appl. No. 13/245,450 file history, Interview Summary, Feb. 1, 2012, for U.S. Pat. No. 8,359,102, Case No. IPR2015-01204, Petitioner: Boston Scientific Neuromodulation Corporation, Patent Owner: Nevro Corporation, filed Jun. 4, 2015, 2 pages.
Exhibit 1107: U.S. Appl. No. 13/245,450 file history, Amendment, Feb. 7, 2012, for U.S. Pat. No. 8,359,102, Case No. IPR2015-01204, Petitioner: Boston Scientific Neuromodulation Corporation, Patent Owner: Nevro Corporation, filed Jun. 4, 2015, 15 pages.
Exhibit 1108: U.S. Appl. No. 13/245,450 file history, Notice of Allowability, Mar. 14, 2012, for U.S. Pat. No. 8,359,102, Case No. IPR2015-01204, Petitioner: Boston Scientific Neuromodulation Corporation, Patent Owner: Nevro Corporation, filed Jun. 4, 2015, 8 pages.
Exhibit 1109: U.S. Appl. No. 13/446,970 file history, Preliminary Amendment, May 18, 2012, for U.S. Pat. No. 8,359,102, Case No. IPR2015-01204, Petitioner: Boston Scientific Neuromodulation Corporation, Patent Owner: Nevro Corporation, filed Jun. 4, 2015, 7 pages.
Exhibit 1110: U.S. Appl. No. 13/245,970 file history, Ex Parte Quayle Action, Oct. 15, 2012, for U.S. Pat. No. 8,359,102, Case No. IPR2015-01204, Petitioner: Boston Scientific Neuromodulation Corporation, Patent Owner: Nevro Corporation, filed Jun. 4, 2015, 9 pages.
Exhibit 1111: U.S. Appl. No. 13/245,970 file history, Amendment in Response to Ex Parte Quayle Office Action, Nov. 28, 2012, for U.S. Pat. No. 8,359,102, Case No. IPR2015-01204, Petitioner: Boston Scientific Neuromodulation Corporation, Patent Owner: Nevro Corporation, filed Jun. 4, 2015, 14 pages.
Exhibit 1112: U.S. Appl. No. 12/765,747 file history, Office Action, Jul. 25, 2013, for U.S. Pat. No. 8,359,102, Case No. IPR2015-01204, Petitioner: Boston Scientific Neuromodulation Corporation, Patent Owner: Nevro Corporation, filed Jun. 4, 2015, 7 pages.
Exhibit 1113: U.S. Appl. No. 12/765,747 file history, Amendment, Jan. 24, 2014, for U.S. Pat. No. 8,359,102, Case No. IPR2015-01204, Petitioner: Boston Scientific Neuromodulation Corporation, Patent Owner: Nevro Corporation, filed Jun. 4, 2015, 21 pages.
Exhibit 1114: Merriam Webster's Collegiate Dictionary, 10th ed., p. 583, for U.S. Pat. No. 8,359,102, Case No. IPR2015-01204, Petitioner: Boston Scientific Neuromodulation Corporation, Patent Owner: Nevro Corporation, filed Jun. 4, 2015, 3 pages.
Exhibit 1115: Declaration of Prof. Cameron C. McIntyre Ph.D., for U.S. Pat. No. 8,359,102, Case No. IPR2015-01204, Petitioner: Boston Scientific Neuromodulation Corporation, Patent Owner: Nevro Corporation, filed Jun. 4, 2015, 58 pages.
Exhibit 1116: Kilgore KL et al. "Reversible Nerve Conduction Block Using Kilohetrz Frequency Alternating Current," Neuromodulation (2013) 17 242-255. for U.S. Pat. No. 8,359,102, Case No. IPR2015-01204, Petitioner: Boston Scientific Neuromodulation Corporation, Patent Owner: Nevro Corporation, filed Jun. 4, 2015, 14 pages.
Exhibit 1117: Perruchoud et al., "Analgesic Efficacy of High-Frequency Spinal Cord Stimulation: A Randomized Double-Blind Placebo-Controlled Study," Neuromodulation (2013) 16 363-369 for U.S. Pat. No. 8,359,102, Case No. IPR2015-01204, Petitioner: Boston Scientific Neuromodulation Corporation, Patent Owner: Nevro Corporation, filed Jun. 4, 2015, 7 pages.
Exhibit 1118: U.S. Patent Publication 2006/0259098, for U.S. Pat. No. 8,359,102, Case No. IPR2015-01204, Petitioner: Boston Scientific Neuromodulation Corporation, Patent Owner: Nevro Corporation, filed Jun. 4, 2015, 28 pages.
Exhibit 1119: U.S. Pat. No. 8,280,515, for U.S. Pat. No. 8,359,102, Case No. IPR2015-01204, Petitioner: Boston Scientific Neuromodulation Corporation, Patent Owner: Nevro Corporation, filed Jun. 4, 2015, 15 pages.
Exhibit 1120: U.S. Pat. No. 2006/0015153, for U.S. Pat. No. 8,359,102, Case No. IPR2015-01204, Petitioner: Boston Scientific Neuromodulation Corporation, Patent Owner: Nevro Corporation, filed Jun. 4, 2015, 53 pages.
Exhibit 1121: Bhadra N et al. "Simulation of high-frequency sinusoidal electrical block of mammalian myelinated axons," J. Comput. Neurosci. (2007) 22 313-326. for U.S. Pat. No. 8,359,102, Case No. IPR2015-01204, Petitioner: Boston Scientific Neuromodulation Corporation, Patent Owner: Nevro Corporation, filed Jun. 4, 2015, 14 pages.
Exhibit 1122: U.S. Pat. No. 8,712,533, for U.S. Pat. No. 8,359,102, Case No. IPR2015-01204, Petitioner: Boston Scientific Neuromodulation Corporation, Patent Owner: Nevro Corporation, filed Jun. 4, 2015, 34 pages.
Exhibit 2001: Kapural et al., "Novel 10-kHz High-frequency Therapy (HF10 Therapy) Is Superior to Traditional Low-frequency Spinal Cord Stimulation for the Treatment of Chronic Back and Leg Pain: The SENZA-RCT Randomized Controlled Trial," Anesthesiology, vol. 123, No. 4 (Oct. 2015), for U.S. Pat. No. 8,359,102, Case No. IPR2015-01204, Petitioner: Boston Scientific Neuromodulation Corporation, Patent Owner: Nevro Corporation, filed Sep. 1, 2015, 11 pages.
Exhibit 2002: Food and Drug Administration Letter Regarding Approval of Premarket Approval Application for Nevro Senza SCS System, May 8, 2015, for U.S. Pat. No. 8,359,102, Case No. IPR2015-01204, Petitioner: Boston Scientific Neuromodulation Corporation, Patent Owner: Nevro Corporation, filed Sep. 1, 2015, 4 pages.
Exhibit 2003: Perruchoud et al., "Analgesic Efficacy of High-Frequency Spinal Cord Stimulation: A Randomized Double-Blind Placebo-Controlled Study," Neuromodulation: Technology at the Neural Interface, vol. 16, No. 4 (Jul./Aug. 2013), for U.S. Pat. No. 8,359,102, Case No. IPR2015-01204, Petitioner: Boston Scientific Neuromodulation Corporation, Patent Owner: Nevro Corporation, filed Sep. 1, 2015, 7 pages.
Exhibit 2004: Kumar et al., "The Effects of Spinal Cord Stimulation In Neuropathic Pain Are Sustained: A 24-Month Follow-up Of The Prospective Randomized Controlled Multicenter Trial Of The Effectiveness of Spinal Cord Stimulation," Neurosurgery, vol. 63, No. 4 (Oct. 2008), for U.S. Pat. No. 8,359,102, Case No. IPR2015-01204, Petitioner: Boston Scientific Neuromodulation Corporation, Patent Owner: Nevro Corporation, filed Sep. 1, 2015, 9 pages.
Exhibit 2005: Oakley et al., "A New Spinal Cord Stimulation System Effectively Relieves Chronic, Intractable Pain: A Multicenter Prospective Clinical Study," Neuromodulation: Technology at the Neural Interface, vol. 10, No. 3 (Jul. 2007), for U.S. Pat. No.

(56) References Cited

OTHER PUBLICATIONS 8,359,102, Case No. IPR2015-01204, Petitioner: Boston Scientific Neuromodulation Corporation, Patent Owner: Nevro Corporation, filed Sep. 1, 2015, 17 pages.
Exhibit 2006: Oakley et al., "Spinal Cord Stimulation, Mechanisms of Action" vol. 27, No. 22 (2002), for U.S. Pat. No. 8,359,102, Case No. IPR2015-01204, Petitioner: Boston Scientific Neuromodulation Corporation, Patent Owner: Nevro Corporation, filed Sep. 1, 2015, 10 pages.
Exhibit 2007: Oakley, J., "Spinal Cord Stimulation in Axial Low Back Pain: Solving the Dilemma," Pain Medicine, vol. 7, No. S1 (2006), for U.S. Pat. No. 8,359,102, Case No. IPR2015-01204, Petitioner: Boston Scientific Neuromodulation Corporation, Patent Owner: Nevro Corporation, filed Sep. 1, 2015, 6 pages.
Exhibit 2008: Krames et al., Neuromodulation, London: Elsevier, 2009, for U.S. Pat. No. 8,359,102, Case No. IPR2015-01204, Petitioner: Boston Scientific Neuromodulation Corporation, Patent Owner: Nevro Corporation, filed Sep. 1, 2015, 19 pages.
Exhibit 2009: "Nevro Patient Manual," Nevro Corp., Ser. No. 11051 Rev A, Jan. 16, 2015, for U.S. Pat. No. 8,359,102, Case No. IPR2015-01204, Petitioner: Boston Scientific Neuromodulation Corporation, Patent Owner: Nevro Corporation, filed Sep. 1, 2015, 53 pages.
Exhibit 2010: "Nevro Physician Implant Manual," Nevro Corp., Ser. No. 11052 Rev B, Jan. 16, 2015, for U.S. Pat. No. 8,359,102, Case No. IPR2015-01204, Petitioner: Boston Scientific Neuromodulation Corporation, Patent Owner: Nevro Corporation, filed Sep. 1, 2015, 31 pages.
Exhibit 2011: Definition of "paresthesia," Dorland's Illustrated Medical Dictionary, Twenty-Sixth Edition, Philadelphia: W.B. Saunders Company, 1981, for U.S. Pat. No. 8,359,102, Case No. IPR2015-01204, Petitioner: Boston Scientific Neuromodulation Corporation, Patent Owner: Nevro Corporation, filed Sep. 1, 2015, 4 pages.
Exhibit 2012: Definition of "paresthesia," Mosby's Medical Dictionary, 8th Edition, St. Louis, MO: Mosby Elsevier, 2009, for U.S. Pat. No. 8,359,102, Case No. IPR2015-01204, Petitioner: Boston Scientific Neuromodulation Corporation, Patent Owner: Nevro Corporation, filed Sep. 1, 2015, 3 pages.
Exhibit 2013: Definition of "paresthesia," Webster's Third New International Dictionary of the English Language, Unabridged, Springfield, MA: Merriam-Webster, Inc., 1993, for U.S. Pat. No. 8,359,102, Case No. IPR2015-01204, Petitioner: Boston Scientific Neuromodulation Corporation, Patent Owner: Nevro Corporation, filed Sep. 1, 2015, 3 pages.
Exhibit 2014: Prausnitz, "The effects of electric current applied to the skin: A review for transdermal drug delivery," Advanced Drug Delivery Reviews, vol. 18, 1996, for U.S. Pat. No. 8,359,102, Case No. IPR2015-01204, Petitioner: Boston Scientific Neuromodulation Corporation, Patent Owner: Nevro Corporation, filed Sep. 1, 2015, 31 pages.
Exhibit 2015: ClinicalTrials.gov, "Safety and Effectiveness Study of the Precision SCS System Adapted for High-Rate Spinal Cord Stimulation (Accelerate)," U.S. National Institutes of Health, for U.S. Pat. No. 8,359,102, Case No. IPR2015-01204, Petitioner: Boston Scientific Neuromodulation Corporation, Patent Owner: Nevro Corporation, filed Sep. 1, 2015, 3 pages.
Exhibit 2016: Stimwave.com, "Stimwave Receives FDA Approval for High Frequency IDE," Stimwave LLC press release, Jun. 9, 2015, for U.S. Pat. No. 8,359,102, Case No. IPR2015-01204, Petitioner: Boston Scientific Neuromodulation Corporation, Patent Owner: Nevro Corporation, filed Sep. 1, 2015, 2 pages.
Exhibit 2017: Van Buyten et al., "High-Frequency Spinal Cord Stimulation for the Treatment of Chronic Back Pain Patients: Results of a Prospective Multicenter European Clinical Study," Neuromodulation: Technology at the Neural Interface, vol. 16, No. 1 (Jan./Feb. 2013), for U.S. Pat. No. 8,359,102, Case No. IPR2015-01204, Petitioner: Boston Scientific Neuromodulation Corporation, Patent Owner: Nevro Corporation, filed Sep. 1, 2015, 8 pages.
Exhibit 2018: Al-Kaisey et al., "Sustained Effectiveness of 10 kHz High-Frequency Spinal Cord Stimulation for Patients with Chronic, Low Back Pain: 24-Month Results of a Prospective Multicenter Study," Pain Medicine, vol. 15, No. 3 (2014), for U.S. Pat. No. 8,359,102, Case No. IPR2015-01204, Petitioner: Boston Scientific Neuromodulation Corporation, Patent Owner: Nevro Corporation, filed Sep. 1, 2015, 8 pages.
Exhibit 2019: Lemka et al., "Computational Analysis of Kilohertz Frequency Spinal Cord Stimulation for Chronic Pain Management," Pain Medicine, vol. 122, No. 6 (2015), for U.S. Pat. No. 8,359,102, Case No. IPR2015-01204, Petitioner: Boston Scientific Neuromodulation Corporation, Patent Owner: Nevro Corporation, filed Sep. 1, 2015, 15 pages.
Exhibit 2020: Kilgore et al., "Reversible Nerve Conduction Block Using Kilohertz Frequency Alternating Current," Neuromodulation: Technology at the Neural Interface, vol. 17, No. 3 (Apr. 2014), for U.S. Pat. No. 8,359,102, Case No. IPR2015-01204, Petitioner: Boston Scientific Neuromodulation Corporation, Patent Owner: Nevro Corporation, filed Sep. 1, 2015, 14 pages.
Exhibit 2021: "PrecisionTM Spinal Cord Stimulator System Clinician Manual, Directions for Use," Boston Scientific Neuromodulation, U.S. Appl. No. 90/834,026-10 Rev. B (2015), for U.S. Pat. No. 8,359,102, Case No. IPR2015-01204, Petitioner: Boston Scientific Neuromodulation Corporation, Patent Owner: Nevro Corporation, filed Sep. 1, 2015, 74 pages.
Exhibit 2022: St. Jude Medical, "Eon MiniTM Rechargeable IPG," Product Overview, last updated Apr. 29, 2013, for U.S. Pat. No. 8,359,102, Case No. IPR2015-01204, Petitioner: Boston Scientific Neuromodulation Corporation, Patent Owner: Nevro Corporation, filed Sep. 1, 2015, 5 pages.
Exhibit 2023: "Medtronic Pain Therapy, Using neurostimulation for chronic pain, Information for prescribers," Medtronic, Inc., Sep. 2009, for U.S. Pat. No. 8,359,102, Case No. IPR2015-01204, Petitioner: Boston Scientific Neuromodulation Corporation, Patent Owner: Nevro Corporation, filed Sep. 1, 2015, 29 pages.
Exhibit 2024: "Summary of Safety and Effectiveness Data (SSED)," Food and Drug Administration, Ser. No. Pma P130022, (May 8, 2015), for U.S. Pat. No. 8,359,102, Case No. IPR2015-01204, Petitioner: Boston Scientific Neuromodulation Corporation, Patent Owner: Nevro Corporation, filed Sep. 1, 2015, 56 pages.
Exhibit 2025: Wallace et al., "Accelerate: A Prospective Multicenter Trial Evaluating the Use of High Rate Spinal Cord Stimulation in the Management of Chronic Intractable Pain," poster presented at North American Neuromodulation Society Annual Meeting, 2014, for U.S. Pat. No. 8,359,102, Case No. IPR2015-01204, Petitioner: Boston Scientific Neuromodulation Corporation, Patent Owner: Nevro Corporation, filed Sep. 1, 2015, 1 page.
Exhibit 2026: Levy, R.M., "The Need for Mechanism-Based Medicine in Neuromodulation," Neuromodulation: Technology at the Neural Interface, vol. 15, No. 4 (Jul./Aug. 2012), for U.S. Pat. No. 8,359,102, Case No. IPR2015-01204, Petitioner: Boston Scientific Neuromodulation Corporation, Patent Owner: Nevro Corporation, filed Sep. 1, 2015, 7 pages.
Exhibit 2027: Applicant-Initiated Interview Summary, directed to U.S. Appl. No. 12/765,747, mailed Sep. 11, 2013, for U.S. Pat. No. 8,359,102, Case No. IPR2015-01204, Petitioner: Boston Scientific Neuromodulation Corporation, Patent Owner: Nevro Corporation, filed Sep. 1, 2015, 4 pages.
Exhibit 2028: Applicant-Initiated Interview Summary, directed to U.S. Appl. No. 13/725,770, mailed Apr. 5, 2013, for U.S. Pat. No. 8,359,102, Case No. IPR2015-01204, Petitioner: Boston Scientific Neuromodulation Corporation, Patent Owner: Nevro Corporation, filed Sep. 1, 2015, 3 pages.
Exhibit 2030: Non-Final Office Action directed to U.S. Appl. No. 12/765,747, mailed Jul. 25, 2013, for U.S. Pat. No. 8,359,102, Case No. IPR2015- 01204, Petitioner: Boston Scientific Neuromodulation Corporation, Patent Owner: Nevro Corporation, filed Sep. 1, 2015, 7 pages.
Exhibit 2031: "Neuromodulation: Vision 2010," North American Neuromodulation Society, 14th Annual Meeting Program Book, Dec. 2-5, 2010, for U.S. Pat. No. 8,359,102, Case No. IPR2015-01204, Petitioner: Boston Scientific Neuromodulation Corporation, Patent Owner: Nevro Corporation, filed Sep. 1, 2015, 9 pages.
Exhibit 2032: "15th Annual Meeting, Our Crystal Anniversary," North American Neuromodulation Society, 15th Annual Meeting,

(56) References Cited

OTHER PUBLICATIONS

Dec. 8-11, 2011, for U.S. Pat. No. 8,359,102, Case No. IPR2015-01204, Petitioner: Boston Scientific Neuromodulation Corporation, Patent Owner: Nevro Corporation, filed Sep. 1, 2015, 8 pages.
Exhibit 2033: "From Innovation to Reality," North American Neuromodulation Society, 16th Annual Meeting Syllabus, Dec. 6-9, 2012, for U.S. Pat. No. 8,359,102, Case No. IPR2015-01204, Petitioner: Boston Scientific Neuromodulation Corporation, Patent Owner: Nevro Corporation, filed Sep. 1, 2015, 198 pages.
Exhibit 2034: "Today's Vision, Tomorrow's Reality," North American Neuromodulation Society, 17th Annual Meeting, Dec. 5-8, 2013, for U.S. Pat. No. 8,359,102, Case No. IPR2015-01204, Petitioner: Boston Scientific Neuromodulation Corporation, Patent Owner: Nevro Corporation, filed Sep. 1, 2015, 12 pages.
Exhibit 2035: "Celebrating 20 Years," North American Neuromodulation Society, 18th Annual Meeting Program Book, Dec. 11-14, 2014, for U.S. Pat. No. 8,359,102, Case No. IPR2015-01204, Petitioner: Boston Scientific Neuromodulation Corporation, Patent Owner: Nevro Corporation, filed Sep. 1, 2015, 28 pages.
Exhibit 2036: "Nevro Corp. Announces Pricing of Initial Public Offering," Nevro Corp. press release, Nov. 6, 2014, for U.S. Pat. No. 8,359,102, Case No. IPR2015-01204, Petitioner: Boston Scientific Neuromodulation Corporation, Patent Owner: Nevro Corporation, filed Sep. 1, 2015, 1 page.
Exhibit 2037: Applicant-Initiated Interview Summary directed to U.S. Appl. No. 14/037,230, mailed Jan. 29, 2014, for U.S. Pat. No. 8,359,102, Case No. IPR2015-01204, Petitioner: Boston Scientific Neuromodulation Corporation, Patent Owner: Nevro Corporation, filed Sep. 1, 2015, 3 pages.
Exhibit 2038: Applicant-Initiated Interview Summary directed to U.S. Appl. No. 13/831,057, mailed Jan. 29, 2014, for U.S. Pat. No. 8,359,102, Case No. IPR2015-01204, Petitioner: Boston Scientific Neuromodulation Corporation, Patent Owner: Nevro Corporation, filed Sep. 1, 2015, 3 pages.
Exhibit 2039: Applicant-Initiated Interview Summary directed to U.S. Appl. No. 13/620,235, mailed Aug. 18, 2014, for U.S. Pat. No. 8,359,102, Case No. IPR2015-01204, Petitioner: Boston Scientific Neuromodulation Corporation, Patent Owner: Nevro Corporation, filed Sep. 1, 2015, 3 pages.
Exhibit 2040: Applicant-Initiated Interview Summary directed to U.S. Appl. No. 12/765,747, mailed Jan. 29, 2014, for U.S. Pat. No. 8,359,102, Case No. IPR2015-01204, Petitioner: Boston Scientific Neuromodulation Corporation, Patent Owner: Nevro Corporation, filed Sep. 1, 2015, 3 pages.
Exhibit 2041: Notice of Allowance directed to U.S. Appl. No. 12/765,747, mailed Feb. 12, 2014, for U.S. Pat. No. 8,359,102, Case No. IPR2015-01204, Petitioner: Boston Scientific Neuromodulation Corporation, Patent Owner: Nevro Corporation, filed Sep. 1, 2015, 7 pages.
International Search Report and Written Opinion, International Application; No. PCT/US 10/32124. Applicant: Nevro Corporation, European Patent Office, mailed Jun. 16, 2010, 24 pages.
Muller and Hunsperger, "Helvetica Physiologica Acta Reversible Blockierung der Erregungsleitung im Nerven durch Mittelfrequenz-Daverstrom." Schwabe & Co. Basel, vol. 25, Fasc. 1, 1967, 6 pages (with Machine English Translation).
Notice of Accepting Corrected Petition for U.S. Pat. No. 8,359,102, Case No. IPR2015-01204, Petitioner: Boston Scientific Neuromodulation Corporation, Patent Owner: Nevro Corporation, dated Jul. 7, 2015, 2 pages.
Notice of Filing Date Accorded to Petition and Time for Filing Patent Owner Preliminary Response for U.S. Pat. No. 8,359,102, Case No. IPR2015-01204, Petitioner: Boston Scientific Neuromodulation Corporation, Patent Owner: Nevro Corporation, dated Jun. 1, 2015, 3 pages.
Ohnmeiss et al., "Prospective outcome evaluation of spinal cord stimulation in patients with intractable leg pain," Spine, Jun. 1, 1996, 21(11):1344-1350.
Partial European Search Report, European Application No. EP10160641, Applicant: Nevro Corporation, mailed Aug. 30, 2010, 3 pages.
Patent Owner's Mandatory Notices for U.S. Pat. No. 8,359,102, Case No. IPR2015-01204, Petitioner: Boston Scientific Neuromodulation Corporation, Patent Owner: Nevro Corporation, dated Jun. 3, 2015, 5 pages.
Patent Owner's Preliminary Response for U.S. Pat. No. 8,359,102, Case No. IPR2015-01204, Petitioner: Boston Scientific Neuromodulation Corporation, Patent Owner: Nevro Corporation, dated Sep. 1, 2015, 63 pages.
Patent Owner's Supplemental Mandatory Notice Information for U.S. Pat. No. 8,359,102, Case No. IPR2015-01204, Petitioner: Boston Scientific Neuromodulation Corporation, Patent Owner: Nevro Corporation, dated Aug. 28, 2015, 5 pages.
Petition for Inter Partes Review for U.S. Pat. No. 8,359,102, Case No. IPR2015-01204, Petitioner: Boston Scientific Neuromodulation Corporation, Patent Owner: Nevro Corporation, dated May 14, 2015, 41 pages.
Tanner, J.A., "Reversible blocking of nerve conduction by alternating-current; excitation." Nature, Aug. 18, 1962; 195: 712-3.
de Vos et al., "Spinal cord stimulation with hybrid lead relieves pain in low back and legs," Neuromodulation, March/Apr. 2012, 15(2):118-123.
Demand for Arbitration, Nevro Corp. v. Mayo Foundation for Medical Education and Research & Venturi Group, LLC (now Flathead Partners, LLC), American Arbitration Association, Case# 01-22-0002-8455, filed on Jul. 1, 2022, 33 pages.
Fda, "Summary of Safety and Effectiveness Data (Ssed): Senza Spinal Cord Stimulation (SCS) System," Pma P130022, 2015, 56 pages.
Kumar et al., "Spinal cord stimulation versus conventional medical management for neuropathic pain: a multicentre randomized controlled trial in patients with failed back surgery syndrome," Pain, Nov. 2007, 132(1-2):179-188.
Lee et al., "Low-intensity, Kilohertz Frequency Spinal Cord Stimulation Differently Affects Excitatory and Inhibitory Neurons in the Rodent Superficial Dorsal Horn," Neuroscience, Jan. 7, 2020, 428:132-139.
Nevro Corp., "Patient Manual,"11052 Rev L, 2021, 94 pages.
Nevro Corp., "Physician Implant Manual: Senza® Senza I[TM Senza Omnia™M," 11051 Rev L, 2020, 69 pages.
Nevro Corp.'s Answer to Respondents' Counterclaims, Nevro Corp. v. Mayo Foundation for Medical Education and Research & Venturi Group, LLC (now Flathead Partners, LLC), American Arbitration Association, Case# 01-22-0002-8455, filed on Aug. 19, 2022, 33 pages.
Respondents' Answering Statement and Counterclaims, Nevro Corp. v. Mayo Foundation for Medical Education and Research & Venturi Group, LLC (now Flathead Partners, LLC), American Arbitration Association, Case# 01-22-0002-8455, filed on Aug. 5, 2022, 33 pages.
Argoff, "10 kHz Spinal Cord Stimulation Durably Improves Foot Sensation in Patients with Peripheral Diabetic Neuropathy," Presented at Proceedings of the 2023 North American Neuromodulation Society Conference, Las Vegas, Nevada, USA, Jan. 12-15, 2023, 7 pages.
Bhadra et al., "Reversible conduction block in peripheral nerve using electrical waveforms," Bioelectron. Medicine, Dec. 14, 2017, 1(1):39-54.
Chen et al., "A Real-World Analysis of High-Frequency 10 kHz Spinal Cord Stimulation for the Treatment of Painful Diabetic Peripheral Neuropathy," J. Diabetes Sci. Technology, Nov. 29, 2021, 16(2):282-288.
Lee et al., "Differential Modulation of Dorsal Horn Neurons by Various Spinal Cord Stimulation Strategies," Biomedicine, May 18, 2021, 9:568, 12 pages.
Lee et al., "Simultaneous 10 kHz and 40 Hz spinal cord stimulation increases dorsal horn inhibitory interneuron activity," Neurosci. Letters, Jun. 2, 2022, 782:136705, 6 pages.
Neudorfer et al., "Kilohertz-frequency stimulation of the nervous system: A review of underlying mechanisms," Brain Stimulation, Mar. 20, 2021, 14(3)513-530.
Petersen et al., "Durability of High-Frequency 10-kHz Spinal Cord Stimulation for Patients With Painful Diabetic Neuropathy Refrac-

(56) References Cited

OTHER PUBLICATIONS tory to Conventional Treatments: 12-Month Results From a Randomized Controlled Trial," Diabetes Care, Jan. 2022, 45(1):e3-e6.
Petersen et al., "Effect of High-frequency (10-kHz) Spinal Cord Stimulation in Patients With Painful Diabetic Neuropathy: A Randomized Clinical Trial," JAMA Neurology, Apr. 5, 2021, 78(6):687-698.
Strand et al., "Neuromodulation in the Treatment of Painful Diabetic Neuropathy: A Review of Evidence for Spinal Cord Stimulation," J. Diabetes Sci. Technology, Nov. 29, 2021, 16(2):332-340.
Wang et al., "Low-Intensity 10 kHz Spinal Cord Stimulation Reduces Behavioral and Neural Hypersensitivity in a Rat Model of Painful Diabetic Neuropathy," J. Pain Research, May 24, 2022, 15:1503-1513.
Zhao et al., "Conduction block in myelinated axons induced by high-frequency (kHz) non-symmetric biphasic stimulation," Front. Comp. Neuroscience, Jul. 8, 2015, 9:85, 10 pages.
Lempka et al., "Innovations in spinal cord stimulation for pain," Curr. Opin. Biomed. Eng., Dec. 2018, 8:51-60, 17 pages.
Letter from Ching-Lee Fukuda to Betsy Flanagan et al., Re: Duty of Candor and Disclosure to the U.S. Patent and Trademark Office, dated Apr. 25, 2023, 2 pages.
Letter from Ching-Lee Fukuda to Michael Kane et al., Re: *Nevro* v. *Mayo et al.* (AAA Case No. 01-22-0002-8455), dated Jul. 5, 2023, 4 pages.
Metzger et al., "A novel fast-acting sub-perception spinal cordstimulation therapy enables rapid onset of analgesia in patients with chronic pain," Expert Review of Medical Devices, Mar. 2021, 18(3):299-306, 9 pages.
Morton et al., "Effect of Vagal Nerve Blockade on Moderate Obesity with an Obesity-Related Comorbid Condition: the ReCharge Study," Obes. Surg., Apr. 2016, 26(5): 983-989, 7 pages.
Respondents' Responses to Nevro's Discovery Requests and Redfern Schedule, Interrogatory No. 6, American Arbitration Association Case No. 01-22-0002-8455, dated Mar. 29, 2023, 9 pages.
Tai et al., "Response of External Urethral Sphincter to High Frequency Biphasic Electrical Stimulation of Pudendal Nerve," Journal of Urology, Aug. 2005, 174(2):782-786, 5 pages.
Expert Report of Joan Ellis, American Arbitration Association Case No. 01-22-0002-8455, dated May 20, 2023, 20 pages (excerpt).
Expert Report of Ben Pless, American Arbitration Association Case No. 01-22-0002-8455, dated May 19, 2023, 15 pages (excerpt).
Letter from Ching-Lee Fukuda to Patrick Finn et al., Re: Mayo and Flathead's positions in the Nevro v. Mayo et al. (AAA Case No. 01-22-0002-8455) Arbitration on the scope of the pending claims of the '389 Application must be disclosed to the Patent Office, dated Nov. 16, 2023, 121 pages (with Attached Exhibits).
Responsive Expert Report of Dr. Lawrence R. Poree, M.D., Ph.D., M.P.H., American Arbitration Association Case No. 01-22-0002-8455, dated Jun. 14, 2023, 11 pages (excerpt).
Respondents' Prehearing Brief, American Arbitration Association Case No. 01-22-0002-8455, dated Aug. 30, 2023, 6 pages (excerpt).
Nevro's Pre-Hearing Brief, American Arbitration Association Case No. 01-22-0002-8455, dated Aug. 30, 2023, 6 pages (excerpt).
Respondents' Post-Hearing Brief, American Arbitration Association Case No. 01-22-0002-8455, dated Oct. 23, 2023, 8 pages (excerpt).
Nevro's Post-Hearing Brief, American Arbitration Association Case No. 01-22-0002-8455, dated Oct. 23, 2023, 6 pages (excerpt).
Nevro's Response to Respondents' Brief on Fees and Costs, American Arbitration Association AAA Case No. 01-22-0002-8455, dated Jan. 31, 2024, 6 pages (excerpt).
Nevro's Submission for an Award of Its Fees and Costs, American Arbitration Association AAA Case No. 01-22-0002-8455, dated Jan. 24, 2024, 14 pages (excerpt).
Respondents' Brief in Opposition to Claimant's Claim for Fees and Costs, American Arbitration Association AAA Case No. 02-22-0002-8455, dated Jan. 31, 2024, 7 pages (excerpt).
Respondents' Brief in Support of Claim for Fees and Costs, American Arbitration Association AAA Case No. 02-22-0002-8455, dated Jan. 24, 2024, 11 pages (excerpt).

Partial Final Award for Case No. 01-22-0002-8455, American Arbitration Association—Commercial Arbitration Tribunal, *Nevro Corp.*, vs *Mayo Foundation for Medical Education and Research; and Venturi Group, LLC*, (Now Flathead Partners LLC), Apr. 8, 2024, 92 pages.
Advanced Bionics—Precision, Physician Implant Manual, Implantable Pulse Generator model SC1100, https://www.fcc.gov/oet/ea/fccid, 2003, 45 pages.
Aronow et al., "Spinal Cord Stimulation for Treatment of Angina Pectoris," Coronary Artery Disease, 2004, 5 pages.
Barolat et al., "Mapping of sensory responses to epidural stimulation of intraspinal neural structures in man," Jourcal of Neurosurgery, vol. 78, Feb. 1993, 7 pages.
De Jongste et al., "Efficacy of Spinal Cord Stimulation as Adjuvant Therapy for Intractable Angina Pectoris: A Prospective, Randomized Clinical Study," JACC, vol. 7, Jun. 1994, 6 pages.
Diedrichs et al., "Symptomatic Relief Precedes Improvement of Myocardial Blood Flow in Patients Under Spinal Cord Stimulation," Current Controlled Trials in Cardiovascular Medicine, 2005, 7 pages.
FDA—Premarket Approval, PMA P030017-S002, Boston Scientific Corp., Precision Spinal Cord Stimulation (SCS), Stimulator, Spinal Cord, Totally Implanted for Pain Relief, Model No. SC-1110, https://www.accessdata.fda.gov/scripts/cdrh/cfdocs/cfpma/pma.cfm?id=P030017, Oct. 1, 2004, 3 pages.
FDA—Premarket Approval, PMA P030017-S008, Approval for Artisan 2x8 Paddle Lead, Model SC-8116-XX for the Precision SCS System, https://www.accessdata.fda.gov/scripts/cdrh/cfdocs/cfpma/pma.cfm?id=P030017S008, Aug. 18, 2005, 3 pages.
FDA, Premarket Approval—PMA P840001-S037, Itrel 3 Spinal Cord Stimulation (SCS) for Treatment of Chronic Intractable Pain of hte Trunk and or Limbs, https://www.accessdata.fda.gov/scripts/cdrh/cfdocs/cfpma/pma.cfm?id=P840001S037, Aug. 29, 1995, 3 p.
Holsheimer et al., "Spinal Geometry and Paresthesia Coverage in Spinal Cord Stimulation," International Neuromodulation Society, 1998, 8 pages.
Mannheimer et al., "Electrical Stimulation Versus Coronary Artery Bypass Surgery in Severe Angina Pectoris—The ESBY Study," American Heart Association, Inc., 1998, 7 pages.
Medtronic—ITREL 3 Neurostimulator 7425 Neurostimulator, Implant Manual, https://www.neuromodulation.ch/sites/default/files/pictures/itrel3 implant manual. pdf, 1995, 20 pages.
Medtronic—Itrel EZ Model 7434A Patient Programmer, User Manual, https://fcc.gov/oet/ea/fccid, 2001, 154 pages.
Medtronic—Spinal Cord Stimulation, Patient Management Guidelines for Clinicians, https://web.archive/org/web/20060522070227/http://medtronic.com/neuro/paintherapies/pain_treatment_ladder/library.html, 1999, 19 pages.
Medtronic—Synergy EZ Model 7435 Patient Programmer, User Manual, https://www.fcc.gov/oet/ea/fccid, 1998, 110 pages.
Medtronic—Synergy, Synergy Versitrel 7427 7427V, Dual-Program Neurostimulators for Spinal Cord Stimulation (SCS), http://www.neuromodulation.ch/sites/default/files/pictures/synergy_implant_manual.pdf, 2003, 96 pages.
Medtronic Activa Parkinson's Control Therapy, Summary of Safety and Effectiveness Data for a Supplemental Premarket Approval Application, PMA P960009/S7, https://www.accessdata.fda.gov/cdrh_docs/pdf/p960009S007b.pdf, Aug. 29, 1995, 30 pages.
Merrill et al., "Electrical Stimulation of Excitable Tissue: Design of Efficacious and Safe Protocols," Journal of Neuroscience Methods, 2005, 28 pages.
Mironer et al., "Pain Tolernace Threshold: A Pilot Study of an Objective Measurement of Spinal Cord Stimulator Trial Results," Pain Medicine, vol. 1, No. 2, 2000, 6 pages.
New Release, "Boston Scientific Announces Launch of New Precision Plus Spinal Cord Stimulation System - Hardware and software innovations offer new benefits to physicans and patients," PRNewswire-First Call, https://news.bostonscientific.com/news-releases?item=58980, 2 pages.
Shaw et al., "1200Hz Sub-Threshold Epidural Stimulation for Pain Control," Shepherd Center, Interventional Pain Management Physician, Shephard Center, Atlanta, GA., 1 page.

(56) References Cited

OTHER PUBLICATIONS

Struijk et al., "Paresthesia Thresholds in Spinal Cord Stimulation: A Comparison of Theoretical Results with Clinical Data," IEEE Transactions on Rehabilitation Engineering, vol. 1, No. 2, Jun. 1993, 8 pages.
Summary of Safety and Effectiveness, PMA P030017, Precision Spinal Cord Stimulator (SCS) System, https://www.accessdata.fda.gov/cdrh_docs/pdf3/P030017B.pdf, 2004, 18 pages.
Petition for Inter Partes Review for U.S. Pat. No. 10,576,286—IPR2022-00512, *Boston Scientific Corporation and Boston Scientific Neuromodulation Corporation* (Petitioners) v. *Nevro Corporation* (Patent Owner), Filed Feb. 15, 2022, 95 pages.
Notice of Filing Date Accorded to Petition and Time for Filing Patent Owner Preliminary Response for U.S. Pat. No. 10,576,286—IPR2022-00512, *Boston Scientific Corporation and Boston Scientific Neuromodulation Corporation* (Petitioners) v. *Nevro Corporation* (Patent Owner), Feb. 24, 2022,5 pages.
Patent Owner's Mandatory Notices for U.S. Pat. No. 10,576,286—IPR2022-00512, *Boston Scientific Corporation and Boston Scientific Neuromodulation Corporation* (Petitioners) v. *Nevro Corporation* (Patent Owner), Filed Mar. 2, 2022, 5 pages.
Petition for Inter Partes Review for U.S. Pat. No. 10,556,112—IPR2022-00511, *Boston Scientific Corporation and Boston Scientific Neuromodulation Corporation* (Petitioners) v. *Nevro Corporation* (Patent Owner), Filed Feb. 15, 2022, 95 pages.
Notice of Filing Date Accorded to Petition and Time for Filing Patent Owner Preliminary Response for U.S. Pat. No. 10,556,112—IPR2022-00511, *Boston Scientific Corporation and Boston Scientific Neuromodulation Corporation* (Petitioners) v. *Nevro Corporation* (Patent Owner), Feb. 24, 2022,5 pages.
Patent Owner's Mandatory Notices for U.S. Pat. No. 10,556,112—IPR2022-00511, *Boston Scientific Corporation and Boston Scientific Neuromodulation Corporation* (Petitioners) v. *Nevro Corporation* (Patent Owner), Filed Mar. 2, 2022, 5 pages.
Exhibit 1003: Declaration of Marom Bikson, Ph.D., Feb. 15, 2022, 128 pages, for Petition for Inter Partes Review for U.S. Pat. No. 10,576,286—IPR2022-00512 and Petition for Inter Partes Review for U.S. Pat. No. 10,556,112—IPR2022-00511, *Boston Scientific Corporation and Boston Scientific Neuromodulation Corporation* (Petitioners) v. *Nevro Corporation* (Patent Owner).
Exhibit 1004: Curriculum Vitae of Marom Bikson, Ph.D., 72 pages, for Petition for Inter Partes Review for U.S. Pat. No. 10,576,286—IPR2022-00512 and Petition for Inter Partes Review for U.S. Pat. No. 10,556,112—IPR2022-00511, *Boston Scientific Corporation and Boston Scientific Neuromodulation Corporation* (Petitioners) v. *Nevro Corporation* (Patent Owner).
Exhibit 1014: Declaration of Natalie Bryan, Feb. 7, 2022, 15 pages, for Petition for Inter Partes Review for U.S. Pat. No. 10,576,286—IPR2022-00512 and Petition for Inter Partes Review for U.S. Pat. No. 10,556,112—IPR2022-00511, *Boston Scientific Corporation and Boston Scientific Neuromodulation Corporation* (Petitioners) v. *Nevro Corporation* (Patent Owner).
Exhibit 1015: Declaration of Dr. Erik Shaw, Feb. 14, 2022, for Petition for Inter Partes Review for U.S. Pat. No. 10,576,286—IPR2022-00512 and Petition for Inter Partes Review for U.S. Pat. No. 10,556,112—IPR2022-00511, *Boston Scientific Corporation and Boston Scientific Neuromodulation Corporation* (Petitioners) v. *Nevro Corporation* (Patent Owner).
Exhibit 1019: Declaration of Michael Henry Verdolin, Feb. 15, 2022, for Petition for Inter Partes Review for U.S. Pat. No. 10,576,286—IPR2022-00512 and Petition for Inter Partes Review for U.S. Pat. No. 10,556,112—IPR2022-00511, *Boston Scientific Corporation and Boston Scientific Neuromodulation Corporation* (Petitioners) v. *Nevro Corporation* (Patent Owner).
Exhibit 1022: Declaration of Thomas L. Yearwood, M.D., Ph.D., 13 pages, for Petition for Inter Partes Review for U.S. Pat. No. 10,576,286—IPR2022-00512 and Petition for Inter Partes Review for U.S. Pat. No. 10,556,112—IPR2022-00511, *Boston Scientific Corporation and Boston Scientific Neuromodulation Corporation* (Petitioners) v. *Nevro Corporation* (Patent Owner).
Exhibit 1034: Curriculum Vitae of Dr. Erik Shaw, 4 pages, for Petition for Inter Partes Review for U.S. Pat. No. 10,576,286—IPR2022-00512 and Petition for Inter Partes Review for U.S. Pat. No. 10,556,112—IPR2022-00511, *Boston Scientific Corporation and Boston Scientific Neuromodulation Corporation* (Petitioners) v. *Nevro Corporation* (Patent Owner).
Exhibit 1035: Declaration of Dr. Richard Boydston North, Feb. 12, 2022, 10 pages, for Petition for Inter Partes Review for U.S. Pat. No. 10,576,286—IPR2022-00512 and Petition for Inter Partes Review for U.S. Pat. No. 10,556,112—IPR2022-00511, *Boston Scientific Corporation and Boston Scientific Neuromodulation Corporation* (Petitioners) v. *Nevro Corporation* (Patent Owner).
Exhibit 1036: Curriculum Vitae of Dr. Richard Boydston North, 53 pages, for Petition for Inter Partes Review for U.S. Pat. No. 10,576,286—IPR2022-00512 and Petition for Inter Partes Review for U.S. Pat. No. 10,556,112—IPR2022-00511, *Boston Scientific Corporation and Boston Scientific Neuromodulation Corporation* (Petitioners) v. *Nevro Corporation* (Patent Owner).
Exhibit 1051: Response to Certificate of Corrections for U.S. Pat. No. 9,002,549, Jan. 25, 2022, 2 pages, for Petition for Inter Partes Review for U.S. Pat. No. 10,576,286—IPR2022- 00512 and Petition for Inter Partes Review for U.S. Pat. No. 10,556,112—IPR2022-00511, *Boston Scientific Corporation and Boston Scientific Neuromodulation Corporation* (Petitioners) v. *Nevro Corporation* (Patent Owner).
Exhibit 1052: Applicant's Reply to Response to the Request for Certificate of Corrections for U.S. Pat. No. 9,002,459, Jul. 28, 2021, 2 pages, for Petition for Inter Partes Review for U.S. Pat. No. 10,576,286—IPR2022-00512 and Petition for Inter Partes Review for U.S. Pat. No. 10,556,112—IPR2022-00511, *Boston Scientific Corporation and Boston Scientific Neuromodulation Corporation* (Petitioners) v. *Nevro Corporation* (Patent Owner).
Patent Owner's Preliminary Response for U.S. Pat. No. 8,892,209 for Inter Partes Review IPR2022-00509, *Boston Scientific Corporation and Boston Scientific Neuromodulation Corporation* (Petitioners) v. *Nevro Corporation* (Patent Owner), Filed May 16, 2022, 86 pages.
Patent Owner's Exhibit List for U.S. Pat. No. 8,892,209 for Inter Partes Review IPR2022-00509, *Boston Scientific Corporation and Boston Scientific Neuromodulation Corporation* (Petitioners) v. *Nevro Corporation* (Patent Owner), Filed May 16, 2022, 10 pages.
Patent Owner's Response to Petitioner's Statement on Parallel Petitions for U.S. Pat. No. 8,892,209 for Inter Partes Review IPR2022-00509, *Boston Scientific Corporation and Boston Scientific Neuromodulation Corporation* (Petitioners) v. *Nevro Corporation* (Patent Owner), Filed May 16, 2022, 8 pages.
Petitioner's Reply to Patent Owner's Preliminary Response for U.S. Pat. No. 8,892,209 for Inter Partes Review IPR2022-00509, *Boston Scientific Corporation and Boston Scientific Neuromodulation Corporation* (Petitioners) v. *Nevro Corporation* (Patent Owner), Filed Jun. 24, 2022, 12 pages.
Petitioner's Updated Exhibit List for U.S. Pat. No. 8,892,209 for Inter Partes Review IPR2022-00509, *Boston Scientific Corporation and Boston Scientific Neuromodulation Corporation* (Petitioners) v. *Nevro Corporation* (Patent Owner), Filed Jun. 24, 2022, 11 pages.
Patent Owner's Sur-Reply for U.S. Pat. No. 8,892,209 for Inter Partes Review IPR2022-00509, *Boston Scientific Corporation and Boston Scientific Neuromodulation Corporation* (Petitioners) v. *Nevro Corporation* (Patent Owner), Filed Jul. 5, 2022, 13 pages.
Joint Motion to Terminate Pursuant to 35 U.S.C. § 317 for U.S. Pat. No. 8,892,209 for Inter Partes Review IPR2022-00509, *Boston Scientific Corporation and Boston Scientific Neuromodulation Corporation (Petitioners)* v. *Nevro Corporation* (Patent Owner), Filed Aug. 5, 2022, 6 pages.
Joint Request that the Settlement Agreement be Treated as Business Confidential Information pursuant to 35 U.S.C. § 317 for U.S. Pat. No. 8,892,209 for Inter Partes Review IPR2022-00509, *Boston Scientific Corporation and Boston Scientific Neuromodulation Corporation* (Petitioners) v. *Nevro Corporation* (Patent Owner), Filed Aug. 5, 2022, 4 pages.
Patent Owner's Preliminary Response for U.S. Pat. No. 8,892,209—IPR2022-00510, *Boston Scientific Corporation and Boston Scien-*

(56) References Cited

OTHER PUBLICATIONS tific Neuromodulation Corporation (Petitioners) v. Nevro Corporation (Patent Owner), Filed May 16, 2022, 80 pages.
Patent Owner's Exhibit List for U.S. Pat. No. 8,892,209—IPR2022-00510, Boston Scientific Corporation and Boston Scientific Neuromodulation Corporation (Petitioners) v. Nevro Corporation (Patent Owner), Filed May 16, 2023, 10 pages.
Petitioners' Reply to Patent Owner's Preliminary Response for U.S. Pat. No. 8,892,209—IPR2022-00510, Boston Scientific Corporation and Boston Scientific Neuromodulation Corporation (Petitioners) v. Nevro Corporation (Patent Owner), Filed Jun. 24, 2022, 12 pages.
Petitioners' Updated Exhibit List for U.S. Pat. No. 8,892,209—IPR2022-00510, Boston Scientific Corporation and Boston Scientific Neuromodulation Corporation (Petitioners) v. Nevro Corporation (Patent Owner), Filed Jun. 24, 2022, 11 pages.
Patent Owners' Sur-Reply for U.S. Pat. No. 8,892,209—IPR2022-00510, Boston Scientific Corporation and Boston Scientific Neuromodulation Corporation (Petitioners) v. Nevro Corporation (Patent Owner), Filed Jul. 5, 2022, 13 pages.
Joint Request that the Settlement Agreement Be Treated as Business Confidential Information Pursuant to 35 U.S.C.§ 317 for U.S. Pat. No. 8,892,209—IPR2022-00510, Boston Scientific Corporation and Boston Scientific Neuromodulation Corporation (Petitioners) v. Nevro Corporation (Patent Owner), Filed Aug. 5, 2022, 4 pages.
Decision—Settlement Prior to Institution of Trial 37 C.F.R. § 42.74 for U.S. Pat. No. 8,892,209—IPR2022-00510; U.S. Pat. No. 8,892,209 for Inter Partes Review IPR2022-00509; U.S. Pat. No. 10,576,286—Inter Partes Review for IPR2022-00512; U.S. Pat. No. 10,556,112—Inter Partes Review for IPR2022-00511—Boston Scientific Corporation and Boston Scientific Neuromodulation Corporation (Petitioners) v. Nevro Corporation (Patent Owner), Filed Aug. 8, 2022, 4 page.
Exhibit 2002: C.V. of Peter Crosby for U.S. Pat. No. 8,892,209—IPR2022-00510 and Petition for Inter Partes Review for U.S. Pat. No. 8,892,209—IPR2022-00509, Boston Scientific Corporation and Boston Scientific Neuromodulation Corporation (Petitioners) v. Nevro Corporation (Patent Owner).
Exhibit 2003: Declaration of Peter Crosby for U.S. Pat. No. 8,892,209—IPR2022-00510 and Petition for Inter Partes Review for U.S. Pat. No. 8,892,209—IPR2022-00509, Boston Scientific Corporation and Boston Scientific Neuromodulation Corporation (Petitioners) v. Nevro Corporation (Patent Owner).
Exhibit 2007: C.V. of Michael Fishman, M.D. for U.S. Pat. No. 8,892,209—IPR2022-00510 and Petition for Inter Partes Review for U.S. Pat. No. 8,892,209—IPR2022-00509, Boston Scientific Corporation and Boston Scientific Neuromodulation Corporation (Petitioners) v. Nevro Corporation (Patent Owner).
Exhibit 2008: Declaration of Michael Fishman, M.D. for U.S. Pat. No. 8,892,209—IPR2022- 00510 and Petition for Inter Partes Review for U.S. Pat. No. 8,892,209—IPR2022-00509, Boston Scientific Corporation and Boston Scientific Neuromodulation Corporation (Petitioners) v. Nevro Corporation (Patent Owner).
Exhibit 2015: Nevro Corp. v. Boston Scientific Corp., 955 F.3d 35 (Fed. Cir. 2020) for U.S. Pat. No. 8,892,209—IPR2022-00510; U.S. Pat. No. 8,892,209 for Inter Partes Review IPR2022-00509; U.S. Pat. No. 10,576,286—Inter Partes Review for IPR2022-00512; U.S. Pat. No. 10,556,112—Inter Partes Review for IPR2022-00511—Boston Scientific Corporation and Boston Scientific Neuromodulation Corporation (Petitioners) v. Nevro Corporation (Patent Owner).
Exhibit 2016: Nevro Corp. v. Boston Scientific Corp., No. 16-cv-06830-VC, 2018 WL 4676501 (N.D. Cal. Jul. 24, 2018) for U.S. Pat. No. 8,892,209—IPR2022-00510 and Petition for Inter Partes Review for U.S. Pat. No. 8,892,209—IPR2022-00509, Boston Scientific Corporation and Boston Scientific Neuromodulation Corporation (Petitioners) v. Nevro Corporation (Patent Owner).
Exhibit 2022: Nevro Corp. v. Boston Scientific Corp., No. 3:16-cv-6830, Dkt. 1, Complaint for Patent Infringement and Declaratory Judgment, Demand for Jury Trial (N.D. Cal. Nov. 28, 2016) for U.S. Pat. No. 8,892,209—IPR2022-00510; U.S. Pat. No. 8,892,209 for Inter Partes Review IPR2022-00509; U.S. Pat. No. 10,576,286—Inter Partes Review for IPR2022—00512; U.S. Pat. No. 10,556,112—Inter Partes Review for IPR2022-00511—Boston Scientific Corporation and Boston Scientific Neuromodulation Corporation (Petitioners) v. Nevro Corporation (Patent Owner).
Exhibit 2023: Nevro Corp. v. Boston Scientific Corp., No. 3:16-cv-06830-VC, Dkt. 554, Stipulation and [Proposed] Order of Dismissal (N.D. Cal. Dec. 14, 2020) for U.S. Pat. No. 8,892,209—IPR2022-00510; U.S. Pat. No. 8,892,209 for Inter Partes Review IPR2022-00509; U.S. Pat. No. 10,576,286—Inter Partes Review for IPR2022-00512; U.S. Pat. No. 10,556, 112—Inter Partes Review for IPR2022-00511—Boston Scientific Corporation and Boston Scientific Neuromodulation Corporation (Petitioners) v. Nevro Corporation (Patent Owner).
Exhibit 2025: Nevro Corp. v. Boston Scientific Corp., No. 1:21-cv-00258-UNA, Dkt. 1, Complaint (D.Del. Feb. 23, 2021) for U.S. Pat. No. 8,892,209—IPR2022-00510; U.S. Pat. No. 8,892,209 for Inter Partes Review IPR2022-00509; U.S. Pat. No. 10,576,286—Inter Partes Review for IPR2022-00512; U.S. Pat. No. 10,556,112—Inter Partes Review for IPR2022-00511—Boston Scientific Corporation and Boston Scientific Neuromodulation Corporation (Petitioners) v. Nevro Corporation (Patent Owner).
Exhibit 2026: Nevro Corp. v. Stimwave Technologies, Inc., No. 1:19-cv-00325-UNA, Dkt. 1, Complaint for Patent Infringement, Declaratory Judgment of Patent Infringement, Violation of the Lanham Act, and Deceptive Trade Practices (D. Del Feb. 14, 2019) for U.S. Pat. No. 8,892,209—IPR2022-00510 and Petition for Inter Partes Review for U.S. Pat. No. 8,892,209—IPR2022-00509, Boston Scientific Corporation and Boston Scientific Neuromodulation Corporation (Petitioners) v. Nevro Corporation (Patent Owner).
Exhibit 2027: Nevro Corp. v. Stimwave Technologies, Inc., No. 1:19-cv-00325-CFC, Dkt. 98, Stimwave's Answering Brief in Opposition to Plaintiff Nevro's Motion for a Preliminary Injunction (D.Del. Jun. 6, 2019) for U.S. Pat. No. 8,892,209—IPR2022-00510 and Petition for Inter Partes Review for U.S. Pat. No. 8,892,209—IPR2022-00509, Boston Scientific Corporation and Boston Scientific Neuromodulation Corporation (Petitioners) v. Nevro Corporation (Patent Owner).
Exhibit 2028: Nevro Corp. v. Stimwave Technologies, Inc., No. 1:19-cv-00325-CFC, Dkt. 231, Stipulated Consent Judgment and Permanent Injunction (D.Del. Mar. 2, 2020) for U.S. Pat. No. 8,892,209—IPR2022-00510 and Petition for Inter Partes Review for U.S. Pat. No. 8,892,209—IPR2022-00509, Boston Scientific Corporation and Boston Scientific Neuromodulation Corporation (Petitioners) v. Nevro Corporation (Patent Owner).
Exhibit 2032: Ex parte Knudson, Appeal No. 2021-001841, Decision on Appeal (PTAB Oct. 26, 2021) for U.S. Pat. No. 8,892,209—IPR2022-00510 and Petition for Inter Partes Review for U.S. Pat. No. 8,892,209—IPR2022-00509, Boston Scientific Corporation and Boston Scientific Neuromodulation Corporation (Petitioners) v. Nevro Corporation (Patent Owner).
Exhibit 2033: Nevro Corp. v. Nalu Medical, Inc., No. 20-291 (CFC)(JLH), Nevro Corp.'s Response to Defendant Nalu Medical, Inc.'s First Set of Interrogatories (Nos. 1-10) (D. Del. May 7, 2021) for U.S. Pat. No. 8,892,209—IPR2022-00510 and Petition for Inter Partes Review for U.S. Pat. No. 8,892,209—IPR2022-00509, Boston Scientific Corporation and Boston Scientific Neuromodulation Corporation (Petitioners) v. Nevro Corporation (Patent Owner).
Exhibit 2035: Boston Scientific Neuromodulation Corporation v. Nevro Corporation, IPR2015-01203, Paper 10, Decision Denying Institution of Inter Partes Review (PTAB Nov. 30, 2015) for U.S. Pat. No. 8,892,209—IPR2022-00510; U.S. Pat. No. 8,892,209 for Inter Partes Review IPR2022-00509; U.S. Pat. No. 10,576,286; Inter Partes Review for IPR2022-00512; U.S. Pat. No. 10,556,112—Inter Partes Review for IPR2022-00511—Boston Scientific Corporation and Boston Scientific Neuromodulation Corporation (Petitioners) v. Nevro Corporation (Patent Owner).
Exhibit 2038: Nevro Corp. v. Nalu Medical, Inc., No. 1:20-cv-00291-CFC, Dkt. 14, First Amended Complaint for Patent Infringement (D. Del Jun. 1, 2020) for U.S. Pat. No. 8,892,209—IPR2022-00510 and Petition for Inter Partes Review for U.S. Pat. No. 8,892,209—IPR2022-00509, Boston Scientific Corporation and Boston Scientific Neuromodulation Corporation (Petitioners) v. Nevro Corporation (Patent Owner).

(56) References Cited

OTHER PUBLICATIONS

Exhibit 2045: *Nevro Corp. v. Stimwave Technologies, Inc.*, No. 19-325-CFC, 2019 WL 3322368 (D.Del. Jul. 24, 2019) for U.S. Pat. No. 8,892,209—IPR2022-00510 and Petition for Inter Partes Review for U.S. Pat. No. 8,892,209—IPR2022-00509, *Boston Scientific Corporation and Boston Scientific Neuromodulation Corporation* (Petitioners) v. *Nevro Corporation* (Patent Owner).

Exhibit 2046: *Nevro Corp. v. Nalu Medical, Inc.*, No. 1:20-cv-00291-UNA, Dkt. 1, Complaint for Patent Infringement (D.Del. Feb. 28, 2020) for U.S. Pat. No. 8,892,209—IPR2022-00510 and Petition for Inter Partes Review for U.S. Pat. No. 8,892,209—IPR2022-00509, *Boston Scientific Corporation and Boston Scientific Neuromodulation Corporation* (Petitioners) v. *Nevro Corporation* (Patent Owner).

Exhibit 2052: U.S. Patent and Trademark Office, Declaration of James Thacker, Application No. 13/705/021 (Dec. 4, 2012) (No. 3: 16-cv-06830-VC, Dkt. 398-13, Exhibit 12 (May 24, 2018) for U.S. Pat. No. 8,892,209—IPR2022-00510 and Petition for Inter Partes Review for U.S. Pat. No. 8,892,209—IPR2022-00509, *Boston Scientific Corporation and Boston Scientific Neuromodulation Corporation* (Petitioners) v. *Nevro Corporation* (Patent Owner).

Exhibit 2055: *Nevro Corp. v. Boston Scientific Corp.*, No. 18-2220, Dkt. 32, Principal and Response Brief for Defendants-Cross-Appellants Boston Scientific Corporation and Boston Scientific Neuromodulation Corporation (Fed. Cir. Jan. 17, 2019) for U.S. Pat. No. 8,892,209—IPR2022-00510 and Petition for Inter Partes Review for U.S. Pat. No. 8,892,209—IPR2022-00509, *Boston Scientific Corporation and Boston Scientific Neuromodulation Corporation* (Petitioners) v. *Nevro Corporation* (Patent Owner).

Exhibit 2060: Inter Partes Review 2021-01203 for U.S. Pat. No. 8,359,102—Patent Owner's Preliminary Response, *Boston Scientific Neuromodulation Corporation.* v. *Nevro Corp.*, Sep. 1, 2015, 70 pages, for Petition for Inter Partes Review for U.S. Pat. No. 8,892,209—IPR2022-00510, *Boston Scientific Corporation and Boston Scientific Neuromodulation Corporation* (Petitioners) v. *Nevro Corporation* (Patent Owner).

Patent Owner's Preliminary Response for U.S. Pat. No. 10,576,286—Inter Partes Review for IPR2022-00512, *Boston Scientific Corporation and Boston Scientific Neuromodulation Corporation* (Petitioners) v. *Nevro Corporation* (Patent Owner), Filed May 24, 2022, 38 pages.

Joint Motion to Terminate Pursuant to 35 U.S.C. 317 for U.S. Pat. No. 10,576,286—Inter Partes Review for IPR2022-00512, *Boston Scientific Corporation and Boston Scientific Neuromodulation Corporation* (Petitioners) v. *Nevro Corporation* (Patent Owner), Filed Aug. 5, 2022, 6 pages.

Joint Request that the Settlement Agreement be Treated as Business Confidential Information Pursuant to 35 U.S.C. 317 for U.S. Pat. No. 10,576,286—Inter Partes Review for IPR2022-00512, *Boston Scientific Corporation and Boston Scientific Neuromodulation Corporation* (Petitioners) v. *Nevro Corporation* (Patent Owner), Filed Aug. 5, 2022, 4 pages.

Patent Owner's Preliminary Response for U.S. Pat. No. 10,556,112—Inter Partes Review IPR2022-00511, *Boston Scientific Corporation and Boston Scientific Neuromodulation Corporation* (Petitioners) v. *Nevro Corporation* (Patent Owner), Filed May 24, 2022, 37 pages.

Joint Motion to Terminate Pursuant to 35 U.S.C. § 317 for U.S. Pat. No. 10,556, 112—Inter Partes Review IPR2022-00511, *Boston Scientific Corporation and Boston Scientific Neuromodulation Corporation* (Petitioners) v. *Nevro Corporation* (Patent Owner), Filed May 24, 2022, 6 pages.

Joint Request that the Settlement Agreement be Treated as Business Confidential Information Pursuant to 35 U.S.C. § 317 for U.S. Pat. No. 10,556,112—Inter Partes Review IPR2022- 00511, *Boston Scientific Corporation and Boston Scientific Neuromodulation Corporation* (Petitioners) v. *Nevro Corporation* (Patent Owner), Filed Aug. 5, 2022, 4 pages.

Exhibit 2002: *Boston Scientific Corp.* v. *Nevro Corp.*, No. 18-644 (CFC), Dkt. 27, Answer, Affirmative Defenses, and Counterclaims to First Amended Complaint (D. Del. Dec. 9, 2019) Inter Partes Review for IPR2022-00512; U.S. Pat. No. 10,556, 112—Inter Partes Review for IPR2022-00511—*Boston Scientific Corporation and Boston Scientific Neuromodulation Corporation* (Petitioners) v. *Nevro Corporation* (Patent Owner).

Exhibit 2003: *Boston Scientific Corp.* v. *Nevro Corp.*, No. 16-1163 (CFC)(Consolidated), Dkt. 551, Claim Construction Order (D. Del. Feb. 25, 2021) Inter Partes Review for IPR2022-00512; U.S. Pat. No. 10,556,112—Inter Partes Review for IPR2022-00511—*Boston Scientific Corporation and Boston Scientific Neuromodulation Corporation* (Petitioners) v. *Nevro Corporation* (Patent Owner).

Exhibit 2036: *Boston Scientific Neuromodulation Corporation* v. *Nevro Corp.*, IPR2015-01204, Paper 10, Decision Denying Institution of Inter Partes Review (PTAB Nov. 30, 2015) Inter Partes Review for IPR2022-00512; U.S. Pat. No. 10,556,112—Inter Partes Review for IPR2022-00511—*Boston Scientific Corporation and Boston Scientific Neuromodulation Corporation* (Petitioners) v. *Nevro Corporation* (Patent Owner).

\* cited by examiner

NEURAL BLOCKING THERAPY

CROSS-REFERENCE TO RELATED APPLICATION

This is a continuation application of U.S. patent application Ser. No. 14/922,009, filed Oct. 23, 2015, entitled NEURAL BLOCKING THERAPY, which is a continuation application of U.S. patent application Ser. No. 14/059,246, filed Oct. 21, 2013, entitled NEURAL BLOCKING THERAPY, which is a continuation application of U.S. patent application Ser. No. 11/235,947, filed on Sep. 26, 2005, entitled NEURAL BLOCKING THERAPY, each of which are incorporated herein by reference.

I. BACKGROUND OF THE INVENTION

1. Field of the Invention

This application pertains to method and apparatus for treating conditions associated with neuronal activity.

2. Description of the Prior Art a. Neural Stimulation Treatments

The prior art contains numerous examples of treatments involving stimulation signals to nerves, muscles or organs for treating a wide variety of medical disorders.

U.S. Pat. Nos. 4,702,254 and 5,229,569 (both assigned to Cyberonics, Inc.) describe various central nervous system (CNS) treatments using electrical stimulation applied to the vagus nerve. For example, the '254 patent describes treatment of epilepsy. The '569 patent describes treatment of neuropsychiatric disorders. U.S. Patent Application Publication No. 2003/0144709 (also assigned to Cyberonics, Inc.) describes treatment of pain through nerve stimulation.

U.S. Patent Application Publication No. 2004/0243205 A1 to Keravel et al. published Dec. 2, 2004 and assigned to Medtronic, Inc., Minneapolis, Minn., USA (incorporated herein by reference) describes a paddle lead with multiple electrodes. The paddle is placed beneath the skull overlying a target area of the cerebral cortex. The electrodes record somaesthetic-evoked potentials. The same electrodes may be used for a stimulation therapy.

Nerve stimulation and muscle stimulation have been suggested for treating gastrointestinal (GI) disorders. Treatments of gastrointestinal diseases through nerve stimulation have been suggested. For example, U.S. Pat. No. 6,238,423 to Bardy dated May 29, 2001 describes a constipation treatment involving electrical stimulation of the muscles or related nerves of the gut. U.S. Pat. No. 6,571,127 to Ben-Haim et al. dated May 27, 2003 describes increasing motility by applying an electrical field to the GI tract. U.S. Pat. No. 5,540,730 to Terry, Jr. et al., dated Jul. 30, 1996 describes a motility treatment involving vagal stimulation to alter GI contractions in response to a sense condition indicative of need for treatment. U.S. Pat. No. 6,610,713 to Tracey dated Aug. 26, 2003 describes inhibiting release of a proinflammatory cytokine by treating a cell with a cholinergic agonist by stimulating efferent vagus nerve activity to inhibit the inflammatory cytokine cascade. U.S. Pat. No. 6,622,047 to Barrett et al. dated Sep. 16, 2003 describes obesity treatment through vagal stimulation.

b. Neural Blocking

The foregoing treatments are stimulation for treatments. For those applying a signal to a nerve, the signal parameters (pulse width, frequency and amplitude) are selected to initiate neural action potentials to be propagated along the nerve to an organ (e.g., brain or stomach).

Not all electrical signals applied to nerves are stimulation signals. Certain parameters can result in a signal that inhibits the nerve or blocks the propagation of action potentials along the nerve.

Many different forms of nerve blocking are known. The present invention is an improvement upon a neural blocking to avoid antidromic influences during stimulation or to otherwise down-regulate nerve activity. Cryogenic nerve blocking of the vagus is described in Dapoigny et al., "Vagal influence on colonic motor activity in conscious nonhuman primates", *Am. J. Physiol.*, 262: G231-G236 (1992). Electrically induced nerve blocking is described in Van Den Honert, et al., "Generation of Unidirectionally Propagated Action Potentials in a Peripheral Nerve by Brief Stimuli", *Science*, Vol. 206, pp. 1311-1312. An electrical nerve block is described in Solomonow, et al., "Control of Muscle Contractile Force through Indirect High-Frequency Stimulation", *Am. J. of Physical Medicine*, Vol. 62, No. 2, pp. 71-82 (1983) and Petrofsky, et al., "Impact of Recruitment Order on Electrode Design for Neural Prosthetics of Skeletal Muscle", *Am. J. of Physical Medicine*, Vol. 60, No. 5, pp. 243-253 (1981). A neural prosthesis with an electrical nerve block is also described in U.S. Patent Application Publication No. U.S. 2002/0055779 A1 to Andrews published May 9, 2002. A cryogenic vagal block and resulting effect on gastric emptying are described in Paterson C A, et al., "Determinants of Occurrence and Volume of Transpyloric Flow During Gastric Emptying of Liquids in Dogs: Importance of Vagal Input", *Dig Dis Sci,* (2000); 45:1509-1516.

A frequency of the blocking signal is greater than a 200 Hz threshold and, preferably, greater than 500 Hz. Solomonow, et al. "Control of Muscle Contractile Force through Indirect High-Frequency Stimulation", *American Journal of Physical Medicine,* Volume 62, No. 2, pages 71-82 (1983). Higher frequencies of as high as 5,000 Hz result in more consistent neural conduction block. Kilgore, et al., "Nerve Conduction Block Utilizing High-Frequency Alternating Current", *Medical and Biological Engineering and Computing,* Vol. 42, pp. 394-406 (2004).

The nerve conduction block is applied with electrical signals selected to block the entire cross-section of the nerve (for example, both afferent, efferent, myelinated and non-myelinated fibers) at the site of applying the blocking signal (as opposed to selected sub-groups of nerve fibers or just afferent and not efferent or vice versa).

c. Use of Neural Blocking in Treatments

U.S. Pat. No. 5,188,104 to Wernicke et. al. dated Feb. 23, 1993 describes sub-selection of fibers in a nerve by selecting a treatment frequency which blocks certain nerve fiber types in the nerve while stimulating other nerve fiber types. Since certain fibers are stimulated while other fibers are blocked, there is no cross-section inhibition or blocking of the entire nerve and all of its nerve fiber types (for example, both afferent, efferent, myelinated and non-myelinated fibers).

U.S. Pat. No. 6,684,105 to Cohen et al. dated Jan. 27, 2004 (assigned to BioControl Medical Ltd.) teaches collision blocking in which a stimulation signal is applied to nerves and an appropriately timed stimulus is applied to nerves to create neural impulses which collide with and thereby block propagation of the stimulation signal in a given direction. No therapy is achieved by the blocking. Such blocking avoids adverse side effects associated with permitting the stimulation signal propagating in an undesired direction to an organ not targeted for therapy.

U.S. Patent Application Publication No. 2002/0055779 A1 published May 9, 2002 describes applying a high frequency block to a sciatic nerve to block undesired neural impulses which would otherwise contribute to spastic movement. With such spasm-inducing signals blocked, a therapy signal is applied to the muscle to stimulate desired muscle contractions. U.S. Patent Application Publication No. 2005/0149148 A1 published Jul. 7, 2005 (assigned to Medtronic, Inc.) teaches using a blocking signal to avoid undesired side effects (i.e., pain) otherwise associated with a stimulation signal.

The use of a blocking signal as a therapy is described in various patent applications assigned to EnteroMedics, Inc. These applications pertain to use of a conduction block technology to a nerve for a treatment of a variety of disorders. These applications include the following (all filed Sep. 29, 2003): U.S. patent application Ser. No. 10/674,330 (published Sep. 2, 2004 as Publication No. U.S. 2004/0172086 A1); U.S. patent application Ser. No. 10/675,818 (published Sep. 9, 2004 as U.S. Patent Application Publication No. U.S. 2004/0176812 A1) and U.S. patent application Ser. No. 10/674,324 (published Sep. 2, 2004 as U.S. Patent Application Publication No. 2004/0172085 A1). The same assignee is assigned U.S. patent application Ser. Nos. 10/752,994 and 10/752,940, both filed Jan. 6, 2004 with respective publication dates of Aug. 26, 2004 and Sep. 2, 2004, Publication Nos. U.S. 2004/0167583 A1 and 2004/0172088 A1.

The foregoing EnteroMedics patent applications describe, in a preferred embodiment, the application of neural conduction block therapy to a vagus nerve alone or in combination with a stimulation of the nerve. The conduction block therapy of these patent applications includes application of an electrical signal with parameters selected to down-regulate vagal activity by creating conditions in which normal nerve propagation potentials are blocked at the application of the signal on both afferent and efferent nerve fibers of the vagus. Representative treatments described in these applications include the treatment of obesity, pancreatitis, pain, inflammation, functional GI disorders, irritable bowel syndrome and ileus.

d. Accommodation

Blockage of a nerve can result in nerve accommodation in which other nerve groups assume, in whole or in part, the function of the blocked nerve. For example, sub-diaphragm blocking of the vagus nerve may be accommodated by the enteric nervous system. U.S. patent application Ser. No. 10/881,045 filed Jun. 30, 2004 (published Feb. 17, 2005 as Publication No. U.S. 2005/0038484 A1) (assigned to EnteroMedics, Inc.) notes that a duty cycle of electrical impulses to the nerve to block neural conduction on the nerve can be adjusted between periods of blocking and no blocking in order to vary the amount of down regulation of the vagus nerve as well as preventing accommodation by the enteric nervous system.

e. Drug Treatments

Many symptoms of Parkinson's disease can be controlled with one of many currently available medications. These are divided into several classes of drugs including dopamine agonists, levodopa/decarboxylase inhibitors, anticholinergic agents, MAO-B inhibitors, and COMT (catechol-O-methyl-transferase) inhibitors. These medications, whether used alone or in combination, not only replace the dopamine that has been lost in the brain, but also slow the rate of dopamine loss in the brain, and/or correct the imbalance between the levels of dopamine and acetylcholine in the brain. While none of these medications are a cure for Parkinson's disease, they can alleviate the symptoms of the disease and help its victims manage the disease.

One of the most effective and widely administered medications introduced in the 1970's to relieve symptoms of Parkinson's disease works as a dopamine replacement therapy. This drug is known as Sinemet (generic name of levodopa/carbidopa), its active ingredient being L-DOPA (L-3,4-dihydroxyphenylalanine). Levodopa is a generic name given to L-DOPA when it is produced as a drug. Unfortunately, dopamine cannot be administered directly to patients because it does not cross the blood-brain barrier. Hence, L-DOPA, which is the precursor form of dopamine, crosses the blood-brain barrier, and can be converted to dopamine in the brain, is the molecule of choice. However, due to the presence of aromatic L-amino acid decarboxylase (AADC) in the periphery of the brain, which will convert L-DOPA to dopamine before it crosses the blood-brain barrier and prevent its passage to the brain, L-DOPA is administered with carbidopa, an AADC inhibitor. Carbidopa inhibits peripheral AADC action and thus reduces the amount of levodopa needed.

During the first few months the medication is administered, its benefits are maximal. However, patients taking Sinemet for a longer period are prone to the "wearing-off" effect, a tendency for the effectiveness of the drug to be lost with time. Hence, the dose of Sinemet will often have to be increased with time. Sometimes an "on-off effect," where the symptoms become sporadic and unpredictable over a period of time, is also experienced. Moreover, as the dose of the medication is increased, some patients begin to experience side effects due to an increase in brain dopamine levels. Some major side effects include anxiety, agitation, dyskinesia, vomiting, low blood pressure, hallucination and nausea (Nadeau 1997). The occurrence of side effects limits the further increase in Sinemet's dosage and, at this point, treatment options become limited. Fortunately, carbidopa minimizes the incidence of vomiting and nausea. Furthermore, although levodopa/carbidopa treatment decreases bradykinesia and rigidity, it may not relieve tremor and balance.

Sinemet (unlike most medications that are absorbed into blood through the stomach) is absorbed from the small intestine. Anything that delays the movement of food from the stomach to the small intestine, such as foods rich in fat and protein, can reduce the amount of the drug absorbed. Moreover, levodopa has a very short plasma half-life. It disappears from the blood in 60 to 90 minutes. Because it is a type of amino acid called a large neutral amino acid (LNAA), it attaches itself during absorption to carrier molecules in the wall of the intestine and is then carried to the blood. Similarly, once in the blood, carrier molecules carry it across the blood-brain barrier. Amino acids such as isoleucine, leucine, valine, phenylalanine, tryptophan and tyrosine compete for the carrier with levodopa. Hence, a diet rich in protein can further compete with Sinemet for entry into the brain. Thus, it is important to carefully evaluate one's diet when taking Sinemet.

Another medication that can be used alone or in combination with Sinemet is Eldepryl (generic name of selegiline). Selegiline is classified as an MAO-B inhibitor and is often administered in 5 mg capsules to help keep the Sinemet dose lower over time and therefore extend its administration period. In certain cases, it can delay the need for levodopa therapy by up to a year. By blocking the action of MAO-B, selegiline extends the capabilities of the dopamine in the synapse, delaying the breakdown of naturally occurring dopamine and dopamine administered as L-DOPA. Eldepryl thus slows dopamine loss in the synapse and makes it more likely that a dopamine will reach its corresponding receptor on the receiving nerve cell and transmit the correct message down the dopamine circuit. This is often referred to as dopamine conservation therapy.

During the Fourth International Congress of Movement Disorders held in Vienna during the summer of 1996, Eldepryl's benefits when administered in combination with Sinemet were affirmed. In fact, patients taking the drug combination were shown to experience motor fluctuations 1.8 years later on average than those taking only Sinemet. Another advantage of taking Eldepryl is that there is no specific dietary restriction associated with it if taken at the 5 mg dosage. Selegiline is an easy drug to take and has further been shown to protect the dopamine-producing neurons against the toxicity of MPTP. However, selegiline has its drawbacks. Patients have been known to experience side effects such as nausea, orthostatic hypotension and insomnia.

Dopamine agonists comprise another general category of drugs. Parlodel (generic name of bromocriptine), Permax (generic name of pergolide) and Symmetrel (generic name of amantadine) are examples. Parlodel and Permax mimic the action of dopamine by interacting with dopamine receptors in a form of dopamine substitution therapy. These two drugs enter the brain directly at dopamine receptor sites and prolong the duration of Sinemet's effects. An advantage of this approach is that it is less likely to cause dyskinesias (the occurrence of abnormal involuntary movements that results from the intake of high doses of L-DOPA). This is because the actual levels of dopamine do not increase in the brain, as is the case with Sinemet. Rather, a substitute form of dopamine is being used. However, these two drugs are less effective than L-DOPA in decreasing bradykinesia and rigidity and induce side effects such as paranoia, hallucinations, confusion, nausea and vomiting.

Symmetrel is an anti-viral drug used as a dopamine-releasing therapy in combination with Sinemet. It works by allowing the presynaptic neuron to more easily release dopamine into the synapse. More recently, it has been suggested that Symmetrel acts by binding to glutamate receptors in the subthalamic nucleus to help redress the imbalance in basal ganglia activity due to a deficiency in dopamine in a synergistic manner. Symmetrel is either used alone in the first stages of PD or in combination in the later stages. However, its effectiveness is known to wear off in a third to a half of the patients taking it. Furthermore, it induces side effects such as edema, blurred vision, depression, confusion and mottled skin.

Two new drugs, after having undergone extensive clinical trials, were made available in 1997. Requip (generic name of ropinirole) and Mirapex (generic name of pram ipexole) are dopamine agonists. They are selective for the dopamine D3 receptor and are selectively targeted toward the basal ganglia. Both Requip and Mirapex can be used alone or with levodopa and both show fewer side effects than other drugs (Lozano et al. 1998).

Artane and Cogentin represent yet another class of drugs. They are classified as anticholinergic agents and are used to restore the imbalance between dopamine and acetylcholine levels in the brain. They work to reduce the activity of acetylcholine and hence reduce the tremor and stiffness of muscle that comes about as a result of having more acetylcholine than dopamine in the brain.

Until the introduction of L-DOPA, anticholinergic agents were the main treatments for Parkinson's disease. Now Artane and Cogentin are usually administered in combination with other medications for their therapeutic effect. While effective, these drugs can also have side effects such as blurred vision, urinary retention, dry mouth, memory loss, and constipation. Hence, they are of limited use to the older population because they can cause serious neuropsychiatric side effects.

Tasmar (generic name of tolcapone) is a drug classified as a COMT inhibitor. COMT is a peripheral enzyme that reduces levodopa to a less active form. Tasmar, which became available in February 1998, has a different action than that of the dopamine agonists, in that when COMT activity is blocked, dopamine remains in the brain for a longer period of time. Hence, when administered with levodopa, COMT inhibitors prolong the duration time of Sinemet.

II. SUMMARY OF THE INVENTION

A method and apparatus are disclosed for treating a variety of conditions. These include treating a disorder associated with neural activity near a region of a brain. In such condition, the method includes placing an electrode to create a field near said region, creating said field with parameters selected to at least partially block neural activity within said field. For treating a tissue sensation, the method includes identifying a target area of tissue to be treated and placing an electrode to create a field near the target area, and creating the field with parameters selected to at least partially block neural activity within the target area. For treating a condition associated with neural activity of a spinal cord, the method includes placing an electrode to create a field near a nerve associated with the spinal cord, and creating the field with parameters selected to at least partially block neural activity within the nerve.

III. BRIEF DESCRIPTION OF THE DRAWINGS

IV. DESCRIPTION OF A PREFERRED EMBODIMENT

With reference now to the various drawing figures in which identical elements are identically numbered, preferred embodiments of the present invention will now be described.

A. Central Nervous System (CNS) Treatment

Certain disorders (e.g., epilepsy and Parkinson's disease and other motor disorders of CNS origin) are believed to be associated with hormonal imbalance.

Movement disorders associated with cerebral activity are not fully understood. However, certain disorders such as epilepsy and Parkinson's disease are believed to be associated with an imbalance of hormonal production deep within the brain.

For example, certain regions deep within the brain produce the hormones glutamate and dopamine. Glutamate enhances conductivity of the nerve cells of the brain, while dopamine reduces or inhibits such conductivity.

Figure 3:
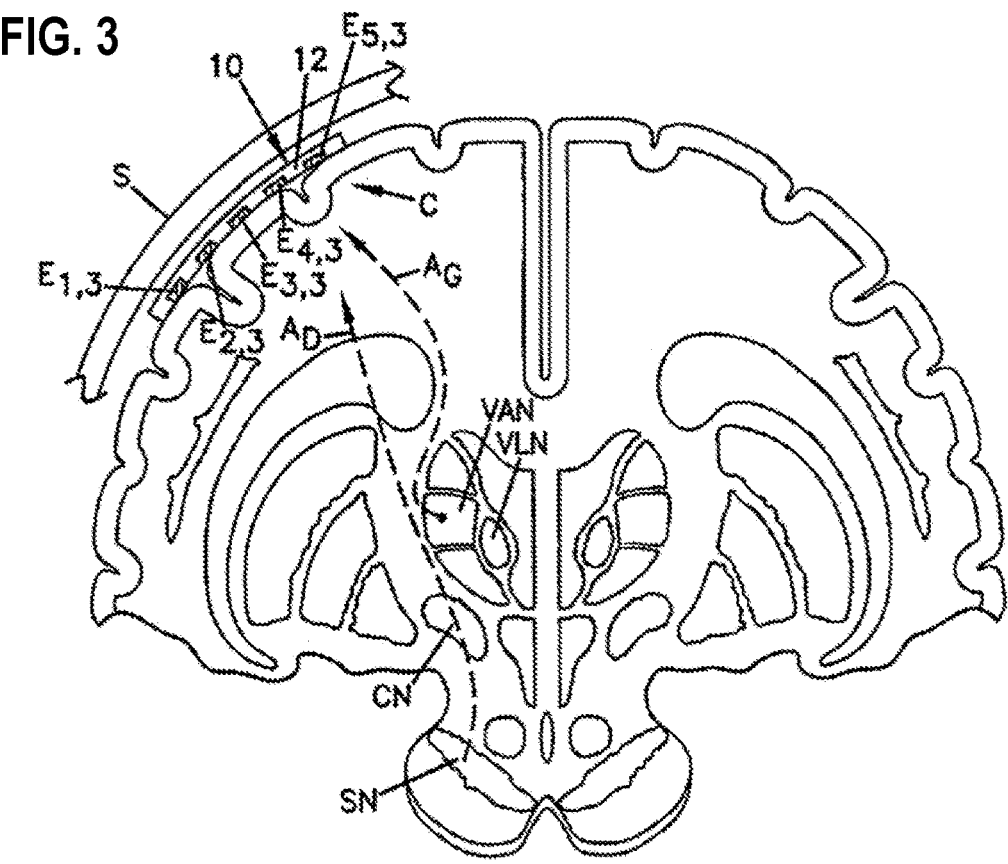
FIG. 3 is a view of a brain of a patient shown in lateral cross-section and with a patch according to the present invention residing between the skull and the surface of the patient's brain over a cortex of the patient's brain.

With reference to FIG. 3, dopamine is produced within a region of the brain known as the substantia nigra (SN). Glutamate is produced in the thalamus region of the brain, which includes the ventral anterior nucleus (VAN), the ventral lateral nucleus (VLN) and the centromedian nucleus (CN). The produced hormones are projected throughout the brain, including to the cortex, which is the outer region of the brain near the back of the head and illustrated generally by C in FIG. 3.

The projection to the cortex C of the glutamate is believed to flow from production of glutamate in the ventral anterior nucleus (VAN). Such projection is illustrated by the arrow $A_G$ in FIG. 3. The projection of dopamine to the cortex is believed to flow from the substantia nigra (SN), with such projection illustrated in FIG. 3 by the arrow AD.

The presence of dopamine and glutamate in the cortex C alter the conductivity of the nerve cells in the cortex C. Certain motor disorders, such as epilepsy and Parkinson's disease, are believed to be associated with a deficiency of dopamine production, which results in excessively enhanced conductivity in the cortex since the enhancing hormone, glutamate, is disproportionately high relative to the inhibiting conductivity hormone, dopamine.

The present invention compensates for hormonal imbalance resulting in excessive conductivity by altering the conductivity at the cortex. The conductivity of the cortex and electrical activity of the cortex controls motor functions of the patient.

The present invention is a patch electrode 10, which is placed beneath the skull of the patient between the skull S and the cortex C (FIG. 3). The patch electrode 10 includes a flexible flat substrate 12 of electrically insulating material such as silicone or the like. Exposed on one surface of the substrate 12 are a plurality of electrically conductive electrodes, which, in a preferred embodiment, are arranged in an array of rows and columns.

Figure 4:
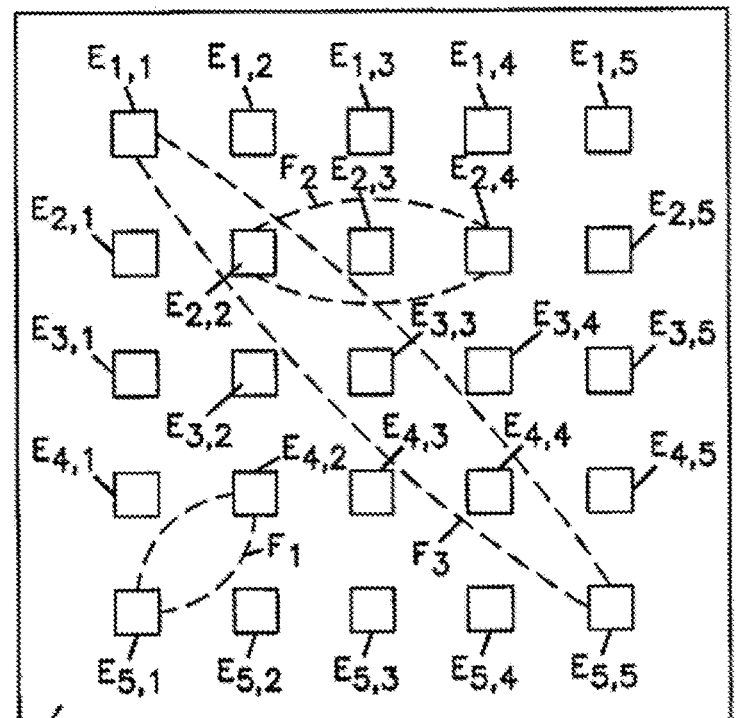
FIG. 4 is a plan view of an electrode patch according to the present invention.

In the specific examples shown in FIGS. 3 and 4, there is a first row containing electrodes $E_{1,1}$ through $E_{1,5}$. The second row contains five electrodes $E_{2,1}$ through $E_{2,5}$. The third row contains electrodes $E_{3,1}$ through $E_{3,5}$. The fourth row contains electrodes $E_{4,1}$ through $E_{4,5}$. The fifth row contains electrodes $E_{5,1}$ through $E_{5,5}$. The patch 10 is dimensioned for the array of electrodes to cover at least a portion of the cortex C of the brain and with the electrodes of the array in electrically conductive contact with the cortex C.

Figure 1:
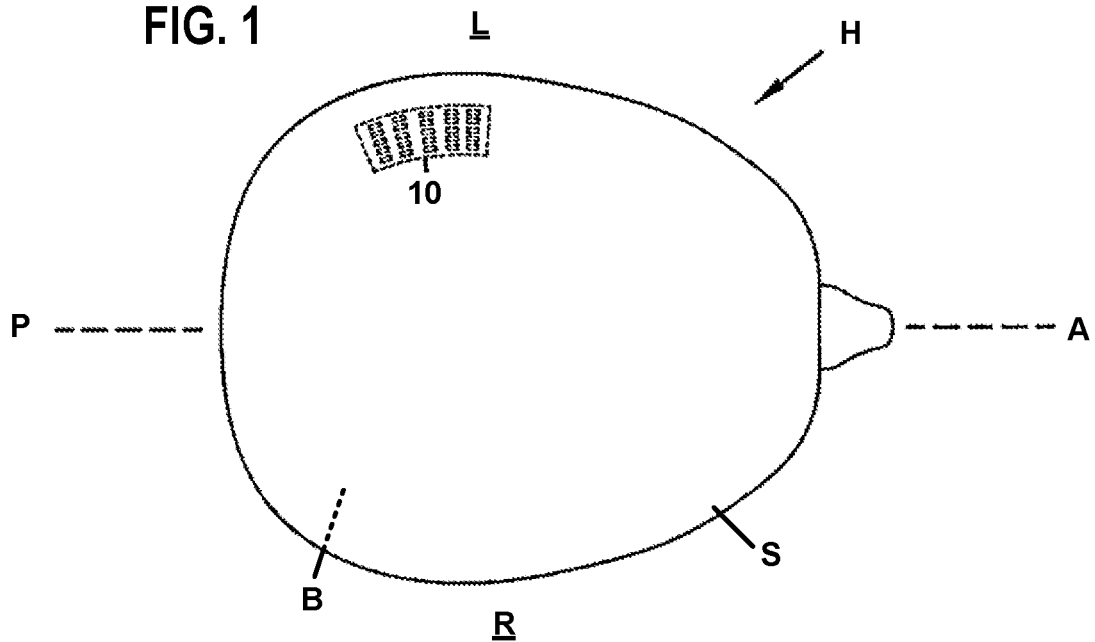
FIG. 1 is a top plan view of a patient's head and showing an electrode array according to the present invention in phantom lines positioned beneath a skull of the patient.
Figure 2:
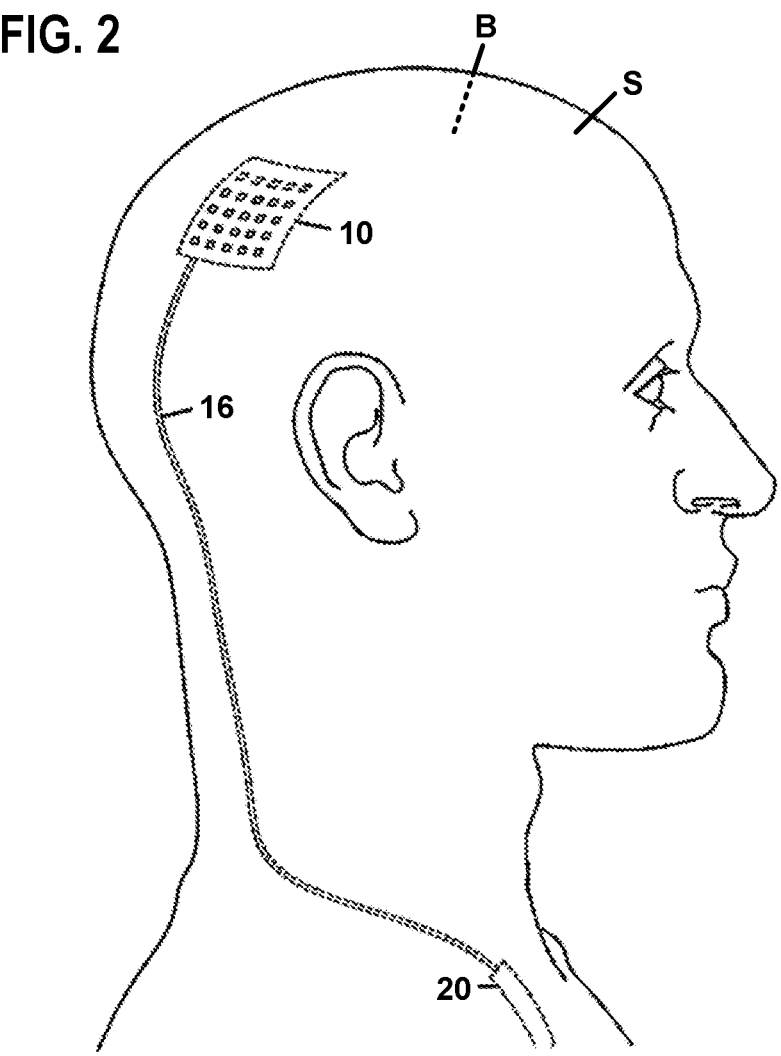
FIG. 2 is a side elevation view of a patient with an electrode patch beneath the skull of the patient and shown in phantom lines with a lead to a control unit positioned in the patient's neck.

As illustrated in FIGS. 1 and 2, the patch electrode 10 is placed over the cortex beneath the skull on either the left (FIG. 1) or right (FIG. 2) of the brain. In FIG. 1, the top of a patient's head H is shown with an anterior-posterior axis A-P separating the 'patient's left L and right R sides.

As shown in FIG. 2, a lead 16 from the patch electrode 10 may be tunneled between the skull S and the brain B through the base of the skull and terminated at a control unit 20, which may be positioned within the neck or implanted lower in the patient, such as in the shoulder or clavicle area or the like. The lead 16 is a highly flexible conductor containing individual conductors for each of the electrodes of the array of the patch 10 and encased within a highly flexible insulative material such as silicone or the like.

The controller 20 may be an implantable pulse generator (with a separate power source such as either rechargeable batteries or replaceable batteries) or may be a control unit, which receives power and pacing signals from an external control unit, which transmits via radio frequency transmission to the controller 20. For the purpose of this description, the controller 20 will be treated as a completely contained controller having both logic circuits and power source. It will be appreciated that such controllers may also be programmable from external programmable sources as is known in the art for controlling implantable pulse generators for cardiac pacing.

The circuitry of the controller 20 permits energizing selective ones of the electrodes of the array in bipolar electrode pairs. For example, electrodes $E_{5,1}$ and $E_{4,2}$ may be energized with oppositely polarized waveforms to create an electrical field $F_1$ between the electrodes $E_{5,1}$ and $E_{4,2}$. By oppositely charged waveforms, it will be appreciated that electrode $E_{5,1}$ is positively charged while $E_{4,2}$ is negatively charged and $E_{5,1}$ is negatively charged while $E_{4,2}$ is positively charged. When the electrode pair $E_{5,1}$ and $E_{4,2}$ is charged to create the field $F_1$, all remaining electrodes may be inactive or otherwise charged to create more complex electrical fields.

FIG. 4 illustrates a field $F_2$ created between electrode pairs $E_{2,2}$ and $E_{2,4}$ and a field $F_3$ between electrode pairs $E_{1,1}$ and $E_{5,5}$. While multiple electrode pairs may be simultaneously charged, the controller 20 may also control the electrodes so that the waveform applied to the electrodes has a built-in delay period such that a particular electrode pair is not charged and in its delay period, while other electrode pairs are being charged. Accordingly, multiple pairs of electrodes may be charged with the waveforms of the electrode pairs being nested so that only one electrode pair is charged at any one unit of time. An example of a nested set of waveforms will be later described.

Preferably, the waveform selected is a blocking waveform to block neuronal activity. For example, the frequency of the field will have a pulse width selected for the generated field to have a frequency in excess of a 200 Hz threshold as described by Solomonow (article previously described) and, more preferably, 5,000 Hz or higher as described in Kilgore (article previously described). A 5,000 Hz signal will have a pulse width of about 100 microseconds. A representative amplitude for such signals would be 0.2 to 8 mA.

The effect of applying a blocking signal to the cortex reduces the excessive electrical activity otherwise associated with a dopamine deficiency. Further, the therapy of the present invention is localized to the area of interest, namely, the cortex region of the brain, which contributes to the symptoms of motor disorders. Other regions of the brain are not affected and no systemic drug is given to the patient.

The programming of the controller 20 may permit altering the selected individual electrodes, which form an electrode pair. Any two electrodes on the patch 10 may be formed to a pair to create a field between the pair. As a result, at time of placement of the patch 10, the patch need not be precisely placed to achieve an interruption or inhibition of electrical activity in the cortex. Instead, different permutations of coupled electrode pairs may be tested to observe patient response post-surgery.

Figure 5:
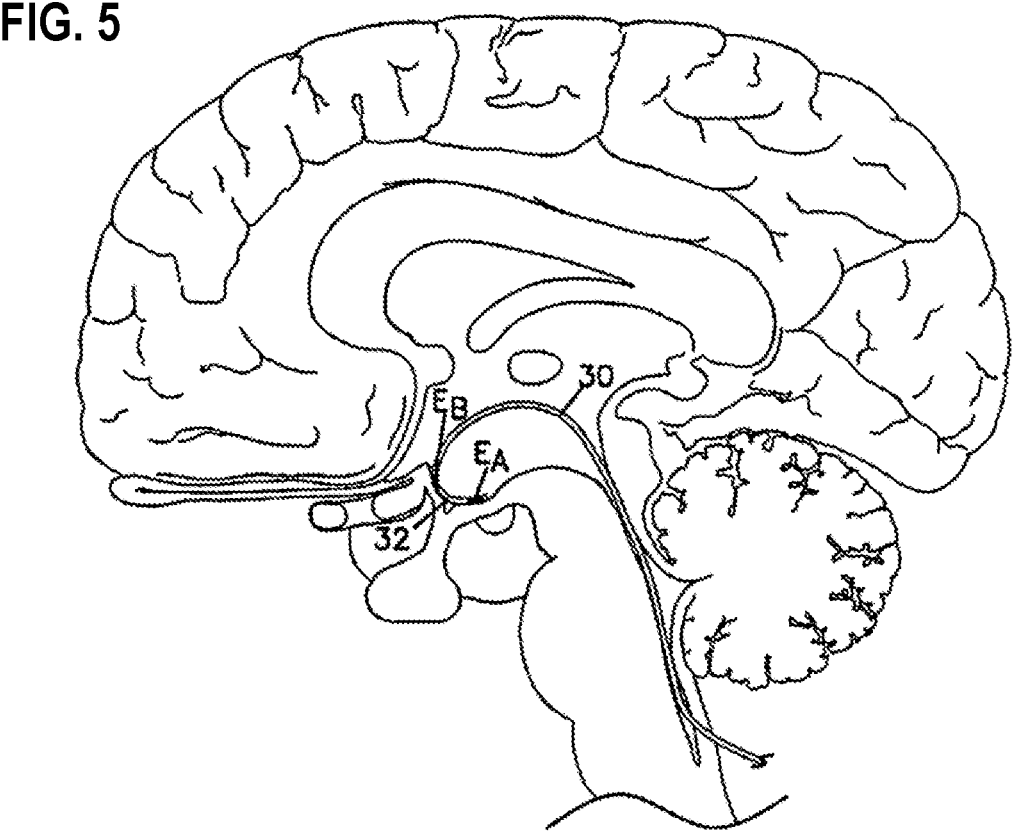
FIG. 5 is an anterior-posterior, cross-sectional view of a patient's brain showing an alternative embodiment of electrodes placed on a catheter advanced through the ventricle of the brain.

The foregoing has illustrated use of the blocking signals to compensate and down-regulate cortex electrical conductivity in response to dopamine deficiency. FIG. 5 illustrates use of stimulation signals to result in localized production of dopamine. In FIG. 5, a catheter 30 is advanced into the ventricles of the brain with a distal tip 32 positioned in the region of the hypothalamus of the brain. The tip 32 includes an electrode pair $E_A$ and $E_B$, which form a bipolar electrode pair. The electrodes are individually electrically connected to a controller (not shown, but such as controller 20 previously described) for creating a desired waveform (as will be described). The controller provides the electrodes with either a stimulation signal (for example, 20 Hz or any other signal less than 200 Hz) or a blocking signal as previously described. Energizing the electrodes with a stimulation signal can be tested on a particular patient to note any increase in dopamine production and result in cortex activity. Similarly, a blocking signal can be applied to note any reduction in glutamate production.

B. Peripheral Nervous System Treatment

The use of blocking signals as described may be used to alleviate pain on the surface of the skin for a wide variety of applications. For example, FIGS. 6 and 7 illustrate a patch 110, which may be placed on the skin surrounding a target area T associated with pain.

Figure 6:
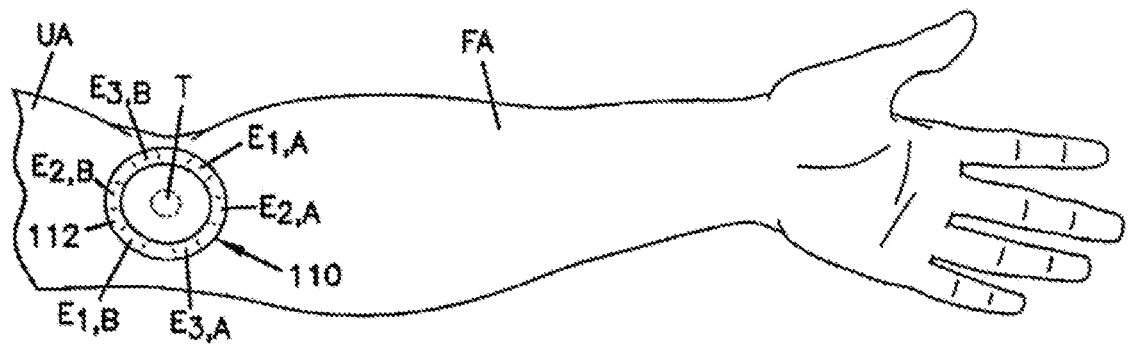
FIG. 6 is a plan view of inside surfaces of an upper arm and forearm and hand of a patient with an alternative embodiment of the present invention positioned surrounding a target area for needle insertion.
Figure 7:
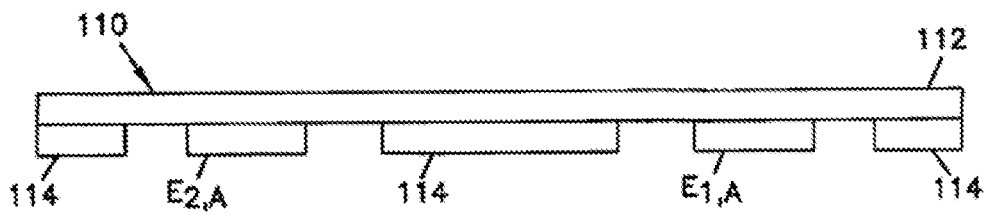
FIG. 7 is a side elevation view of a section of the electrode patch of FIG. 6.

In the particular illustration of FIG. 6, a 'patient required to give blood samples frequently requires a needle injection into the interior surface of the arm to insert a needle into a vein between the upper arm UA and the forearm FA. The health care technician's identification of the particular vein for puncture is identified and circled by a target area T in phantom lines in FIG. 6.

A patch 110 is a ring-shaped substrate 112 sized to surround the target area T but otherwise permits access to the target area T by a needle (not shown) for drawing blood or the like. An undersurface of the substrate 112 contains diametrically opposite electrode pairs $E_{1,A}$, $E_{1,B}$, $E_{2,A}$, $E_{2,B}$ and $E_{3,A}$, $E_{3,B}$. The electrodes are individually electrically connected to a controller (not shown, but such as controller 20 previously described) for creating a desired waveform (as will be described). Between the electrodes, adhesive layers 114 are provided to secure the patch 110 in place on the patient's skin surrounding the target area T.

The individual electrode pairs are bipolar electrode pairs, which may be provided with a blocking signal as previously described. For example, the electrode pair $E_{1,A}$, $E_{1,B}$ may be provided with a first waveform $W_1$ illustrated in FIG. 8. The electrode pair $E_{2,A}$, $E_{2,B}$ may be provided with a second waveform $W_2$ and electrode pair $E_{3,A}$, $E_{3,B}$ may be provided with a third waveform $W_3$ in FIG. 8.

Each of the waveforms $W_1$, $W_2$ and $W_3$ are identical differing only in their timing. The waveforms are preferably blocking waveforms having a frequency in excess of a few hundred Hz threshold and more preferably having a frequency of about 5,000 Hz. With such a frequency, the waveforms have a pulse duration D of 100 microseconds. Preferably, each cycle of the waveform has a delayed period DPD between the pulses with the duration of the delay period DPD equal to two complete cycles (i.e., four pulse durations D or 400 microseconds). The amplitude of the pulse A may be any suitable amplitude to encourage current flow between the electrode pairs. To drive current across the skin, higher energy levels are anticipated (e.g., voltages up to about 35 volts and currents up to 25 mA).

Figure 8:
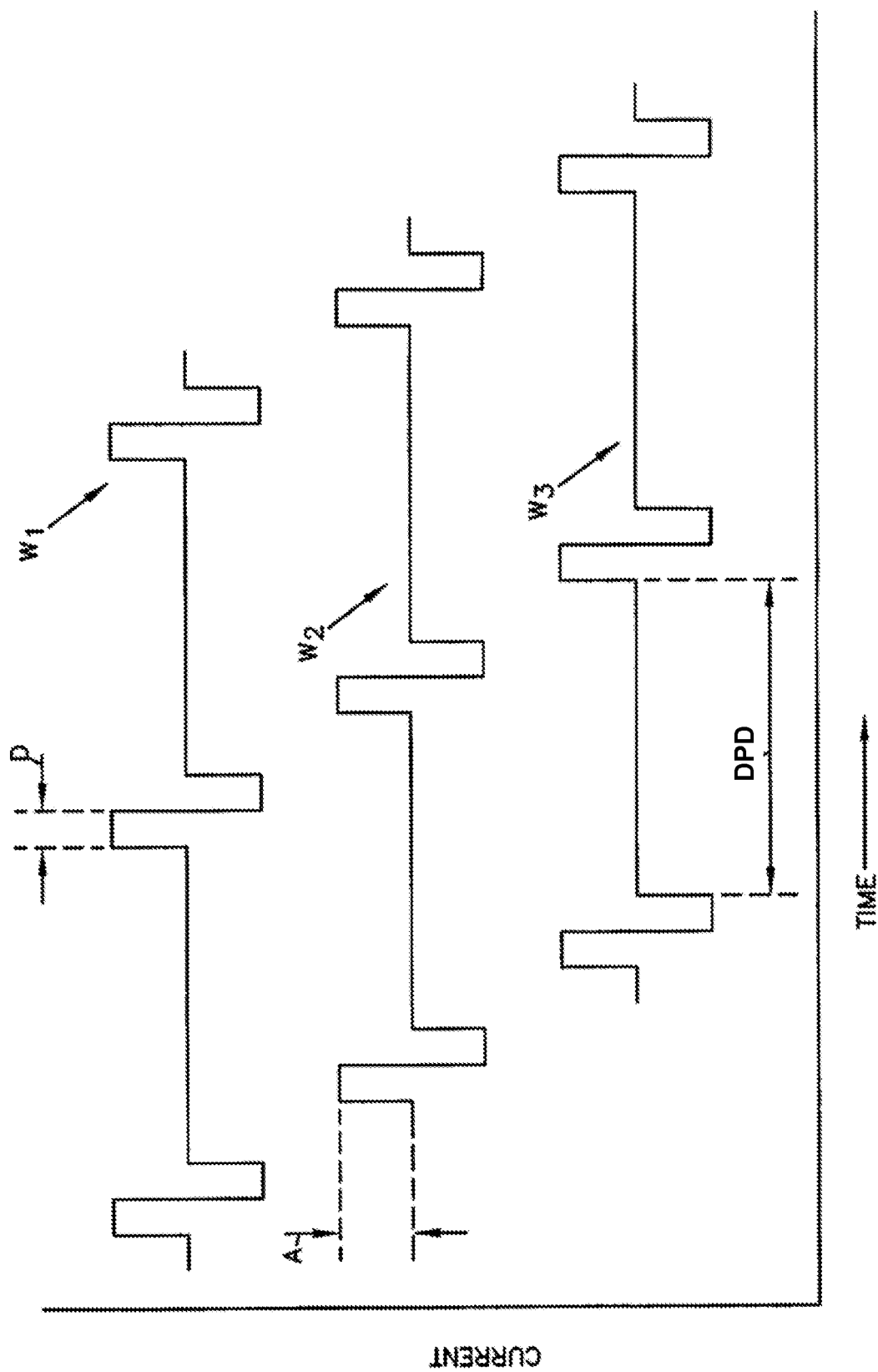
FIG. 8 is a graphical presentation of representative waveforms according to the present invention for energizing the electrodes of FIG. 6.

The waveforms are offset relative to one another so that when any one electrode pair is receiving a pulse, the other electrode pairs are inactive, resulting in three nested waveforms as illustrated in FIG. 8. Such waveforms create an electrical field between the diametrically opposed electrodes of a particular pair, with the field passing through the target area T to block neuronal activity within the target area. Accordingly, when the electrodes are energized with the blocking signals as described, pain is not sensed during needle insertion into the target area T.

It will be appreciated that in FIG. 6, the patch 110 will further include electrical leads to a control unit, both of which are not shown for ease of illustration.

Figure 9:
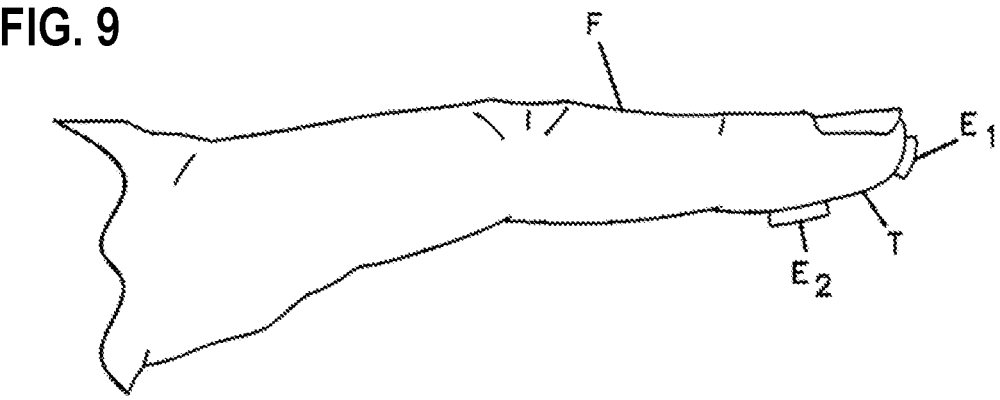
FIG. 9 is an illustration of a patient's finger showing electrodes on the opposite side of a target area at the fingertip of the patient.

FIG. 9 illustrates an alternative application where two electrodes $E_1$ and $E_2$ are placed on opposite sides of a target area T near the fingertip of a patient's finger F. For ease of illustration, a substrate for the electrodes is not shown. The electrodes are individually electrically connected to a controller (not shown, but such as controller 20 previously described) for creating a desired waveform. The application of FIG. 9 is particularly useful for numbing a fingertip prior to lancing the fingertip for a blood sample for periodic blood sugar tests by diabetic patients.

Figure 10:
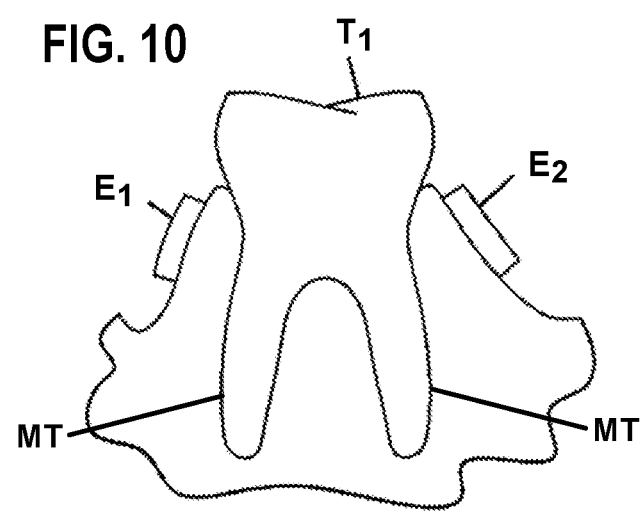
FIG. 10 illustrates electrodes on mucosal tissue on opposite sides of a tooth to apply a blocking signal.

FIG. 10 illustrates a still further embodiment where electrodes $E_1$ and $E_2$ are placed on opposite sides of the gum of the patient overlying mucosal tissue MT on opposite sides of a tooth $T_1$. Application of a blocking signal as previously described to the electrodes creates a blocking field to block nerves within the mucosal tissue for treatment of pain associated with gums or teeth or to precondition the tissue prior to injection of local anesthetics such as Novocain or Lidocaine or other procedure occurring at the tissue.

C. Spinal Cord Treatment

Figure 11:
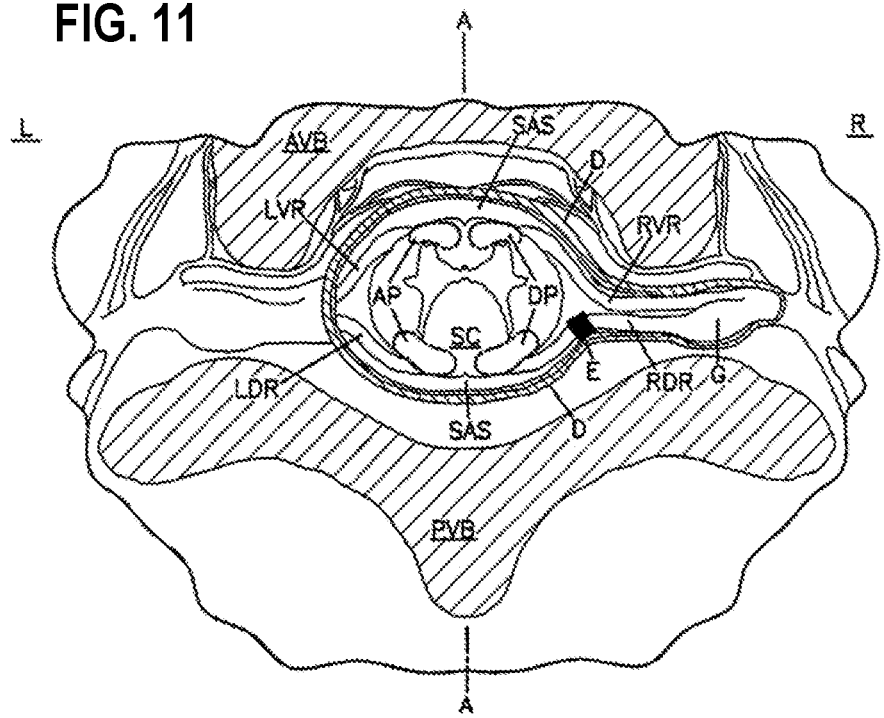
FIG. 11 is a cross-sectional view of a vertebral body and showing anatomical components and a blocking signal electrode on a dorsal root.
Figure 12:
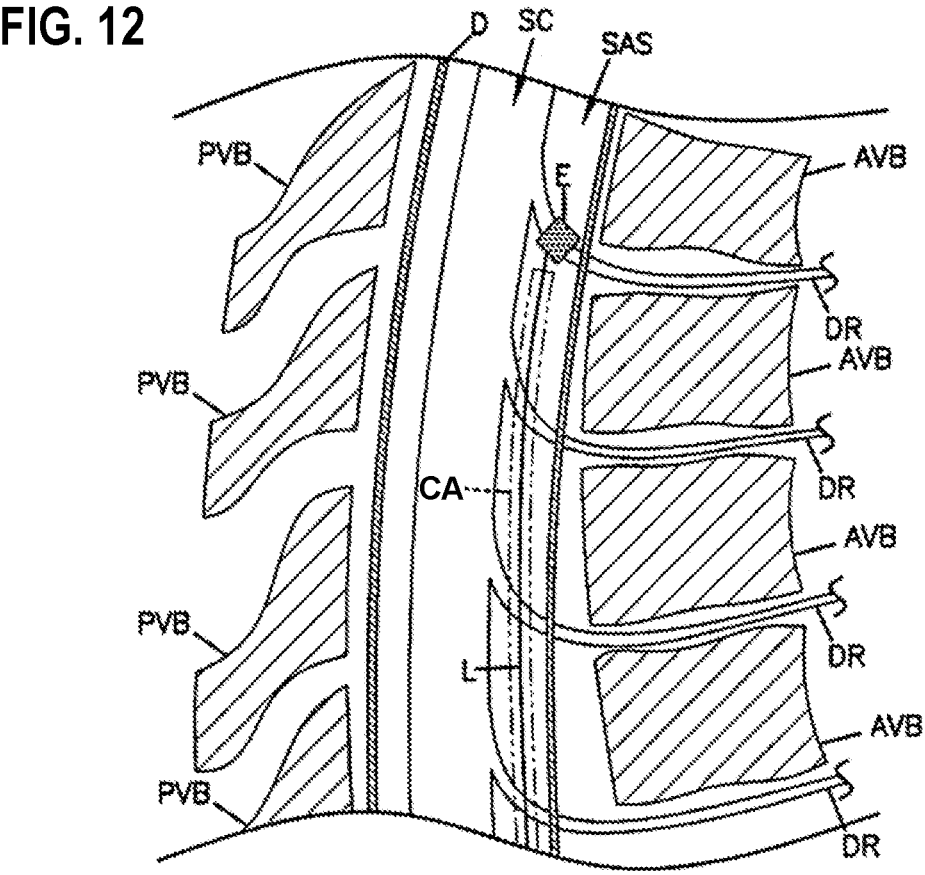
FIG. 12 is a schematic longitudinal, side-sectional showing of a segment of a spine with a catheter placement of an electrode on a dorsal root.
Figure 13:
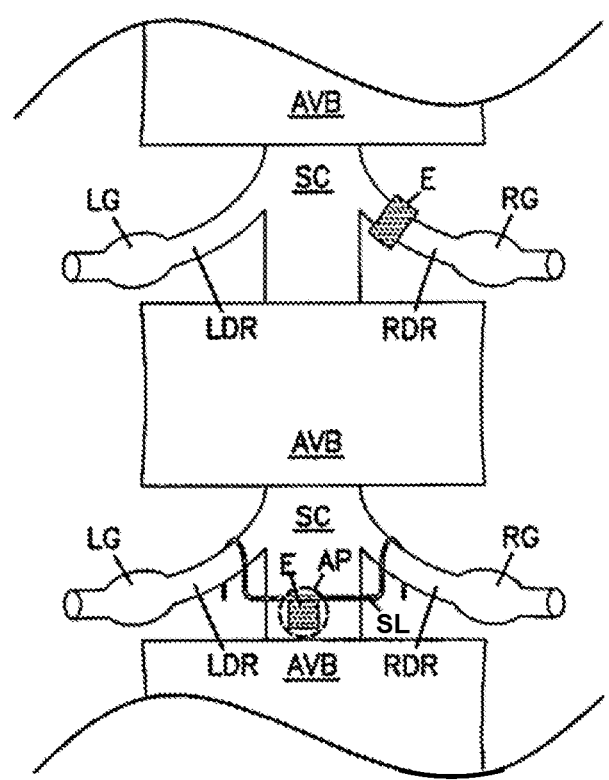
FIG. 13 is an anterior-posterior schematic representation of a segment of a spine with blocking signal electrodes shown in two positions.

FIGS. 11-13 illustrate application of the present invention to the spinal cord. By way of anatomical background, FIG. 11 shows, in cross-section, a spinal cord SC positioned between an anterior vertebral body AVB and a posterior vertebral body PVB. The patient's anterior-posterior axis A-A is shown separating the patient's right R and left L sides.

The spinal cord SC is shown enclosed within a dural layer D with opposing surfaces of the spinal cord SC and the dural layer D defining a subarachnoid space SAS. Extending laterally away from the spinal cord are left and right ventral roots LVR, RVR and right and left dorsal roots RDR, LDR. Also illustrated is a ganglion G. The spinal cord SC is illustrated as having identifiable areas of afferent and efferent fibers including ascending pathways AP areas and descending pathways DP areas.

According to the present invention, an electrode E is advanced either through open surgical or minimally invasive techniques into the subarachnoid space SAS and positioned on a root such as the right dorsal root RDR. Application of a blocking signal to the electrode E blocks signals such as pain signals from the dorsal root to the spinal cord SC. While a single monopolar electrode E is shown in FIG. 11, it will be appreciated that multiple electrodes including bipolar electrodes may be placed on the roots. For spinal treatments, such blocking signal may be as previously described and, preferably, has a frequency in excess of 3,000 Hz and more preferably about 5,000 Hz or more.

FIG. 12 is shown in vertical cross-section with multiple vertebral bodies and with a spinal cord extending between the vertebral bodies. For ease of schematic illustration, the dorsal roots are shown extending between the anterior bodies. It will be appreciated that such roots extend laterally from the spinal cord.

A catheter CA is shown in phantom lines for advancing an electrode to a dorsal root for placing the electrode on the dorsal root. The electrode lead extends from the electrode through an implantable or external pulse generator as previously described.

FIG. 13 illustrates an electrode E (the upper electrode E in the view of FIG. 13) placed on a dorsal root DR either surgically or through catheter delivery as previously described. Further, FIG. 13 shows an electrode E (the lower electrode E in the view of FIG. 13) placed overlying the spinal cord over a target area AP. In the example of FIG. 13, the target area AP is an identified area of ascending pathways for application of a blocking signal to the ascending pathways for blocking transmission of neural signals to the brain. The electrode is supported on a sling SL which is mounted on the left and right dorsal roots. It will be appreciated that the electrode so supported can be positioned over any area of the spinal cord to affect any desired area of ascending pathways or descending pathways. The electrodes are individually electrically connected to a controller (not shown, but such as controller 20 previously described) for creating a desired waveform.

With the foregoing detailed description of the present invention, it has been shown how the objects of the invention have been attained in a preferred manner. Modifications and equivalents of disclosed concepts, such as those which might readily occur to one skilled in the art, are intended to be included in the scope of the claims which are appended hereto.

What is claimed is:

1. An apparatus for treating pain, comprising:
   a) an electrode adapted to overlie a patient's spinal cord at a target area by way of a sling support configured to enter the subarachnoid space and mount on the left and right dorsal roots; and
   b) an implantable rechargeable controller that is electrically connected to the electrode and configured to provide electrical signals having a frequency of at least 3,000 Hz to the electrode that block propagation of action potentials, including transmission of pain signals, along ascending pathways in the spinal cord.

2. The apparatus of claim 1, wherein the implantable rechargeable controller provides bipolar charge balanced electrical signals.

3. The apparatus of claim 1, wherein the frequency is at least 5000 Hz.

4. A method of treating pain in a patient via the patient's spinal cord, comprising:
   a) placing an electrode carried by a sling supported by the patient's left and right dorsal roots in the patient's subarachnoid space so that the electrode overlies a dorsal surface of the spinal cord; and
   b) applying electrical signals having a frequency of at least 3,000 Hz to the electrode via an implantable rechargeable controller to block propagation of action potentials, including transmission of pain signals, along ascending pathways of the spinal cord.

5. The method of claim 4, wherein the implantable rechargeable controller provides bipolar charge balanced electrical signals.

6. The method of claim 4, wherein the frequency is at least 5000 Hz.

* * * * *